(12) United States Patent
Mjalli et al.

(10) Patent No.: US 7,208,601 B2
(45) Date of Patent: Apr. 24, 2007

(54) ARYL AND HETEROARYL COMPOUNDS, COMPOSITIONS, AND METHODS OF USE

(76) Inventors: Adnan M. M. Mjalli, 2902 Ellington Ct., Jamestown, NC (US) 27282; Devi Reddy Gohimmukkula, 4061 Cobblor Ct., Jamestown, NC (US) 27282; Sameer Tyagi, 5000 3H Samet Dr., High Point, NC (US) 27265

( * ) Notice: Subject to any disclaimer, the term of this patent is extended or adjusted under 35 U.S.C. 154(b) by 150 days.

(21) Appl. No.: 11/069,521

(22) Filed: Mar. 1, 2005

(65) Prior Publication Data

US 2005/0171148 A1    Aug. 4, 2005

Related U.S. Application Data

(63) Continuation-in-part of application No. 10/913,168, filed on Aug. 6, 2004.

(60) Provisional application No. 60/493,879, filed on Aug. 8, 2003, provisional application No. 60/493,878, filed on Aug. 8, 2003, provisional application No. 60/493,903, filed on Aug. 8, 2003.

(51) Int. Cl.
*C07D 217/00* (2006.01)
(52) U.S. Cl. .................................... 546/146
(58) Field of Classification Search ................ 546/146; 514/307
See application file for complete search history.

(56) References Cited

U.S. PATENT DOCUMENTS

| | | | |
|---|---|---|---|
| 4,675,439 A | 6/1987 | Mita et al. |
| 4,717,736 A | 1/1988 | Rokach et al. |
| 5,273,990 A | 12/1993 | De Lombert et al. |
| 5,354,905 A | 10/1994 | Sato et al. |
| 5,397,798 A | 3/1995 | Fitch et al. |
| 5,514,719 A | 5/1996 | LaTorse et al. |
| 5,518,735 A | 5/1996 | Sturzebecher et al. |
| 5,679,671 A | 10/1997 | Oinuma et al. |
| 5,703,106 A | 12/1997 | Fruh et al. |
| 5,750,520 A | 5/1998 | Danilewicz et al. |
| 5,780,498 A | 7/1998 | Saika et al. |
| 5,908,843 A | 6/1999 | Gante et al. |
| 5,977,075 A | 11/1999 | Ksander et al. |
| 5,977,178 A | 11/1999 | Hansen et al. |
| 6,001,820 A | 12/1999 | Hirsh et al. |
| 6,087,380 A | 7/2000 | Hauel et al. |
| 6,127,341 A | 10/2000 | Hansen et al. |
| 6,191,171 B1 | 2/2001 | DeLaszlo et al. |
| 6,194,448 B1 | 2/2001 | Bredrget et al. |
| 6,194,458 B1 | 2/2001 | Baker et al. |
| 6,262,084 B1 | 7/2001 | Biediger et al. |
| 6,284,871 B1 | 9/2001 | Mertens et al. |
| 6,291,511 B1 | 9/2001 | Durette et al. |
| 6,300,330 B1 | 10/2001 | Stocker et al. |
| 6,306,840 B1 | 10/2001 | Adams et al. |
| 6,331,564 B1 | 12/2001 | Brugnara et al. |
| 6,342,504 B1 | 1/2002 | Brunk et al. |
| 6,358,978 B1 | 3/2002 | Ritzeler et al. |
| 6,362,204 B1 | 3/2002 | Head et al. |
| 6,388,138 B1 | 5/2002 | Lee et al. |
| 6,388,148 B2 | 5/2002 | Heilmann et al. |
| 6,403,584 B1 | 6/2002 | De Laszlo et al. |
| 6,420,396 B1 | 7/2002 | Albers et al. |
| 6,423,727 B1 | 7/2002 | De Lombaert et al. |
| 6,469,047 B1 | 10/2002 | Jackson et al. |
| 6,521,666 B1 | 2/2003 | Sircar et al. |
| 6,528,275 B1 | 3/2003 | Quibell et al. |
| 6,528,655 B1 | 3/2003 | N'Zemba et al. |
| 6,559,174 B2 | 5/2003 | Lin et al. |
| 6,743,790 B2 | 6/2004 | Klingler et al. |
| 7,122,580 B2 * | 10/2006 | Mjalli et al. ................. 514/576 |
| 2002/0016461 A1 | 2/2002 | Albers et al. |
| 2002/0095041 A1 | 7/2002 | Chan et al. |
| 2002/0103192 A1 | 8/2002 | Curtin et al. |
| 2002/0151595 A1 | 10/2002 | Ries et al. |
| 2002/0173656 A1 | 11/2002 | Peyman et al. |

(Continued)

FOREIGN PATENT DOCUMENTS

DE      199 28 424      12/2000

(Continued)

OTHER PUBLICATIONS

Alves et al., "A Novel 3-step Enantioselective Synthesis of Pyrenylalanine with Subsequent Incorporation Into Opioid, CCK and Melanotropin Ligands" Biochemical and Biophysical Research Communications, vol. 318, pp. 335-340, (2004).

Amino et al., "Phenylalanine Derivatives Enhancing Intestinal Absorption of Insulin in Mice" Chemical and Pharmaceutical Bulletin, vol. 36, pp. 4426-4434, (1988).

Ankersen et al., "Demonstration of the Strength of Focused Combinatorial Libraries in SAR Optimisation of Growth Hormone Secretagogues" European Journal of Medicinal Chemistry, vol. 34, pp. 783-790, (1999).

Au-Yeung et al., "Unnatural A-Amino Acids Via Asymmetric Hydrogenation of Enamides" Transition Metals for Organic Synthesis and Fine Chemicals, vol. 2, pp. 14-25, (1998).

Balwierczak et al., "Characterization of a Potent and Selective Endothelin-B Receptor Antagonist, IRL 2500" Journal of Cardiovascular Pharmacology, vol. 26, pp. S393-S396, (1995).

(Continued)

*Primary Examiner*—D. Margaret Seaman
*Assistant Examiner*—Nizal S. Chandrakumar
(74) *Attorney, Agent, or Firm*—Kilpatrick Stockton LLP

(57) ABSTRACT

This invention provides aryl and heteroaryl compounds, methods of their preparation, pharmaceutical compositions comprising the compounds, and their use in treating human or animal disorders. The compounds of the invention may be useful as antagonists, or partial antagonist of factor IX and/or factor XI and thus, may be used to inhibit the intrinsic pathway of blood coagulation. The compounds may be useful in a variety of applications including the management, treatment and/or control of diseases caused in part by the intrinsic clotting pathway utilizing factor IX and/or XI.

9 Claims, 2 Drawing Sheets

U.S. PATENT DOCUMENTS

| | | |
|---|---|---|
| 2002/0198195 A1 | 12/2002 | Nazare et al. |
| 2003/0045480 A1 | 3/2003 | Safar et al. |
| 2003/0149083 A1 | 8/2003 | Tanaka et al. |
| 2004/0106626 A1 | 6/2004 | South et al. |
| 2004/0126856 A1 | 7/2004 | Bajaj et al. |
| 2004/0152888 A1 | 8/2004 | Bourguignon et al. |
| 2004/0198780 A1 | 10/2004 | Liu et al. |
| 2004/0220180 A1 | 11/2004 | Glick et al. |
| 2004/0241781 A1 | 12/2004 | Glick et al. |
| 2005/0049310 A1 | 3/2005 | Mjalli et al. |
| 2005/0053600 A1 | 3/2005 | Lane |
| 2005/0059705 A1 | 3/2005 | Mjalli et al. |
| 2005/0059713 A1 | 3/2005 | Mjalli et al. |
| 2005/0065346 A1 | 3/2005 | Ries et al. |
| 2005/0165107 A1 | 7/2005 | Inoue et al. |
| 2005/0187390 A1 | 8/2005 | Schmitz et al. |
| 2005/0187409 A1 | 8/2005 | Powers et al. |
| 2005/0203135 A1 | 9/2005 | Burdick et al. |
| 2005/0256116 A1 | 11/2005 | Clary et al. |

FOREIGN PATENT DOCUMENTS

| | | |
|---|---|---|
| EP | 0 150 118 | 9/1987 |
| EP | 1 213 288 | 12/2002 |
| FR | 2 847 251 | 5/2004 |
| GB | 1 501 541 | 2/1978 |
| GB | 2 354 440 | 3/2001 |
| JP | 61-227555 | 10/1986 |
| JP | 09-124569 | 5/1997 |
| JP | 2001-089368 | 4/2001 |
| JP | 2003-321358 | 11/2003 |
| JP | 2004-323487 | 11/2004 |
| WO | WO 1995-12611 | 5/1995 |
| WO | WO 1996-33170 | 10/1996 |
| WO | WO 1997-23508 | 7/1997 |
| WO | WO 1997-40065 | 10/1997 |
| WO | WO 1997-42216 | 11/1997 |
| WO | WO 1998-37075 | 8/1998 |
| WO | WO 1998-53817 | 12/1998 |
| WO | WO 1998-58950 | 12/1998 |
| WO | WO 1999-26923 | 6/1999 |
| WO | WO 1999-36393 | 7/1999 |
| WO | WO 2000-35864 | 6/2000 |
| WO | WO 2000-37429 | 6/2000 |
| WO | WO 2000-67746 | 11/2000 |
| WO | WO 2000-68188 | 11/2000 |
| WO | WO-2000-76971 | 12/2000 |
| WO | WO 2001-10823 | 2/2001 |
| WO | WO 2001-21584 | 3/2001 |
| WO | WO 2001-38309 | 5/2001 |
| WO | WO 2001-056994 | 8/2001 |
| WO | WO 2001-68586 | 9/2001 |
| WO | WO 2002-18320 | 3/2002 |
| WO | WO 2002-26717 | 4/2002 |
| WO | WO 2002-062748 | 8/2002 |
| WO | WO 2002-083842 | 10/2002 |
| WO | WO 2002-085841 | 10/2002 |
| WO | WO 2003-002545 | 1/2003 |
| WO | WO 2003-006444 | 1/2003 |
| WO | WO 2003-007945 | 1/2003 |
| WO | WO 2003-033496 | 4/2003 |
| WO | WO 2003-072536 | 9/2003 |
| WO | WO 2004-014844 | 2/2004 |
| WO | WO 2004-046091 | 6/2004 |
| WO | WO 2004-080970 | 9/2004 |
| WO | WO 2004-084842 | 10/2004 |
| WO | WO 2004-110983 | 12/2004 |
| WO | WO 2005-012288 | 2/2005 |
| WO | WO 2005-039494 | 5/2005 |

OTHER PUBLICATIONS

Batt et al., "5-Amidinoindoles as Dual Inhibitors of Coagulation Factors IXa and Xa" Bioorganic & Medicinal Chemistry Letters, vol. 14, pp. 5269-5273, (2004).

Bebernitz et al., "Anilides of R-Trifluoro-2-hydroxy-2-methylpropionic Acid as Inhibitors of Pyruvate Dehydrogenase Kinase", Journal of Medicinal Chemistry, vol. 43, pp. 7121-7124, (2000).

Bedsted et al., "Heparin and Calcium Ions Dramatically Enhance Antihrombin Reactivity With Factor IXa by Generating New Interaction Exosites" Biochemistry, vol. 42, pp. 8143-8152, (2003).

Benincosa et al., "Pharmacokinetics and Pharmacodynamics of a Humanized Monoclonal Antibody to Factor IX in Cynomolgus Monkeys" The Journal of Pharmacology and Experimental Therapeutics, vol. 292, pp. 810-816, (2000).

Blostein et al., "The Gla Domain of Factor IXa Binds to Factor VIIIa in the Tenase Complex" The Journal of Biological Chemistry, vol. 278, pp. 31297-31302, (2003).

Boitano et al., "Structure Activity Studies of a Novel Cytotoxic Benzodiazepine" Bioorganic & Medicinal Chemistry Letters, vol. 13, pp. 3327-3330, (2003).

Burdick et al, "N-Benzoyl Amino Acids as LFA-1/ICAM Inhibitors 1: Amino Acid Structure-Activity Relationship" Bioorganic Medicinal Chemistry Letters, vol. 13, pp. 1015-1018 (2003).

Burger et al., "Ein Neuer Allgemeiner Zugang Zu α-Trifluormethyl-Substituierten Aromatischen und Heteroaromatischen α-Aminosäuren" Synthesis, vol. 11, pp. 850-855, (1989).

Burk et al., "A Versatile Tandem Catalysis Procedure for the Preparation of Novel Amino Acids and Peptides" Journal of the American Chemical Society, vol. 116, pp. 10847-10848, (1994).

Burk et al., "Asymmetric Catalytic Routes to Chiral Building Blocks of Medicinal Interest" Pure and Applied Chemistry, vol. 68, pp. 37-44, (1996).

Castanedo et al, "Solid-Phase Synthesis of Dual Alpha4beta1/alpha4beta7 Integrin Antagonists: Two Scaffolds with Overlapping Pharmacophores", Bioorganic & Medicinal Chemistry Letters, Oxford, GB vol. 12, pp. 2913-2917. (2002).

Chapman et al., "Synthesis of Functionalised Phenylalanines Using Rhodium Catalysis in Water" Advanced Synthesis & Catalysis, vol. 345, pp. 353-355, (2003).

Chisholm et al., "Identification of the Enantioselective Step in the Asymmetric Catalytic Hydrogenation of a Prochiral Olefin" Journal of the American Chemical Society, vol. 102, pp. 5952-5954, (1980).

Cui et al., "An Oxyanion-Hole Selective Serine Protease Inhibitor In Complex With Tryspin" Bioorganic & Medicinal Chemistry Letters, vol. 10, pp. 41-46, (2002).

Das et al., "Molecular Design and Structure—Activity Relationships Leading to the Potent, Selective, and Orally Active Thrombin Active Site Inhibitor BMS—189664" Bioorganic & Medicinal Chemistry Letters, vol. 12, pp. 45-49, (2002).

Database CAPLUS Chemical Abstracts Service, Columbus, Ohio, US, XP002319820, retrieved from STN Database Accession No. 1973: 504834 Abstract; RN 42787-97-3 Abstract & I. Hahnemann et al, Journal Fuer Praktische Chemie, vol. 315, No. 4, 1973, pp. 796-800.

Delazlo et al., "Identification of Unique VLA-4 Antagonists From a Combinatorial Library" Bioorganic & Medicinal Chemistry Letters, vol. 12, pp. 685-688, (2002).

Dobler et al., "Unusual Amino Acids IV. Asymmetric Synthesis of Thienylalanines" Tetrahedron: Asymmetry, vol. 4, pp. 1833-1842, (1993).

Doherty et al., "N-Aryl 2, 6-Dimethoxybiphenylalanine Analogues as VLA-4 Antagonists" Bioorganic & Medicinal Chemistry Letters, vol. 12, pp. 729-731, (2002).

Egger et al., "A Small Molecule $\alpha_4\beta_1/\alpha_4\beta_7$ Antagonist Differentiates Between the Low-Affinity States of $\alpha_4\beta_1$ and $\alpha_4\beta_7$: Characterization of Divalent Cation Dependence" Journal of Pharmacology and Experimental Therapeutics, vol. 306, pp. 903-913, (2003).

Egusa et al., "One-Dimensional Aromatic Crystals in solution. 4. Ground-and Excited-State Interactions of Poly(L-1 Pyrenylalanine)

Studied by Chiroptical Spectroscopy Including Circularly Polarized Fluorescence and Fluorescence-Detected Circular Dichroism" Macromolecules, vol. 18, pp. 882-889, (1985).

Feuerstein et al., "Antithrombotic Efficacy of a Novel Murine Antihuman Factor IX Antibody In Rats" Arteriosclerosis, Thrombosis, and Vascular Biology, vol. 19, pp. 2554-2562, (1999).

Firooznia et al., "Synthesis of 4-Substituted Phenylalanines by Cross-Coupling Reactions: Extension of the Methodology to Aryl Chlorides" Tetrahedron Letters, vol. 39, pp. 3985-3988, (1998).

Früh et al., "IRL 2500: a Potent $ET_B$ Selective Endothelin Antagonist" Bioorganic & Medicinal Chemistry Letters, vol. 6, pp. 2323-2328, (1996).

Gadek et al., "Generation of an LFA-1 Antagonist by the Transfer of the ICAM-1 Immunoregulatory Epitope to a Small Molecule" Science, vol. 295, pp. 1086-1089, (2002).

Greenspan P.D. et al., "N-aryl Cinnamides: A Novel Class of Rigid and Highly Potent Leukotriene B4 Receptor Antagonists", Bioorganic and Medicinal Chemistry Letters, vol. 7, No. 7, 1997, pp. 949-954. (1997).

Hirayama et al., "The Discovery of YM-60828: a Potent, Selective and Orally-Bioavailable Factor Xa Inhibitor" Bioorganic & Medicinal Chemistry Letters, vol. 10, pp. 1509-1523, (2002).

Hoshina et al. "2, 3-Diphenylpropionic Acids as Potent VLA-4 Antagonists" Bioorganic & Medicinal Chemistry Letters, vol. 15, pp. 217-220, (2005).

Hsieh et al., "Topographic Probes of Angiotensin and Receptor: Potent Angiotensin II Agonist Containing Diphenylalanine and Long-Acting Antagonists Containing Biphenylalanine and 2-Indan Amino Acid in Position 8" Journal of Medicinal Chemistry, vol. 32, pp. 898-903, (1989).

Hsu et al., "The Distinct Roles That Gln-192 and Glu-217 of Factor IX Play in Selectivity For Macromolecular Substrates and Inhibitors" Biochemistry, vol. 40, pp. 11261-11269, (2001).

Ikeda, et al., "Diastereoselective Hydrogenation of Dehydrodipeptides with a Polycondensed Aromatic Ring at β-Position of Dehydroamino Acid Residue" Chemistry Express, vol. 5, pp. 29-32, (1990).

International Search Report for PCT Application PCT/US2004/025429 mailed Jan. 26, 2005.

International Search Report for PCT Application PCT/US2004/025463 mailed Jan. 26, 2005.

International Search Report for PCT Application PCT/US2004/025478 mailed Jan. 26, 2005.

International Search Report for related PCT Application PCT/US03/25045 mailed Mar. 14, 2005.

Kagan et al., "Asymmetric Catalytic Reduction With Transition Metal Complexes. I. A Catalytic System of Rhodium (I) With (-)-2,3-O-isopropylidene-2,3-dihydroxy-1,4-bis(diphenylphosphino)butane, A New Chiral Diphosphine" Journal of the American Chemical Society, vol. 94, pp. 6429-6433, (1972).

Kannan et al., "Stereochemistrhy of the Cyclic Tripeptide Antibiotic WS-43708A" Journal of Organic Chemistry, vol. 52, pp. 5435-5437, (1987).

Kato et al., "Novel Benzamides as Selective and Potent Gastrokinetic Agents. III. Synthesis and Structure-Activity Relationships of 4-amino-5-chloro-2-methoxy-and 2-ethoxy-N-[(4-substituted 2-morpholinyl) methyl]-benzamides" Chemical and Pharmaceutical Bulletin, vol. 40, pp. 652-660, (1992).

Knowles et al., "Photochemical Alkylation's of Glycine Leading to Phenylalanines", Tetrahedron Letters, vol. 41, pp. 7121-7124, (2000).

Knowles, H.S. et al., "A Photochemical Approach to Phenylalanines and Related Compounds by Alkylation of Glycine" Tetrahedron, vol. 57, pp. 98115-98124. (2001).

Kolkman et al., "Surface-Loop Residue Lys[316] In Blood Coagulation Factor IX is a Major Determinant For Factor X But Not Antithrombin Recognition" Biochemistry, vol. 350, pp. 701-707, (2000).

Krause et al., "Unusual Amino Acids VI. Substituted Arylamino Acids by Asymmetric Hydrogenation of N-Cbz and N-Boc Protected Dehydroamino Acid Derivatives" Chirality, vol. 8, pp. 173-188, (1996).

Kreuzfeld et al., "Unusual Amino Acids v. Asymmetric Hydrogenation of (z)-N-acylaminocinnamic Acid Derivatives Bearing Different Protective Groups" Tetrahedron:Asymmetry, vol. 4, pp. 2047-2051, (1993).

Ksander et al., "Dipeptide Sulfonamides as Endothelin $ET_A/ET_B$ Receptor Antagonists[1]" Canadian Journal of Physiology and Pharmacology, vol. 80, pp. 464-469, (2002).

Kudlacz et al., "Pulmonary Eosinophilia in a Murine Model of Allergic Inflammation is Attenuated By Small Molecule α4β1 Antagonists" Journal of Pharmacology and Experimental Therapeutics, vol. 301, pp. 747-752, (2002).

Lettre et al., "Chemically Labeled Antigens. III. Introduction of 4-Ring Systems Into Proteins" Hoppe-Seyler's Zeitschrift fur Physiologische Chemie, vol. 267, pp. 108-114, (1940).

Leung et al., "Use of A-192621 and IRL-2500 to Unmask the Mesenteric and Renal Vasodilator Role of Endothelin ETb Receptors", Journal of Cardiovascular Pharmacology, vol. 39, pp. 533-543 (2002).

Lopez-Arbeloa et al., "Chiral Discrimination of the Intermolecular Excimer of N-acetyl-1-pyrenylalanine Methyl Ester" Journal of the American Chemical Society, vol. 109, pp. 3068-3076, (1987).

Ma et al., "Synthesis of the Biaryl Moiety of the Proteasome Inhibitors TMC-95 Via a Ligandless Pd(Oac)$_2$-Catalyzed Suzuki-Coupling Reaction" Tetrahedron Letters, vol. 42, pp. 5279-5281, (2001).

Macchia et al., "Toward the Rational Development of Peptidomimetic Analogs of the C-Terminal Endothelin Hexapeptide: Development of a Theoretical Model" Farmaco, vol. 53, pp. 545-556, (1998).

Macchiarulo et al., "Insights Into Phenylalanine Derivatives Recognition of VLA-4 Integrin: From a Pharmacophoric Study to 3D-QSAR and Molecular Docking Analyses" Journal of Chemical Information and Computer Sciences, vol. 44, pp. 1829-1839, (2004).

Mazaleyrat et al. "Practical Resolution of an Atropoisomeric α,αα-Disubstituted Glycine with L-Phenylalanine Cyclohexylamide as Chiral Auxiliary" Tetrahedron: Asymmetry, vol. 9, pp. 2701-2713, (1998).

Melillo et al., "Practical Enantioselective Synthesis of a Homotyrosine Derivative and (R,R)-4-propyl-9-Hdroxynaphthoxazine, a Potent Dopamine Agonist" Journal of Organic Chemistry, vol. 52, pp. 5143-5150, (1987).

Mimatsu et al., "Circularly Polarized Luminescence Generated by Intramolecular Excimer of a Chiral Pyrenyl Compound" New Technologies & Medicine, vol. 2, pp. 45-47, (2001).

Mustafa et al., "Reactivity of Unsaturated Centres in Heterocycles and Chalkones Toward Diazoalkanes" Tetrahedron, vol. 21, pp. 2215-2229, (1965).

O'Donnell M.J. et al., "Enantioselective Solid-Phase Synthesis of α-Amino Acid Derivatives", Tetrahedron, vol. 55, pp. 6347-6362. (1999).

O'Donnell et al., "An Efficient Homogeneous Catalytic Enantioselective Synthesis of α-Amino Acid Derivatives" Tetrahedron Letters, vol. 39, pp. 8775-8778, (1998).

Ohmomo et al., "Synthesis and Evaluation of Iodinated Benzamide Derivatives as Selective and Reversible Monoamine Oxidase B Inhibitors" Chemical and Pharmacuetical Bulletin, vol. 40, pp. 1789-1792, (1992).

Ojima et al., "Asymmetric Hydrogenation of Prochiral Olefins Catalyzed By Rhodium Complexes With Chiral Pyrrolidinodiphosphines. Crucial Factors for the Effective Asymmetric Induction" Journal of Organic Chemistry, vol. 45, pp. 4728-4739, (1980).

Okamoto et al., "Optical Resolution of Amino Acid Derivatives By High-Performance Liquid Chromatography On Tris(phenylcarbamate)s of Cellulose and Amylose" Journal of Chromatography, vol. 477, pp. 367-376, (1989).

Omote et al., "Synthesis and Melanogenesis of the DOPA Dimer" Bulletin of the Chemical Society of Japan, vol. 42, pp. 1752-1754, (1969).

Omote et al., "Dopa Dimer" Chemical Communications, vol. 4, p. 190, (1968).

Ooi et al., "Design of N-spiro C₂-Symmetric Chiral Quaternary Ammonium Bromides As Novel Chiral Phase-Transfer Catalysts: Synthesis and Application to Practical Asymmetric Synthesis of α-Amino Acids" Journal of the American Chemical Society, vol. 125, pp. 5139-5151, (2003).

Pawloswska et al, "Synthesis of Dextro-and Laevorotatory N-acety-β-(2-dibenzofuryl)alanines" Polish Journal of Chemistry, vol. 58, pp. 619-620, (1984).

Pierson et al., "Catalytic Asymmetric Oxonium Ylide—[2,3] Sigmatropic Rearrangement With Diazocarbonyl Compounds: First Use of $C_2$-Symmetry in Rh(II) Carboxylates" Tetrahedron Letters, vol. 38, pp. 4705-4708, (1997).

Rose et al., "Substrate Recognition Drives the Evolution of Serine Proteases" The Journal of Biological Chemistry, vol. 277, pp. 19243-19246, (2002).

Russell et al., "Characterization of the Binding of Endothelin $ET_8$ Selective Ligands In Human and Rat Heart" British Journal of Pharmacology, vol. 119, pp. 631-636, (1996).

Sakaguchi et al., "Synthesis, Gastrointestinal Prokinetic Activity and Structure-Activity Relationships of Novel N-[[2-(dialkylamino)ethoxy]benzyl]benzamide Derivatives" Chemical and Pharmaceutical Bulletin, vol. 40, pp. 202-211, (1992).

Sakaki et al., "Discovery of IRL 3461: a Novel and Potent Endothelin Antagonist With Balanced $ET_A/ET_B$ Affinity" Bioorganic & Medicinal Chemistry Letters, vol. 8, pp. 2241-2246, (1998).

Satoh et al., "Synthesis of 4-Substituted Phenylalanine Derivatives By Cross-Coupling Reaction of p-Boronophenylalanines" Tetrahedron Letters, vol. 38, pp. 7645-7648 (1997).

Schmidt et al., "Structure-Function Relationships In Factor IX and Factor IXa" Trends in Cardiovascular Medicine, vol. 13, pp. 39-45, (2003).

Shieh et al., "A Simple Asymmetric Synthesis of 4-arylphenylalanines Via Palladium-Catalyzed Cross-Coupling Reaction of Arylboronic Acids With Tyrosine Triflate" Journal of Organic Chemistry, vol. 57, pp. 379-381, (1992).

Shikamoto et al., "Crystal Structure of $Mg^{2+}$-and $Ca^{2+}$-Bound Gla Domain of Factor IX Complexed with Binding Protein" The Journal of Biological Chemistry, vol. 278, pp. 24090-24094, (2003).

Shrader et al., "Neutral Inhibitors of the Serine Protease Factor Xa", Bioorganic & Medicinal Chemistry Letters, vol. 11, pp. 1801-1804, (2001).

Sircar et al, "Synthesis and SAR of N-benzoyl-L-Biphenylalanine Derivatives: Discovery of TR-14035, A Dual Alpha4Beta7/Alpha4Beta1 Intergrin Antagonist", Bioorganic & Medicinal Chemistry, vol. 10, pp. 2051-2066. (2002).

Smallheer et al., "SAR and Factor IXa Crystal Structure of a Dual Inhibitor of Factors IXa and Xa" Bioorganic & Medicinal Chemistry Letters, vol. 14, pp. 5263-5267, (2004).

Stoilova-Mcphie et al., "3-Dimensional Structure of Membrane-Bound Coagulation Factor VIII: Modeling of the Factor VIII Heterodimer Within a 3-Dimensional Density Map Derived By Electron Crystallography" Blood, vol. 99, pp. 1215-1223, (2002).

Strauss et al., "Optically Active Cyclic Hexapeptides With Covalently Attached Pyrene Probes: Selective Alkaline Earth Metal Ion Recognition Using Excimer Emission" Organic Letters, vol. 4, pp. 683-686, (2002).

Taudien et al., "Unusual Amino Acids III. Asymmetric Synthesis of 3-arylalanines" Tetrahedron: Asymmetry, vol. 4, pp. 73-84, (1993).

Toomey et al., "Inhibition of Factor IX(a) Is Protective In a Rat Model of Thromboembolic Stroke" Stroke, vol. 33, pp. 578-585, (2002).

Urbahns et al., "Biphenyls as Potent Vitronectin Receptor Antagonists. Part 2: Biphenylalanine Ureas" Bioorganic & Medicinal Chemistry Letters, vol. 13, pp. 1071-1074, (2003).

Webb et al., "Effects of the $ET_B$-Selective Antagonist IRL 2500 In Conscious Spontaneously Hypertensive and Wistar-Kyoto Rats" Journal of Cardiovascular Pharmacology, vol. 26, pp. S389-S392, (1995).

Weltz et al., "New Anticoagulant Drugs" Chest, vol. 119, pp. 95s-107s, (2001).

Yabe et al., "Analogues of Luteinizing Hormone-Releasing Hormone With Modification In Position $3^1$" Chemical & Pharmaceutical Bulletin, vol. 24, pp. 3149-3157, (1976).

Yang et al., "Localization of the Heparin Binding Exosites of Factor'IXa" The Journal of Biological Chemistry, vol. 277, pp. 50756-50760, (2002).

Zhang et al., "Acylation of 2,5-Dimethoxycarbonyl[60]fulleropyrrolidine and Synthesis of Its Multifullerene Derivatives" Journal of Organic Chemistry, vol. 67, pp. 883-891, (2002).

* cited by examiner

ARYL AND HETEROARYL COMPOUNDS, COMPOSITIONS, AND METHODS OF USE

STATEMENT OF RELATED APPLICATIONS

The present application is a continuation in part application to U.S. application Ser. No. 10/913,168 filed on Aug. 6, 2004, which in turn claims priority under 35 USC 119 to the following U.S. Provisional Patent Applications: Ser. No. 60/493,879, filed Aug. 8, 2003, entitled "Aryl and Heteroaryl Compounds as Antiviral agents"; Ser. No. 60/493,878, filed Aug. 8, 2003, entitled "Aryl and Heteroaryl Compounds and Methods to Modulate Red Blood Cell Production"; Ser. No. 60/493,903, filed Aug. 8, 2003, entitled "Aryl and Heteroaryl Compounds and Methods to Modulate Coagulation", the entirety of which are herein incorporated by reference.

FIELD OF THE INVENTION

This invention relates to aryl and heteroaryl compounds and compositions that may be antagonists of the intrinsic clotting pathway by binding to and inhibiting the function of factor XI or of both factors XI and IX, and methods of use for such compounds and compositions.

BACKGROUND OF THE INVENTION

Hemostasis, the arrest of bleeding from an injured blood vessel, requires the coordinated endeavors of vascular, platelet, and plasma factors to eventually form a hemostatic seal or a blood clot. In normal hemostasis, collective activity of these factors is counterbalanced by regulatory mechanisms to limit the accumulation of platelets and fibrin in the area of injury.

Upon injury to a blood vessel, vascular factors reduce blood flow from the blood vessel by local vasoconstriction and compression of injured vessels. At the same time, platelets adhere to the site of vessel wall injury and form aggregates called hemostatic plugs, which form the first key element of the hemostatic seal. Platelets also release factors that provide surface membrane sites and components for the formation of enzyme/cofactor complexes in blood coagulation reactions. Through a series of interacting and propagating zymogen activations, the activated form of one plasma factor catalyzes the activation of the next plasma factor. This cascade of blood coagulation reactions eventually forms a fibrin clot. The fibrin clot, an insoluble fibrin matrix that radiates from and anchors the hemostatic plug, is the second key element of the hemostatic seal.

Specifically, the cascade of blood coagulation reactions discussed involves two interdependent pathways, an intrinsic pathway and an extrinsic pathway. Both pathways ultimately catalyzes the proteolytic activation of factor X to factor Xa.

Damage to the blood vessel or a negatively charged surface initiates blood clotting by the intrinsic pathway. As seen in FIG. 1, the major components of the intrinsic pathway include factor VIII, a non-enzymatic co-factor, and factors IX and XI, zymogen serine proteases. The initiation of the intrinsic pathway results in the activation of factor XI to XIa. Factor XIa, as well as the presence of the factor VIIa/tissue factor complex involved in the extrinsic pathway, catalyzes the activation of factor IX to factor IXa. The presence of factor IXa, in combination with the activated form of factor VIII on an appropriate phospholipid surface, results in the formation of a tenase complex (10). The tenase complex catalyzes the formation of factor Xa from its zymogen, factor X.

Exposure of blood to injured tissue initiates blood clotting by the extrinsic pathway. As is shown in FIG. 1, the major components of the extrinsic pathway are factor VII, a zymogen serine protease, and tissue factor, a membrane bound protein. Tissue factor serves as the requisite non-enzymatic co-factor for factor VII. The initiation of the extrinsic pathway is thought to be an autocatalytic event resulting from the activation of factor VII by trace levels of activated factor VII (factor VIIa), both of which are bound to newly exposed tissue factor on membrane surfaces at sites of vascular damage (20). The factor VIIa/tissue factor complex directly catalyzes the formation of factor Xa from factor X.

Once the initial intrinsic or extrinsic cascade results in the activation of factor X, factor Xa catalyzes the penultimate step in the blood coagulation cascade, the formation of serine protease thrombin. As seen in FIG. 2, thrombin formation occurs when a prothrombinase complex, comprising of factor Xa, the non-enzymatic co-factor Va and the substrate prothrombin, is assembled on an appropriate phospholipid surface (30).

Once formed, thrombin functions as part of a feedback loop, controlling the activation of factors V and VIII. It additionally catalyzes both the activation of factor VIII and the conversion of fibrinogen to fibrin. Finally, the factor VIIIa interacts with fibrin to catalyze the formation of a thrombus, or crosslinked fibrin clot.

In normal hemostasis, the process of clot formation (blood coagulation) and clot dissolution (fibrinolysis) is delicately balanced. A slight imbalance between the processes of clot formation and dissolution can lead to excessive bleeding or thrombosis. Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively [Ross, A. M., Thrombosis in Cardiovascular Disorder, p. 327, W. B. Saunders Co. (Fuster, V. and Verstraete, M. edit. 1991); Califf, R. M. and Willerson, J. T., Id. at p 389]. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered intravenously, has not been shown to be universally effective in the treatment or prevention of acute arterial thrombosis or rethrombosis [Prins, M. H. and Hirsh, J., J. Am. Coll. Cardiol., 67: 3A (1991)].

Besides the unpredictable, recurrent thrombotic reocclusion which commonly occurs following PTCA, a profound restenosis of the recanalized vessel occurs in 30 to 40% of patients 1 to 6 months following this procedure [Califf, R. M. et al., J. Am. Coll. Cardiol., 17: 2B (1991)]. These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacological treatment for the prevention of vascular restenosis following mechanical recanalization.

Numerous strategies have been developed for the treatment of thrombotic disorders. Many antithrombotic therapies are based on interference in the hemostatic system. This approach carries the inherent risk of bleeding, since the hemostatic system is no longer fully responsive to potential injury. Therefore, antithrombotic benefits are normally associated with antihemostatic risks. In attempts to improve the benefit-to-risk ratio, antithrombotic agents are continuously being developed. Various antithrombotic strategies include administering general inhibitors of thrombin formation such as heparin or vitamin K antagonists; administering specific thrombin inhibitors; administering specific factor Xa inhibitors; and administering inhibitors of platelet activation and adhesion.

Evaluation of current antithrombotic strategies in terms of antithrombotic benefits versus antihemostatic risks reveals that the benefit-to-risk ratio tends to be more favorable for strategies that interfere with one specific step rather than in a more general phase of the hemostatic system [L. A. Harker, Biomedical Progress vol 8, 1995, 17–26]. For example, the development of inhibitors specific for factor Xa is an improvement from general and specific thrombin inhibitors. But, this approach blocks the common (intrinsic and extrinsic) pathway of thrombin generation (see FIG. 1), and thereby thrombin-dependent platelet activation. Thus, a need exists for more specific anti-thrombotic agents that selectively inhibit one single hemostatic pathway, while leaving other pathways unaffected.

SUMMARY OF THE INVENTION

The present invention provides compounds of Formula (I or X), pharmaceutical compositions, and methods for the treatment of cardiovascular diseases. Embodiments of the present invention provide compounds of Formula (I or X) as depicted below. Embodiments of the present invention also provide methods for the preparation of compounds of Formula (I or X) and pharmaceutical compositions comprising compounds of Formula (I or X).

In another embodiment, the present invention provides methods for the use of compounds of Formula (I or X) and pharmaceutical compositions comprising compounds of Formula (I or X) in treating human or animal disorders.

Compounds of Formula (I or X) may be useful as modulators of the intrinsic clotting pathway by inhibiting the biological activity of factor XI and/or both factor IX and factor XI. Compounds of Formula (I or X) may be useful in a variety of applications including management, treatment, control, and/or as an adjunct of diseases in humans caused in part by the intrinsic clotting pathway utilizing factor XI/IX. Such diseases or disease states include cardiopulmonary bypass, stroke, myocardial infarction, deep vein thrombosis associated with surgical procedures or long periods of confinement, acute and chronic inflammation and clotting associated with hemodialysis.

BRIEF DESCRIPTION OF THE FIGURES

The present invention will be described with reference to the accompanying drawings, wherein.

DETAILED DESCRIPTION

Figure 1:
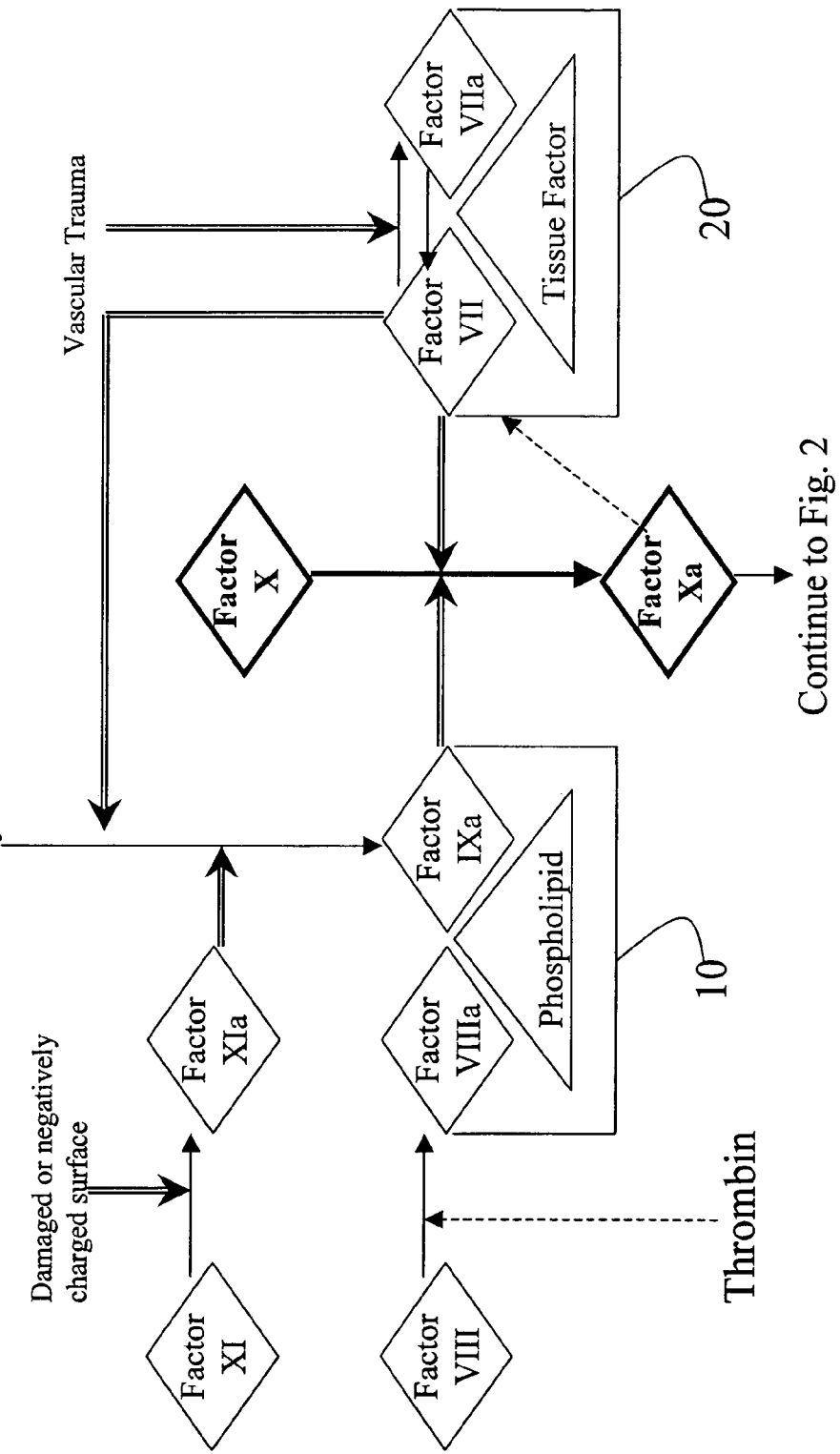
FIG. 1 is a diagram depicting the steps involved in the intrinsic and extrinsic blood clotting cascades, from time of trauma to the activation of factor X.
Figure 2:
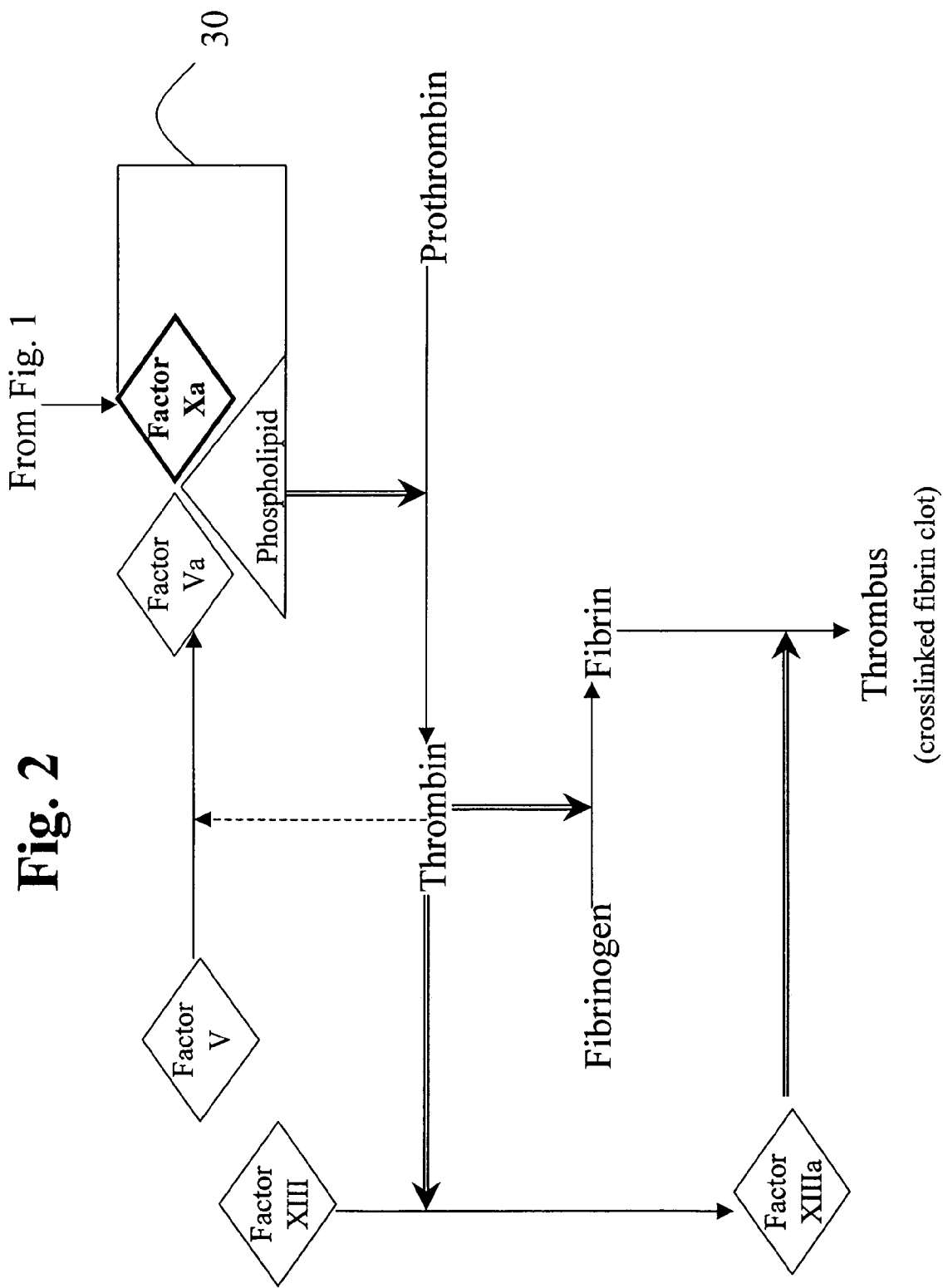
FIG. 2 is a diagram depicting the steps following initial intrinsic and extrinsic blood clotting cascades, beginning with the formation of Xa and culminating in the formation of a thrombus.

Two blood coagulation pathways are associated with normal hemostasis: intrinsic and extrinsic. These two coagulation pathways converge in the formation of factor Xa (FIGS. 1 & 2). But, these two coagulation pathways are interdependent because complete elimination of the intrinsic pathway can lead to uncontrolled bleeding. For example, Type B hemophiliacs completely lack factor IX or factor IX function and have a phenotype characterized by a severe bleeding disorder. Thus, the direct factor VIIa/tissue factor activation of factor X, which bypasses the need for factor VIII and factor IX, is insufficient for normal hemostasis. Conversely, formation of the factor VIIIa/IXa phospholipid factor X activator (tenase complex) (20) is essential for normal hemostasis.

Selective inhibition of the intrinsic pathway of coagulation with a factor XI antagonist or a dual factor XI/IX antagonist can provide a method to inhibit the clotting cascade associated with some surgery, stroke, myocardial infarction and hemodialysis while leaving the clotting pathway associated with external lesions such as trauma or abscess intact. Factor XI and IX are primarily associated with the intrinsic clotting pathway. Antagonists which have activity to factor XI or dual activity to factor XI/IX may have a therapeutic benefit in diseases associated with intrinsic pathway clotting by inhibiting intravascular thrombosis. Additionally, antagonists of factor XI or dual antagonists of factor XI/IX may not have the side effect of unwanted or uncontrollable bleeding by impairing extravascular hemostasis associated with wound healing.

Some point mutations in factor IX partially inhibit its function and result in a mild or moderate phenotype manifested as a non-life threatening bleeding disorder [Bowen, D. J., J. Clin. Pathol: Mol. Pathol. 55:1–18 (2002)]. These point mutations cause factor IX to behave as if it were subject to a partial antagonist. In the presence of a partial antagonist, factor IX should maintain some activity, even at saturation levels of the partial antagonist. As a result of the point mutations in factor IX, its activity is reduced along with clotting associated with the intrinsic pathway, but some residual activity remains that leaves the extrinsic pathway intact. Additionally, an antibody directed against the gamma-carboxyglutamic acid domain of Factor XI demonstrated efficacy in animal models of thrombosis without an increase in bleeding times [Refino, C. J., et al. Thromb Haemost. 82(3) 1188–1195 (1999)].

The present invention provides compounds of Formula (I or X), pharmaceutical compositions, and methods to inhibit the clotting activities of factor XI and/or both factor IX and factor XI. Inhibition of hemostasis with agents that may selectively inhibit the intrinsic pathway of factor X activation may leave the extrinsic pathway intact and allow the formation of small, but hemostatically important amounts of factor Xa and thrombin.

Embodiments of the present invention provide compounds of Formula (I or X) as depicted below. Embodiments of the present invention also provide methods of the preparation of compounds of Formula (I or X) and pharmaceutical compositions comprising compounds of Formula (I or X).

In another embodiment, the present invention provides methods for the use of compounds of Formula (I or X) and pharmaceutical compositions comprising compounds of Formula (I or X) in treating human or animal disorders. Compounds of the Formula (I or X) may be useful as modulators of the intrinsic clotting pathway by inhibiting the biological activities of factor XI and/or both factor IX and factor XI. Compounds of Formula (I or X) may be useful in a variety of applications including management, treatment, control, and/or as an adjunct of diseases in humans caused in part by the intrinsic clotting pathway utilizing factors XI/IX. Such diseases or disease states include cardiopulmonary bypass, stroke, myocardial infarction, deep vein thrombosis associated with surgical procedures or long periods of confinement, acute and chronic inflammation and clotting associated with hemodialysis.

In a first aspect, the present invention provides a compound comprising at least one moiety of the Formula (I or X).

In one aspect, the present invention provides compounds which are represented by Formula I:

$$Ar_2—K \quad (I)$$

wherein $Ar_2$ comprises an aryl, heteroaryl, fused cycloalkylaryl, fused cycloalkylheteroaryl, fused heterocyclylaryl, or fused heterocyclylheteroaryl group optionally substituted 1 to 7 times. In an embodiment, $Ar_2$ comprises an aryl, heteroaryl, or fused arylheterocyclyl group optionally substituted 1 to 7 times. In another embodiment, $Ar_2$ comprises a phenyl, naphthyl, pyridyl, indolyl, isoquinolyl, pyrimidyl, tetrahydroisoquinolyl, quinoxazoyl, or quinazolyl group optionally substituted 1 to 7 times. In another embodiment, $Ar_2$ comprises a substituted phenyl, 2-naphthyl, 2-pyridyl, 3-isoquinolyl, 2-pyrimidyl, 2-quinazolyl, or 3-tetrahydroisoquinolyl group having 1 to 5 substituents wherein the substituents independently comprise:

a)-fluoro;
b)-chloro;
c)-bromo;
d)-iodo;
e)-cyano;
f)-nitro;
g)-perfluoroalkyl;
h)-$T_1$—$R_{20}$;
i)-alkyl;
j)-aryl;
k)-heteroaryl;
l)-heterocyclyl;
m)-cycloalkyl;
n)-alkylene-aryl;
o)-alkylene-arylene-aryl;
p)-alkylene-arylene-alkyl;
q)-arylene-alkyl;
r)-arylene-aryl;
s)-arylene-heteroaryl;
t)-heteroarylene-aryl;
u)-heteroarylene-heteroaryl;
v)-heteroarylene-heterocyclyl;
w)-arylene-heterocyclyl;
x)-arylene-arylene-alkyl;
y)-$T_1$-alkyl;
z)-$T_1$-aryl;
aa)-$T_1$-alkylene-aryl;
bb)-$T_1$-alkenylene-aryl;
cc)-$T_1$-alkylene-heteroaryl;
dd)-$T_1$-alkenylene-heteroaryl;
ee)-$T_1$-cycloalkylene-aryl;
ff)-$T_1$-cycloalkylene-heteroaryl;
gg)-$T_1$-heterocyclylene-aryl;
hh)-$T_1$-heterocyclylene-heteroaryl;
ii)-$T_1$-arylene-alkyl;
jj)-$T_1$-arylene-alkenyl;
kk)-$T_1$-alkylene-arylene-aryl;
ll)-$T_1$-arylene-$T_2$-aryl;
mm)-$T_1$-arylene-arylene-aryl;
nn)-$T_1$-alkylene-arylene-alkyl;
oo)-alkylene-$T_1$-alkylene-aryl;
pp)-arylene-$T_1$-alkyl;
qq)-arylene-$T_1$-alkylene-aryl;
rr)-$T_1$-alkylene-$T_2$-aryl;
ss)-$T_1$-alkylene-aryl;
tt)-alkylene-$T_1$-heteroaryl;
uu)-alkylene-$T_1$-cycloalkyl;
vv)-alkylene-$T_1$-heterocyclyl;
ww)-alkylene-T-arylene-alkyl;
xx)-alkylene-$T_1$-alkylene-arylene-alkyl;
yy)-alkylene-$T_1$-alkyl;
zz)-alkylene-$T_1$—$R_{20}$;
aaa)-arylene-$T_1$—$R_{20}$;
bbb)-alkylene-cycloalkyl;
ccc)-$T_1$-arylene-$T_2$-alkylene-aryl;
ddd)-$T_1$-arylene-aryl;
eee)-$T_1$-alkylene-cycloalkyl;
fff)-$T_1$-cycloalkyl;
ggg)-$T_1$-heterocyclyl-$T_2$-aryl;
hhh)-$T_1$-alkynyl;
iii)-$T_1$-alkylene-$T_2$-alkyl; or
jjj)-hydrogen;

wherein $T_1$ comprises —$CH_2$—, —O—, —$N(R_{21})$—, —$C(O)$—, —$CON(R_{21})$—, —$N(R_{21})C(O)$—, —$N(R_{21})CON(R_{22})$—, —$N(R_{21})C(O)O$—, —$OC(O)N(R_{21})$—, —$N(R_{21})SO_2$—, —$SO_2N(R_{21})$—, —$C(O)$—$O$—, —$O$—$C(O)$—, —$S$—, —$S(O)$—, —$S(O_2)$—, —$N(R_{21})SO_2N(R_{22})$—,

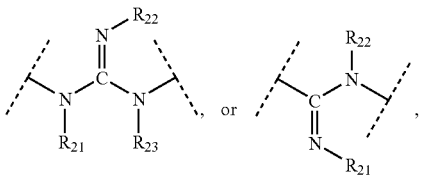 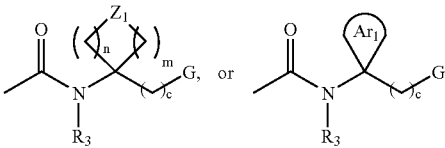

and wherein $R_{20}$, $R_{21}$, $R_{22}$ and $R_{23}$, independently comprise: -hydrogen, -alkyl, -alkenyl, -alkylene-cycloalkyl, -alkynene-heterocyclyl, -aryl, -heteroaryl, -arylene-alkyl, -alkylene-aryl, -alkylene-arylene-alkyl, -alkylene-arylene-aryl, -alkylene-arylene-alkylene-aryl, -alkylene-arylene-O-arylene, or alkylene-arylene-O-alkylene-aryl; and wherein $T_2$ comprises a direct bond, —$CH_2$—, —O—, —$N(R_{24})$—, —$C(O)$—, —$CON(R_{24})$—, —$N(R_{24})C(O)$—, —$N(R_{24})CON(R_{25})$—, —$N(R_{24})C(O)O$—, —$OC(O)N(R_{24})$—, —$N(R_{24})SO_2$—, —$SO_2N(R_{24})$—, —$C(O)$—$O$—, —$O$—$C(O)$—, —$S$—, —$S(O)$—, —$S(O_2)$—, —$N(R_{24})SO_2N(R_{25})$—, wherein $R_{24}$ and $R_{25}$ independently comprise; -hydrogen, -alkyl, -alkenyl, -alkylene-cycloalkyl, alkynene-heterocyclyl, -aryl, -heteroaryl, -arylene-alkyl, -alkylene-aryl, and -alkylene-arylene-alkyl.

In another embodiment, $Ar_2$ comprises a substituted phenyl, 2-naphthyl, 2-pyridyl, 3-isoquinolyl, 2-pyrimidyl or 2-quinazolyl group having 1 to 5 substituents independently comprising:
a)-fluoro;
b)-chloro;
c)-bromo;
d)-iodo;
e)-cyano;
f)-nitro;
g)-perfluoroalkyl;
h)-T1-R20;
i)-alkyl;
j)-aryl;
k)-arylene-alkyl;
l)-T1-alkyl;
m)-T1-alkylene-aryl;
n)-T1-alkylene-arylene-aryl;
o)-T1-alkylene-arylene-alkyl;
p)-arylene-T1-alkyl; or
q)-hydrogen;

wherein $T_1$ comprises —$CH_2$—, —O—, —$N(R_{21})$—, —$CON(R_{21})$—, or —$N(R_{21})C(O)$—; wherein $R_{20}$ and $R_2$, independently comprise: -hydrogen, -alkyl, or -aryl.

K comprises a group of the formula

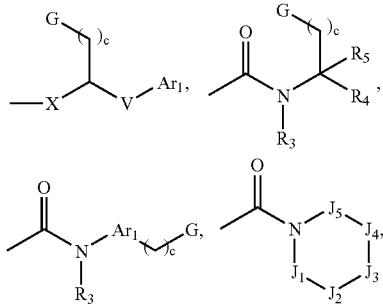

wherein
c is equal to 0, 1, or 2; wherein the values of 0, 1, and 2 comprise a direct bond, —$CH_2$—, and —$CH_2$—$CH_2$—, optionally substituted 1 to 4 times with a substituent group, wherein said substituent group(s) or the term substituted refers to groups comprising: -alkyl, -aryl, -alkylene-aryl, -arylene-alkyl, -alkylene-arylene-alkyl, —O-alkyl, —O-aryl, or -hydroxyl. In an embodiment, c is equal to 0 or 1. In another embodiment, c is equal to 0.

G comprises: -hydrogen, —$CO_2R_1$, —$CH_2OR_1$, —$C(O)$—$R_1$, —$C(R_1)$=$N$—$O$—$R_2$, —$C(O)N(R_1)(R_2)$, —$C(O)$—$NH$—$NH_2$, an acid isostere, or an ester isostere, wherein $R_1$ and $R_2$ independently comprise: -hydrogen, -alkyl, alkoxy, alkylhydroxy, alkyl-N,N'-dialkyl-amino, alkyl-amino-acyl, -aryl, -arylene-alkyl, -alkylene-aryl, -alkylene-arylene-alkyl, or when $R_1$ and $R_2$ are bonded to a nitrogen group in G, $R_1$ and $R_2$ may be taken together to form a ring having the formula —$(CH_2)_m$—$Z_2$—$(CH_2)_n$—, wherein m and n are, independently, 1, 2, 3, or 4; $Z_2$ comprises —$CH_2$—, —$C(O)$—, —O—, —$N(H)$—, —$S$—, —$S(O)$—, —$S(O_2)$—, —$CON(H)$—, —$NHC(O)$—, —$NHC(O)N(H)$—, —$NH(SO_2)$—, —$S(O_2)N(H)$—, —(O)CO—, —$NHS(O_2)NH$—, —$OC(O)$—, —$N(R_{24})$—, —$N(C(O)R_{24})$—, —$N(C(O)NHR_{12})$—, —$N(S(O_2)NHR_{24})$—, —$N(SO_2R_{24})$—, or —$N(C(O)OR_{24})$—; wherein $R_{24}$ comprises hydrogen, aryl, alkyl, or alkylene-aryl. In an embodiment, G comprises: -hydrogen, —$CO_2R_1$, —$CH_2OR_1$, —$C(O)$—$R_1$, —$C(R_1)$=$N$—$O$—$R_2$, or an acid isostere; wherein $R_1$ and $R_2$ independently comprise: -hydrogen, -alkyl, -aryl, -arylene-alkyl, -alkylene-aryl, or -alkylene-arylene-alkyl. In another embodiment, G comprises: -hydrogen or —$CO_2R_1$; wherein $R_1$ comprises: -hydrogen, -alkyl, or -aryl. In another embodiment, G comprises: -hydrogen or —$CO_2H$. In another embodiment, G comprises: —$CO_2R_1$, or an ester isostere, wherein $R_1$ comprises -alkyl, -alkylene-aryl, or -aryl.

$R_3$ comprises: hydrogen, -alkyl, alkylene-aryl, -aryl, or -alkylene-cycloalkyl. In an embodiment, $R_3$ comprises: hydrogen. In another embodiment, $R_3$ comprises: -alkyl, alkylene-aryl, or -alkylene-cycloalkyl.

$R_4$ comprises: hydrogen, -alkyl, -alkylene-cycloalkyl, or -alkylene-heterocyclyl, -alkylene. $R_5$ comprises: hydrogen, -alkyl, -alkylene-cycloalkyl, -alkylene-heterocyclyl, -alkoxy, alkylhydroxy, alkyl-N,N'-dialkyl-amino, or -alkyl-amino-acyl. In an embodiment, $R_4$ comprises: hydrogen, and $R_5$ comprises: alkyl, -alkoxy, alkylhydroxy, or -alkylene-cycloalkyl.

$J_1$, $J_2$, $J_3$, $J_4$, $J_5$ independently comprise —$C(R_{25})(R_{26})$— or a direct bond, wherein $R_{25}$ and $R_{26}$ independently comprise hydrogen, -alkyl, -aryl, -alkylene-aryl, alkoxy, alkylhydroxy, alkylene-O-alkyl, alkylene-O-alkylene-aryl, —$CO_2H$, -alkylene-$CO_2H$, —$CO_2$-alkyl, or -alkylene-$CO_2$-alkyl, -acid isostere, or -ester isostere, and wherein the ring comprising nitrogen and $J_1$ contains at least four carbon atoms and at least one of $J_1$ through $J_5$ is substituted with —$CO_2H$, -alkylene-$CO_2H$, —$CO_2$-alkyl, or -alkylene-$CO_2$-alkyl, -acid isostere, or -ester isostere.

$Z_1$ comprises —$CH_2$—, —C(O)—, —O—, —N(H)—, —S—, —S(O)—, —$S(O_2)$—, —CON(H)—, —NHC(O)—, —NHC(O)N(H)—, —$NH(SO_2)$—, —$S(O_2)N(H)$—, —(O)CO—, —$NHS(O_2)NH$—, —OC(O)—, —$N(R_6)$—, —$N(C(O)R_6)$—, —$N(C(O)NHR_6)$—, —$N(S(O_2)NHR_6)$—, —$N(SO_2R_6)$—, or —$N(C(O)OR_6)$—; wherein $R_6$ comprises: -hydrogen, alkyl, aryl, or alkylene-aryl. In an embodiment, $Z_1$ comprises —$CH_2$—, —O—, —N(H)—, —S—, —$S(O_2)$—, —$N(R_6)$—, or —$N(C(O)OR_6)$—, wherein $R_6$ comprises alkyl or alkylene-aryl.

V comprises: —$(CH_2)_b$—S—$(CH_2)_a$—, —$(CH_2)_b$—S—, —S—$(CH_2)_a$—, —$(CH_2)_b$—$S(O_2)$—$(CH_2)_a$—, —$(CH_2)_b$—$S(O_2)$—, —$S(O_2)$—$(CH_2)_a$—, —$(CH_2)_b$—O—$(CH_2)_a$—, —$(CH_2)_b$—$N(R_7)$—$(CH_2)_a$—, —$(CH_2)_b$—O—, —$(CH_2)_b$—$N(R_7)$, —$(CH_2)_a$—, or a direct bond; in which a is equal to 0, 1, or 2, b is equal to 1 or 2, and $R_7$ comprises: -hydrogen, -alkyl, -aryl, -arylene-alkyl, -alkylene-aryl, or -alkylene-arylene-alkyl; wherein the values of 0, 1, and 2 comprise a direct bond, —$CH_2$—, and —$CH_2$—$CH_2$—, optionally substituted 1 to 4 times with a substituent group, wherein said substituent group(s) or the term substituted refers to groups comprising: -alkyl, -aryl, -alkylene-aryl, -arylene-alkyl, -alkylene-arylene-alkyl, —O-alkyl, —O-aryl, or -hydroxyl. In an embodiment, V comprises: —$(CH_2)_b$—O—$(CH_2)_a$—, —$(CH_2)_b$—$N(R_7)$—$(CH_2)_a$—, —$(CH_2)_b$—O—, —$(CH_2)_b$—$N(R_7)$, —$(CH_2)_2$—, or a direct bond; in which a is equal to 0, 1, or 2, b is equal to 1 or 2, and $R_7$ comprises: -hydrogen, -alkyl, -aryl, -arylene-alkyl, -alkylene-aryl, or -alkylene-arylene-alkyl; wherein the values of 0, 1, and 2 comprise a direct bond, —$CH_2$—, and —$CH_2$—$CH_2$—, optionally substituted 1 to 4 times with a substituent group, wherein said substituent group(s) or the term substituted refers to groups comprising: -alkyl, -aryl, -alkylene-aryl, -arylene-alkyl, -alkylene-arylene-alkyl, —O-alkyl, —O-aryl, or -hydroxyl. In another embodiment, V comprises: —$(CH_2)_a$—, —$(CH_2)_b$—O—$(CH_2)_a$—, or a direct bond, wherein a is equal to 1 or 2, and b is equal to 1. In another embodiment, V comprises: —$(CH_2)_a$— or a direct bond, wherein a is equal to 1.

X comprises: —$N(R_8)$—, —$CON(R_8)$—, —$N(R_8)CO$—, —$N(R_8)CON(R_9)$—, —$OC(O)N(R_8)$—, —$SO_2N(R_8)$—, or —$N(R_8)SO_2N(R_9)$—; wherein $R_8$ and $R_9$ independently comprise: -hydrogen, -alkyl, -aryl, -arylene-alkyl, -alkylene-aryl, -alkylene-arylene-alkyl, -alkylene-cycloalkylene-C(O)-alkylene-aryl, -alkylene-heterocyclylene-C(O)-alkylene-aryl, -alkylene-C(H)($R_{10}$)($R_{11}$), -alkylene-N-($R_{10}$)($R_{11}$), or -alkylene-cycloalkyl,
  wherein $R_{10}$ comprises H, alkyl, alkylene-aryl, alkylene-heteroaryl, aryl, or heteroaryl, and $R_{11}$ comprises H, -alkyl, -alkylene-aryl, -alkylene-heteroaryl, -aryl, -heteroaryl, —C(O)—O-alkyl, —C(O)—O-alkylene-aryl, —C(O)—O-alkylene-heteroaryl, —C(O)-alkyl, —C(O)-alkylene-aryl, —C(O)-alkylene-heteroaryl, —$S(O)_2$-alkyl, —$S(O)_2$-aryl, —$S(O)_2$-heteroaryl, —$S(O)_2$-alkylene-aryl, —$S(O)_2$-alkylene-heteroaryl, —$S(O)_2$—NH-alkyl, —$S(O)_2$—NH-alkylene-aryl, —$S(O)_2$—NH-alkylene-heteroaryl, —$S(O)_2$—NH-aryl, or —$S(O)_2$—NH-heteroaryl;
  $R_{10}$ and $R_{11}$ may be taken together to form a ring having the formula —$(CH_2)_m$-$Z_2$-$(CH_2)_n$— bonded to the nitrogen or carbon atom to which $R_{10}$ and $R_{11}$ are attached, wherein m and n are, independently, 1, 2, 3, or 4; $Z_2$ independently comprises —$CH_2$—, —C(O)—, —O—, —N(H)—, —S—, —S(O)—, —$S(O_2)$—, —CON(H)—, —NHC(O)—, —NHC(O)N(H)—, —$NH(SO_2)$—, —$S(O_2)N(H)$—, —(O)CO—, —$NHS(O_2)NH$—, —OC(O)—, —$N(R_{12})$—, —$N(C(O)R_{12})$—, —$N(C(O)NHR_{12})$—, —$N(S(O_2)NHR_{12})$—, —$N(SO_2R_{12})$—, or —$N(C(O)OR_{12})$—; or
  $R_{10}$ and $R_{11}$ may be taken together, with the nitrogen or carbon atom to which they are attached, to form a heterocyclyl or heteroaryl ring.
  $R_{12}$ comprises hydrogen, aryl, alkyl, or alkylene-aryl;

In an embodiment, X comprises: —$N(R_8)$—, —$CON(R_8)$—, —$N(R_8)CO$—, or —$N(R_8)CON(R_9)$—, wherein $R_8$ and $R_9$ independently comprise: -hydrogen, -alkyl, -aryl, -arylene-alkyl, -alkylene-aryl, or -alkylene-arylene-alkyl. In another embodiment, X comprises: —$N(R_8)$—, —$CON(R_8)$—, or —$N(R_8)CO$—, wherein $R_8$ comprises: -hydrogen, -alkyl, -aryl, -arylene-alkyl, -alkylene-aryl, or -alkylene-arylene-alkyl. In another embodiment, X comprises —$CON(R_8)$—, wherein $R_8$ comprises -hydrogen, -alkyl, -aryl, -arylene-alkyl, -alkylene-aryl, -alkylene-arylene-alkyl, or -alkylene-cycloalkyl, $Ar_1$ comprises an aryl, heteroaryl, fused cycloalkylaryl, fused cycloalkylheteroaryl, fused heterocyclylaryl, or fused heterocyclylheteroaryl group optionally substituted 1 to 7 times. In an embodiment, $Ar_1$ comprises a mono- or bicyclic aryl or heteroaryl group optionally substituted 1 to 7 times. In another embodiment, $Ar_1$ comprises a phenyl, pyridyl, indolyl, naphthyl, thiophenyl, thiazole, or benzothiazole group optionally substituted 1 to 7 times. In another embodiment, $Ar_1$ comprises a phenyl group having 1 to 5 substituents, wherein the substituents independently comprise:
  a)-fluoro;
  b)-chloro;
  c)-bromo;
  d)-iodo;
  e)-cyano;
  f)-nitro;
  g)-perfluoroalkyl;
  h)-$D_1$—$R_{14}$;
  i)-alkyl;
  j)-aryl;
  k)-heteroaryl;
  l)-heterocyclyl;
  m)-cycloalkyl;
  n)-alkylene-aryl;
  o)-alkylene-heteroaryl;
  p)-alkylene-arylene-$D_1$—$R_{14}$;
  q)-alkylene-heteroarylene-$D_1$—$R_{14}$;
  r)-alkylene-arylene-aryl;
  s)-alkylene-heteroarylene-aryl;
  t)-alkylene-arylene-heteroaryl;
  u)-alkylene-arylene-arylene-$D_1$—$R_{14}$;
  v)-alkylene-arylene-alkyl;
  w)-alkylene-heteroarylene-alkyl;
  x)y)-arylene-cycloalkyl;
  z)-heteroarylene-alkyl;
  aa)-arylene-arylene-alkyl;
  bb)-$D_1$-alkyl;
  cc)-$D_1$-aryl;
  dd)-$D_1$-heteroaryl;
  ee)-$D_1$-arylene-$D_2$—$R_{14}$;
  ff)-$D_1$-heteroarylene-$D_2$—$R_{14}$;
  gg)-$D_1$-alkylene-heteroaryl;
  hh)-$D_1$-alkylene-aryl;
  ii)-$D_1$-alkylene-arylene-$D_2$—$R_{14}$
  jj)-$D_1$-alkylene-heteroarylene-$D_2$—$R_{14}$
  kk)-$D_1$-arylene-alkyl;
  ll)-$D_1$-heteroarylene-alkyl;
  mm)-$D_1$-alkylene-arylene-aryl;
  nn)-$D_1$-alkylene-heteroarylene-aryl;
  oo)-$D_1$-arylene-arylene-aryl;

pp)-D₁-alkylene-arylene-alkyl;
qq)-D₁-alkylene-heteroarylene-alky
ss)-alkylene-D₁-alkylene-aryl;
tt)-alkylene-D₁-alkylene-arylene-D₂-R₁₄
uu)-arylene-D₁-alkyl;
vv)-arylene-D₁-cycloalkyl;
ww)-arylene-D₁-heterocyclyl;
xx)-alkylene-D₁-aryl;
yy)-alkylene-D₁-heteroaryl;
zz)-alkylene-D₁-arylene-D₂—R₁₄
aaa)-alkylene-D₁-heteroarylene-D₂—R₁₄
bbb)-alkylene-D₁-heteroaryl;
ccc)-alkylene-D₁-cycloalkyl;
ddd)-alkylene-D₁-heterocyclyl;
eee)-alkylene-D₁-arylene-alkyl;
fff)-alkylene-D₁-heteroarylene-alkyl;
ggg)-alkylene-D₁-alkylene-arylene-alkyl;
hh)-alkylene-D₁-alkylene-heteroarylene-alkyl;
iii)-alkylene-D₁-alkyl;
jjj)-alkylene-D₁-R₁₄;
kkk)-arylene-D₁—R₁₄;
lll)-heteroarylene-D₁—R₁₄;
mmm)-D₁-alkynyl;
nnn)-D₁-alkylene-cycloalkyl;
ooo)-arylene-D₁-arylene-D₂—R₁₄ or
ppp)-hydrogen;

wherein D₁ comprises —CH₂—, -alkylene-, -alkenylene-, -alkylene-S—, —S-alkylene-, -alkylene-O—, —O-alkylene-, -alkylene-S(O)₂—, —S(O)₂-alkylene, —O—, —N(R₁₅)—, —C(O)—, —CON(R₁₅)—, —N(R₁₅)C(O)—, —N(R₁₅)CON(R₁₆)—, —N(R₁₅)C(O)O—, —OC(O)N(R₁₅)—, —N(R₁₅)SO₂—, —SO₂N(R₁₅)—, —C(O)—O—, —O—C(O)—, —S—, —S(O)—, —S(O)₂—, —N(R₁₅)SO₂N(R₁₆)—,

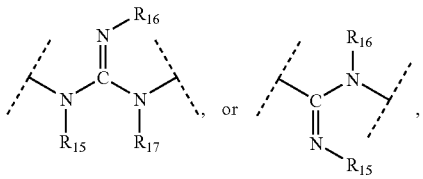

and wherein R₁₄, R₁₅, R₁₆, and R₁₇ independently comprise: - hydrogen, -alkyl, -aryl, -heteroaryl, -arylene-alkyl, -heteroarylene-alkyl, -alkylene-aryl, -alkylene-heteroaryl, -alkylene-arylene-alkyl, or -alkylene-heteroarylene-alkyl.

D₂ comprises —CH₂—, -alkylene-, -alkenylene-, -alkylene-S—, —S-alkylene-, -alkylene-O—, —O-alkylene-, -alkylene-S(O)₂—, —S(O)₂-alkylene, —O—, —N(R₁₈)—, —C(O)—, —CON(R₁₈)—, —N(R₁₈)C(O)—, —N(R₁₈)CON(R₁₉)—, —N(R₁₈)C(O)O—, —OC(O)N(R₁₈)—, —N(R₁₈)SO₂—, —SO₂N(R₁₈)—, —C(O)—O—, —O—C(O)—, —S—, —S(O)—, —S(O)₂—, —N(R₁₈)SO₂N(R₁₉)—, and wherein R₁₈ and R₁₉ independently comprise: -hydrogen, -alkyl, -aryl, -arylene-alkyl, -alkylene-aryl, or -alkylene-arylene-alkyl.

In another embodiment, Ar₁ comprises a mono-substituted phenyl group wherein the substituent comprises: -aryl, -arylene-alkyl, —D₁-aryl, —D₁-alkylene-arylene-alkyl, or -arylene-D₁-alkyl; wherein D₁ comprises —O—, —N(R₁₅)—, —CON(R₁₅)—, or —N(R₁₅)C(O)—, and wherein R₁₅ comprises: -hydrogen; -alkyl; or -aryl.

In another embodiment, Ar₁ comprises a phenyl group substituted with at least one of the following substituents:
—D₁—R14;
-alkyl;
-aryl;
-heteroaryl;
-heterocyclyl;
-arylene-alkyl;
—D1-alkyl;
—D1-aryl;
—D1-heteroaryl;
—D1-arylene-D2—R14;
—D1-alkylene-heteroaryl;
—D1-alkylene-aryl;
—D1-alkylene-arylene-D₂—R₁₄
-arylene-D1-alkyl;
-alkylene-D1-alkyl;
-alkylene-D1—R14;
-arylene-D1—R14;
—D1-alkynyl;
—D1-alkylene-cycloalkyl;
-arylene-D, -arylene-D₂—R₁₄ wherein
D₁ and D₂ independently comprise: —O— or —S(O₂)—, and
R₁₄ comprises hydrogen, -alkyl, -aryl, -arylene-aryl, -alkylene-aryl.

In another embodiment, Ar₁ comprises an unsubstituted phenyl or biphenyl group.

The alkyl, aryl, heteroaryl, alkylene, and arylene groups in Ar₁, Ar₂, R₁ through R₂₆ may be optionally substituted 1 to 4 times with a substituent group, wherein said substituent group(s) or the term substituted refers to groups comprising:
a)-hydrogen;
b)-fluoro;
c)-chloro;
d)-bromo;
e)-iodo;
f)-cyano;
g)-nitro;
h)-perfluoroalkyl;
i)-Q-perfluoroalkyl
j)-Q-R27;
k)-Q-alkyl;
l)-Q-aryl;
m)-Q-alkylene-aryl;
n)-Q-alkylene-NR₂₇R₂₈; or
o)-Q-alkyl-W—R₂₈;

wherein Q and W independently comprise: —CH₂—, —O—, —N(R₂₉)—, —C(O)—, —CON(R₂₉)—, —N(R₂₉)C(O)—, —N(R₂₉)CON(R₃₀)—, —N(R₂₉)C(O)O—, —OC(O)N(R₂₉)—, —N(R₂₉)SO₂—, —SO₂N(R₂₉)—, —C(O)—O—, —O—C(O)—, or —N(R₂₉)SO₂N(R₃₀)—, wherein R₂₇, R₂₈, R₂₉, and R₃₀ independently comprise: -hydrogen, -alkyl, -aryl, -arylene-alkyl, -alkylene-aryl, or -alkylene-arylene-alkyl.

In another embodiment, the compounds are represented by Formula (I), in which c is equal to 0; G comprises: -hydrogen or —CO₂H; V comprises: —CH₂— or a direct bond; X comprises: —CON(R₈)—, or —N(R₈)CO— wherein R₈ comprises: -hydrogen; Ar₁ comprises a mono-substituted phenyl group wherein the substituent comprises: -aryl, -arylene-alkyl, —D₁-aryl —D₁-alkylene-arylene-alkyl, or -arylene-D₁-alkyl, wherein D₁ comprises —O—, or —N(R$_{15}$)—, wherein R$_{15}$ comprises: -hydrogen, -alkyl, or -aryl; and Ar$_2$ comprises a substituted phenyl, 2-naphthyl, 2-pyridyl, 3-isoquinolyl, 2-pyrimidyl or 2-quinazolyl group having 1 to 5 substituents independently comprising: -hydrogen, -fluoro, -chloro, -bromo, iodo, -cyano, -nitro, -perfluoroalkyl, —T$_1$—R$_{14}$, -alkyl, -aryl, -arylene-alkyl, —T$_1$-alkyl, —T$_1$-alkylene-aryl, —T$_1$-alkylene-arylene-aryl, —T$_1$-alkylene-arylene-alkyl, or -arylene-T$_1$-alkyl; wherein T$_1$ comprises —CH$_2$—, —O—, —N(R$_{21}$)—, —CON(R$_{21}$)—, or —N(R$_{21}$)C(O)—; wherein R$_{21}$ comprises: -hydrogen, -alkyl, or -aryl. The alkyl, aryl, alkylene, and arylene groups in Ar$_1$, and Ar$_2$ may be optionally substituted 1 to 4 times with a substituent group, wherein said substituent group(s) or the term substituted refers to groups comprising: -hydrogen, -fluoro, -chloro, -bromo, iodo, -cyano, -nitro, or -perfluoroalkyl.

In another embodiment, the instant invention relates to a compound of Formula (X),

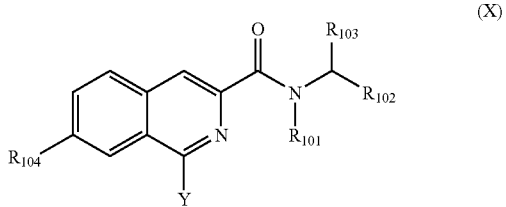

wherein

R$_{101}$, is selected from the group consisting of —H, or —CH$_2$-thienyl wherein the thienyl group in —CH$_2$-thienyl is optionally substituted with —Br or —CH$_3$;

R$_{102}$ is selected from the group consisting of —C(O)OH, —C(O)OCH$_3$, —C(O)O-t-butyl, —C(O)NH—OCH$_2$-phenyl, —C(O)NHOH, and —C(O)NHSO$_2$CH$_3$;

R$_{103}$ is selected from the group consisting of —H, —CH$_2$-thienyl, —CH$_2$-phenyl, —CH$_2$-furanyl, -thienyl, and benzothienyl wherein each of the above possibilities for R$_{103}$ except —H are optionally substituted with one or more members selected from group consisting of —H, —CH$_3$, —CF$_3$, —Cl, —Br, —F, —C(O)CH$_3$, —CH$_2$CH$_3$, —CH═CH$_2$, —CH$_2$OH,

—CH(CH$_3$)$_2$,

—CH$_2$CH$_2$CH$_3$,

-propenyl, -3,3-dimethyl-butenyl, -isopropenyl, -phenyl, -phenylene-methyl, -phenylene-propyl, -phenylene-trifluoromethyl, -phenylene-chloride, -cyclopentyl, -cyclopentenyl, and -furanyl;

R$_{104}$ is selected from the group consisting of —O-cyclohexylene-ethyl, —O-cyclohexylene-t-butyl, —O-cyclohexylene-1-propyl, —O-phenylene-t-butyl, -phenylene-t-butyl, and —C(O)-phenylene-t-butyl;

and Y is selected from the group consisting of —H, -methylene-cyclopentyl, -amino-cyclohexyl, -methylene-thienylene-methyl, methylene-thienylene-bromide, and tetrahydropyranyl;

or a pharmaceutically acceptable salt, ester, or prodrug thereof.

In another embodiment, the instant invention relates to a compound of Formula (X),

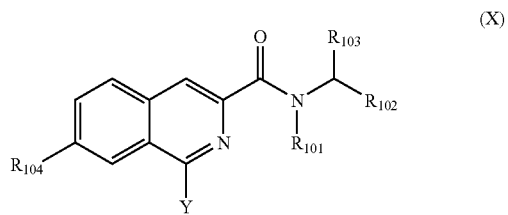

wherein

R$_{101}$ is selected from the group consisting of —H, or —CH$_2$-thienyl wherein the thienyl group in —CH$_2$-thienyl is optionally substituted with —Br or —CH$_3$;

R$_{102}$ is selected from the group consisting of —C(O)OH, —C(O)OCH$_3$, —C(O)O-t-butyl, —C(O)NH—OCH$_2$-phenyl, —C(O)NHOH, and —C(O)NHSO$_2$CH$_3$;

R$_{103}$ is selected from the group consisting of —H, —CH$_2$-thienyl, —CH$_2$-phenyl, —CH$_2$-furanyl, thienyl, and benzothienyl wherein each of the above possibilities for R$_{103}$ except —H are optionally substituted with one or more members selected from group consisting of —H, —CH$_3$, —CF$_3$, —Cl, —Br, —F, —C(O)CH$_3$, —CH$_2$CH$_3$, —CH═CH$_2$, —CH$_2$OH, —CH(CH$_3$)$_2$, —CH$_2$CH$_2$CH$_3$, -propenyl, -3,3-dimethyl-butenyl, -isopropenyl, -phenyl, -phenylene-methyl, phenylene-trifluoromethyl, -phenylene-chloride, cyclopentyl, cyclopentenyl, and furanyl;

R$_{104}$ is selected from the group consisting of —O-cyclohexylene-ethyl, —O-cyclohexylene-t-butyl, —O-cyclohexylene-i-propyl, —O-phenylene-t-butyl, -phenylene-t-butyl, and —C(O)-phenylene-t-butyl;

and Y is selected from the group consisting of —H, -methylene-cyclopentyl, -amino-cyclohexyl, -methylene-thienylene-methyl, methylene-thienylene-bromide, and tetrahydropyranyl;

or a pharmaceutically acceptable salt, ester, or prodrug thereof.

The instant invention also relates to a compound of Formula (X),

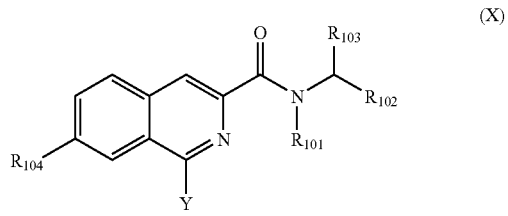

wherein R$_{101}$ is selected from the group consisting of —H, or —CH$_2$-thienyl wherein the thienyl group in —CH$_2$-thienyl is optionally substituted with —Br or —CH$_3$;

R$_{102}$ is selected from the group consisting of —C(O)OH, —C(O)OCH$_3$, —C(O)O-t-butyl, —C(O)NH—OCH$_2$-phenyl, —C(O)NHOH, and —C(O)NHSO$_2$CH$_3$;

R$_{103}$ is selected from the group consisting of —H, —CH$_2$-thienyl, —CH$_2$-phenyl, —CH$_2$-furanyl, thienyl, and benzothienyl wherein each of the above possibilities for R$_{103}$ except —H are optionally substituted with one or more members selected from group consisting of —H, —CH$_3$, —CF$_3$, —Cl, —Br, —F, —C(O)CH$_3$, —CH$_2$CH$_3$, —CH=CH$_2$ —CH$_2$OH, —CH(CH$_3$)$_2$, —CH$_2$CH$_2$CH$_3$,

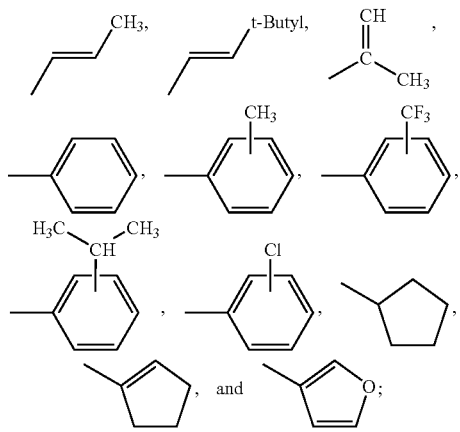

R$_{104}$ is selected from the group consisting of

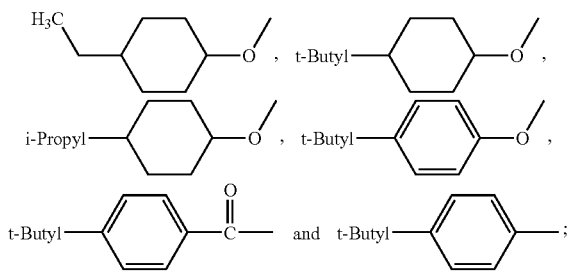

and Y is selected from the group consisting of H,

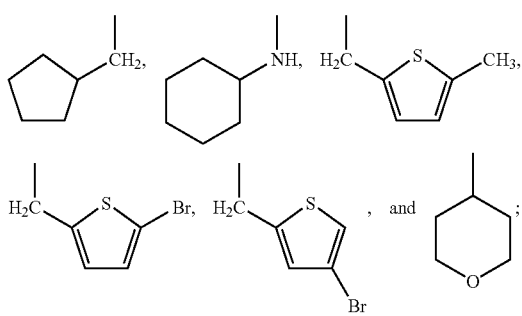

or a pharmaceutically acceptable salt, ester, or prodrug thereof.

Another embodiment is a compound wherein R$_{104}$ is

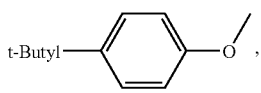

and wherein R$_{103}$ is optionally substituted —CH$_2$-2-yl-thienyl or optionally substituted —CH$_2$-phenyl. Moreover, another embodiment relates to compounds wherein R$_{101}$ is —H and compounds wherein Y is selected from the group consisting of

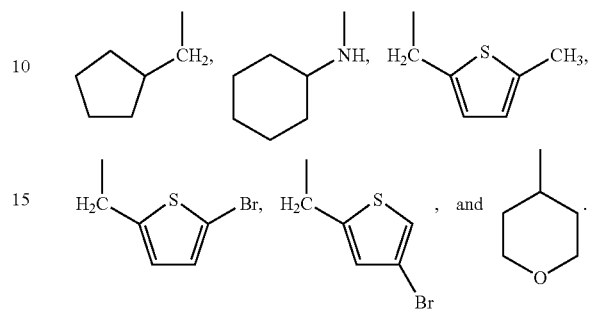

Another embodiment for Y is when it is -methylene-cyclopentyl.

In another embodiment, the instant invention relates to a pharmaceutical composition comprising a therapeutically effective amount of the compound of Formula (X)

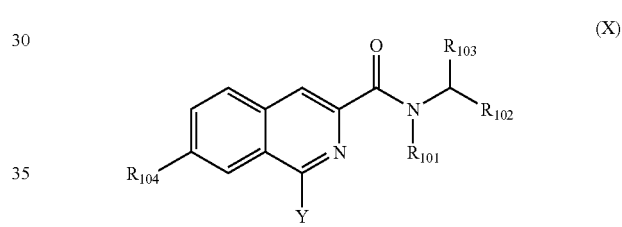

wherein R$_{101}$ is selected from the group consisting of —H, or —CH$_2$-thienyl wherein the thienyl group in —CH$_2$-thienyl is optionally substituted with —Br or —CH$_3$;

R$_{102}$ is selected from the group consisting of —C(O)OH, —C(O)OCH$_3$, —C(O)O-t-butyl, —C(O)NH—OCH$_2$-phenyl, —C(O)NHOH, and —C(O)NHSO$_2$CH$_3$;

R$_{103}$ is selected from the group consisting of —H, —CH$_2$-thienyl, —CH$_2$-phenyl, —CH$_2$-furanyl, thienyl, and benzothienyl wherein each of the above possibilities for R$_{103}$ except —H are optionally substituted with one or more members selected from group consisting of —H, —CH$_3$, —CF$_3$, —Cl, —Br, —F, —C(O)CH$_3$, —CH$_2$CH$_3$, —CH=CH$_2$, —CH$_2$OH, —CH(CH$_3$)$_2$, —CH$_2$CH$_2$CH$_3$,

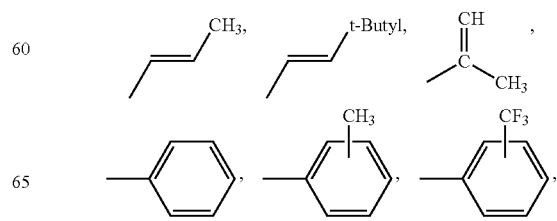

-continued

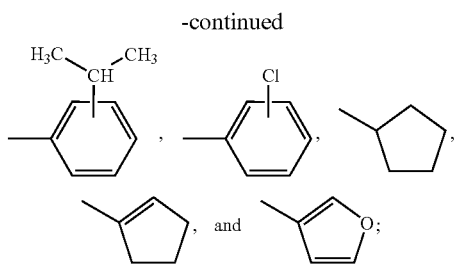

$R_{104}$ is selected from the group consisting of

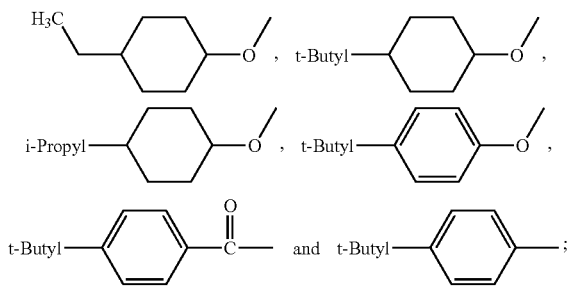

and Y is selected from the group consisting of H,

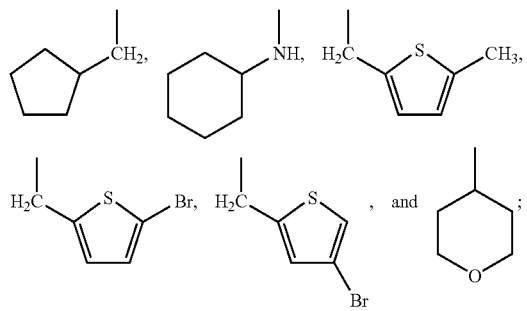

or a pharmaceutically acceptable salt, ester, or prodrug thereof, and one or more pharmaceutically acceptable carriers, excipients, or diluents.

Other embodiments are pharmaceutical compositions wherein $R_{104}$ is

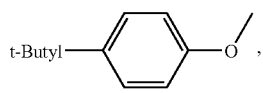

and wherein $R_{103}$ is optionally substituted —$CH_2$-2-yl-thienyl or optionally substituted —$CH_2$-phenyl.

Another embodiment is when $R_{103}$ is optionally substituted —$CH_2$-2-yl-thienyl.

Other embodiments are when the pharmaceutical composition has a compound of formula (X) as above when $R_{101}$, is H, or when Y is selected from the group consisting of

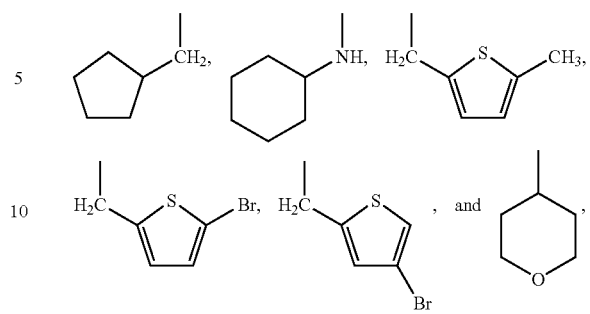

and more particularly when Y is -methylene-cyclopentyl.

The present invention also relates to a method for the inhibition of the normal biological function of factor IX comprising administering to a subject a compound of Formula (X)

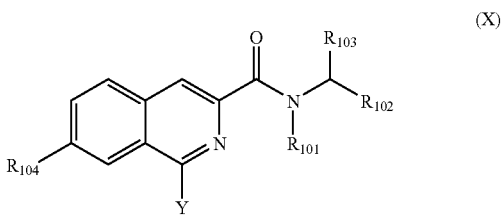

wherein $R_{101}$, is selected from the group consisting of —H, or —$CH_2$-thienyl wherein the thienyl group in —$CH_2$-thienyl is optionally substituted with —Br or —$CH_3$;

$R_{102}$ is selected from the group consisting of —C(O)OH, —C(O)OCH$_3$, —C(O)O-t-butyl, —C(O)NH—OCH$_2$-phenyl, —C(O)NHOH, and —C(O)NHSO$_2$CH$_3$;

$R_{103}$ is selected from the group consisting of —H, —CH$_2$-thienyl, —CH$_2$-phenyl, —CH$_2$-furanyl, thienyl, and benzothienyl wherein each of the above possibilities for $R_{103}$ except —H are optionally substituted with one or more members selected from group consisting of —H, —CH$_3$, —CF$_3$, —Cl, —Br, —F, —C(O)CH$_3$, —CH$_2$CH$_3$, —CH=CH$_2$, —CH$_2$OH, —CH(CH$_3$)$_2$, —CH$_2$CH$_2$CH$_3$,

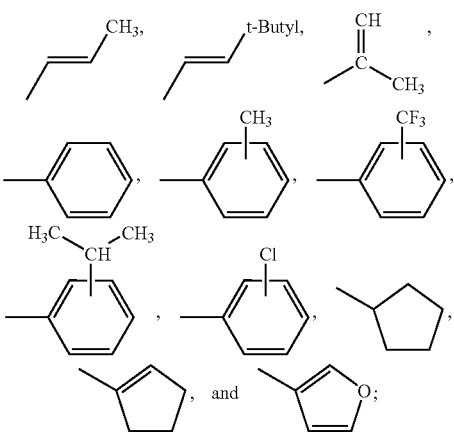

$R_{104}$ is selected from the group consisting of

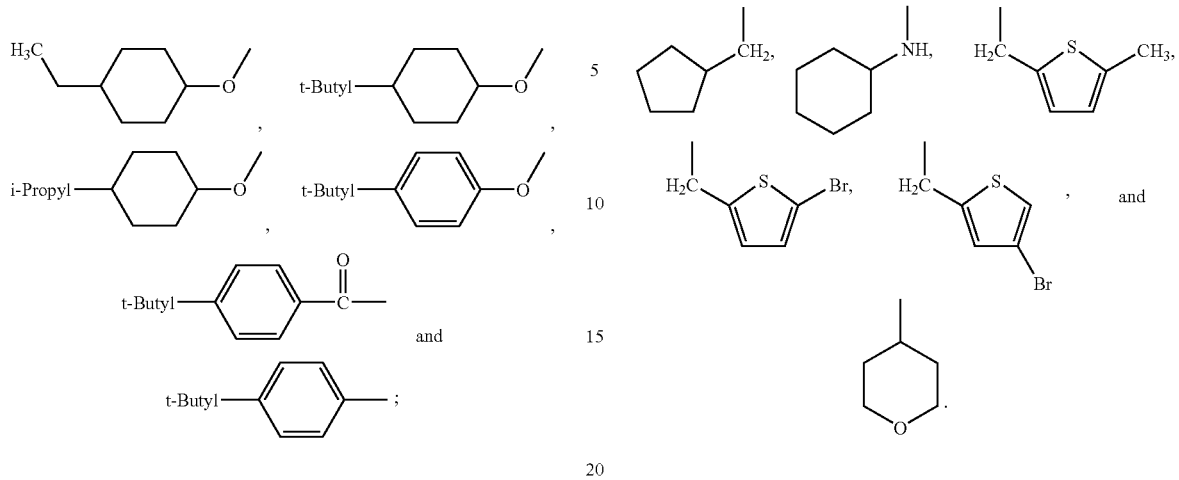

and Y is selected from the group consisting of H,

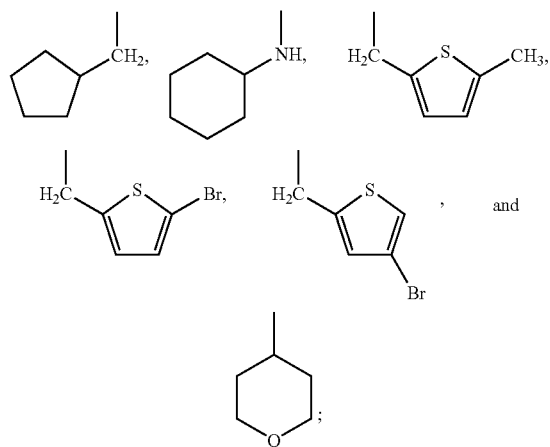

or a pharmaceutically acceptable salt, ester, or prodrug thereof.

In another embodiment, the instant invention relates to a method for the inhibition of the normal biological function of factor IX, wherein the compound of formula (X) is delivered as part of a pharmaceutical composition.

In another embodiment, the method for the inhibition of the normal biological function of factor IX uses a compound of formula (X) wherein $R_{104}$ is

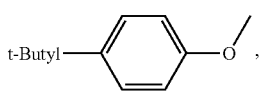

or, wherein $R_{103}$ is optionally substituted —$CH_2$-2-yl-thienyl or optionally substituted —$CH_2$-phenyl.

Another embodiment is the method for the inhibition of the normal biological function of factor IX wherein a compound of formula (X) is administered and $R_{101}$ is —H or wherein Y is selected from the group consisting of

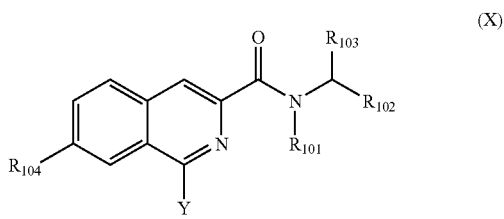

Another method for the inhibition of the normal biological function of factor IX is administering a compound when Y is -methylene-cyclopentyl.

In another embodiment, the instant invention comprises a method of treating stroke, myocardial infarction, an aneurysm, or thrombosis comprising administering to a subject a compound of Formula (X)

(X)

wherein $R_{101}$ is selected from the group consisting of —H, or —$CH_2$-thienyl wherein the thienyl group in —$CH_2$-thienyl is optionally substituted with —Br or —$CH_3$;

$R_{102}$ is selected from the group consisting of —C(O)OH, —C(O)OCH$_3$, —C(O)O-t-butyl, —C(O)NH—OCH$_2$-phenyl, —C(O)NHOH, and —C(O)NHSO$_2$CH$_3$;

$R_{103}$ is selected from the group consisting of —H, —CH$_2$-thienyl, —CH$_2$-phenyl, —CH$_2$-furanyl, thienyl, and benzothienyl wherein each of the above possibilities for $R_{103}$ except —H are optionally substituted with one or more members selected from group consisting of —H, —CH$_3$, —CF$_3$, —Cl, —Br, —F, —C(O)CH$_3$, —CH$_2$CH$_3$, —CH=CH$_2$, —CH$_2$OH, —CH(CH$_3$)$_2$, —CH$_2$CH$_2$CH$_3$,

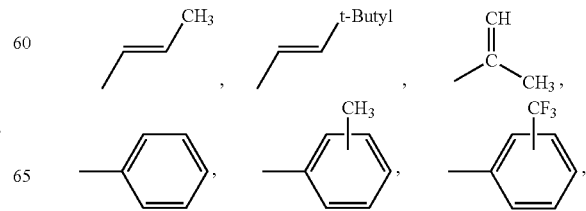

-continued

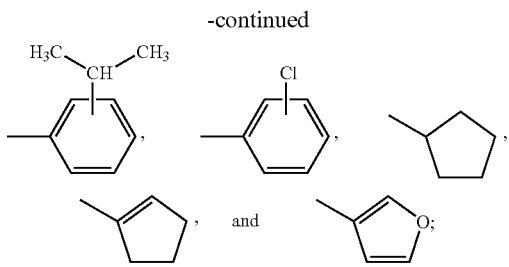

$R_{104}$ is selected from the group consisting of

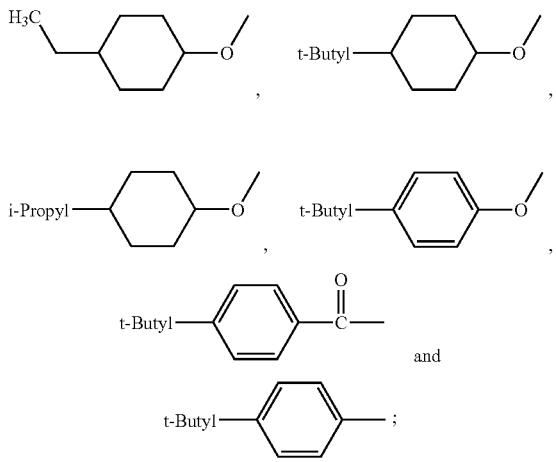

and Y is selected from the group consisting of H,

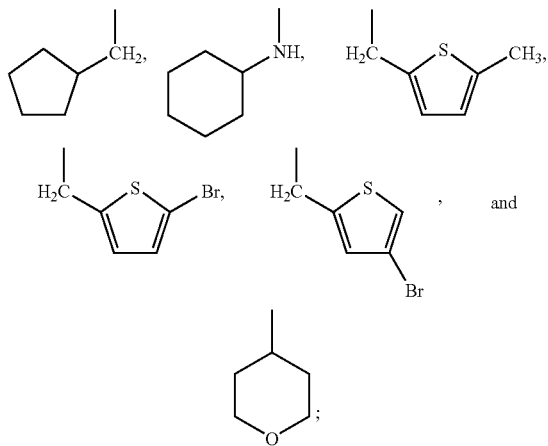

or a pharmaceutically acceptable salt, ester, or prodrug thereof.

In another embodiment, the method of treating the above-enumerated diseases comprises administering a compound of formula (X) as part of a pharmaceutical composition.

In another embodiment, the method of treating the above-enumerated diseases comprises administering a compound of formula (X) wherein $R_{104}$ is

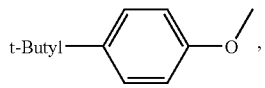

or wherein $R_{103}$ is optionally substituted —$CH_{2-2}$-yl-thienyl or optionally substituted —$CH_2$-phenyl. The method according to claim 30, wherein $R_{101}$ is —H.

One method of treating the above-enumerated diseases uses a compound that is selected from the group consisting of 2(S)-{[7-(4-tert-Butyl-phenoxy)-1-cyclopentylmethyl-isoquinoline-3-carbonyl]-amino}-3-(5-phenyl-thiophen-2-yl)-propionic acid, 2(S)-{[7-(4-tert-Butyl-phenoxy)-1-cyclopentylmethyl-isoquinoline-3-carbonyl]-amino}-3-[5-(4-trifluoromethyl-phenyl)-thiophen-2-yl]-propionic acid, 2(S)-{[7-(4-tert-Butyl-phenoxy)-1-cyclopentylmethyl-isoquinoline-3-carbonyl]-amino}-3-(5-cyclopent-1-enyl-thiophen-2-yl)-propionic acid methyl ester, 2(S)-{[7-(4-tert-Butyl-phenoxy)-1-cyclopentylmethyl-isoquinoline-3-carbonyl]-amino}-3-(5-cyclopent-1-enyl-thiophen-2-yl)-propionic acid, 2(S)-{[7-(4-tert-Butyl-phenoxy)-1-cyclopentylmethyl-isoquinoline-3-carbonyl]-amino}-3-(5-cyclopentyl-thiophen-2-yl)-propionic acid methyl ester, 2(S)-{[7-(4-tert-Butyl-phenoxy)-1-cyclopentylmethyl-isoquinoline-3-carbonyl]-amino}-3-(5-cyclopentyl-thiophen-2-yl)-propionic acid, 2(S)-{[7-(4-tert-Butyl-phenoxy)-1-cyclopentylmethyl-isoquinoline-3-carbonyl]-amino}-3-(5-furan-3-yl-thiophen-2-yl)-propionic acid, 2(S)-{[7-(4-tert-Butyl-phenoxy)-1-cyclopentylmethyl-isoquinoline-3-carbonyl]-amino}-3-[5-(4-isopropyl-phenyl)-thiophen-2-yl]-propionic acid, 2(S)-{[7-(4-tert-Butyl-phenoxy)-1-cyclopentylmethyl-isoquinoline-3-carbonyl]-amino}-3-(5-vinyl-thiophen-2-yl)-propionic acid, 2(S)-{[7-(4-tert-Butyl-phenoxy)-1-cyclopentylmethyl-isoquinoline-3-carbonyl]-amino}-3-(5-p-tolyl-thiophen-2-yl)-propionic acid, 2(S)-{[7-(4-tert-Butyl-phenoxy)-1-cyclopentylmethyl-isoquinoline-3-carbonyl]-amino}-3-[5-(4-chloro-phenyl)-thiophen-2-yl]-propionic acid, 2(S)-{[7-(4-tert-Butyl-phenoxy)-1-cyclopentylmethyl-isoquinoline-3-carbonyl]-amino}-3-(5-ethyl-thiophen-2-yl)-propionic acid, 2(S)-{[7-(4-tert-Butyl-phenoxy)-1-cyclopentylmethyl-isoquinoline-3-carbonyl]-amino}-3-furan-2-yl-propionic acid, 2(S)-{[7-(4-tert-Butyl-phenoxy)-1-cyclopentylmethyl-isoquinoline-3-carbonyl]-amino}-3-(2-trifluoromethyl-phenyl)-propionic acid, {(5-Bromo-thiophen-2-ylmethyl)-[7-(4-tert-butyl-phenoxy)-1-cyclopentylmethyl-isoquinoline-3-carbonyl]-amino}-acetic acid tert-butyl ester, 2(S)-{[7-(4-tert-Butyl-phenoxy)-1-cyclopentylmethyl-isoquinoline-3-carbonyl]-amino}-3-(3,5-difluorophenyl)-propionic acid,

[[7-(4-tert-Butyl-phenoxy)-1-cyclopentylmethyl-isoquinoline-3-carbonyl]-(5-methyl-thiophen-2-ylmethyl)-amino]-acetic acid, {(5-Bromo-thiophen-2-ylmethyl)-[7-(4-tert-butyl-phenoxy)-1-cyclopentylmethyl-isoquinoline-3-carbonyl]-amino}-acetic acid methyl ester,
{(4-Bromo-thiophen-2-ylmethyl)-[7-(4-tert-butyl-phenoxy)-1-cyclopentylmethyl-isoquinoline-3-carbonyl]-amino}-acetic acid,
{(5-Bromo-thiophen-2-ylmethyl)-[7-(4-tert-butyl-phenoxy)-1-cyclopentylmethyl-isoquinoline-3-carbonyl]-amino}-acetic acid,
Benzo[b]thiophen-3-yl-{[7-(4-tert-butyl-phenoxy)-1-cyclopentylmethyl-isoquinoline-3-carbonyl]-amino}-acetic acid,
2(S)-{[7-(4-tert-Butyl-phenoxy)-1-cyclopentylmethyl-isoquinoline-3-carbonyl]-amino}-3-(4-fluoro-phenyl)-propionic acid,
2(S)-{[7-(4-tert-Butyl-phenoxy)-1-cyclopentylmethyl-isoquinoline-3-carbonyl]-amino}-3-(5-propenyl-thiophen-2-yl)-propionic acid,
2(S)-{[7-(4-tert-Butyl-phenoxy)-1-cyclopentylmethyl-isoquinoline-3-carbonyl]-amino}-3-(5-propyl-thiophen-2-yl)-propionic acid,
2(S)-{[7-(4-tert-Butyl-phenoxy)-1-cyclopentylmethyl-isoquinoline-3-carbonyl]-amino}-3-[5-(3,3-dimethyl-but-1-enyl)-thiophen-2-yl]-propionic acid,
2(S)-{[7-(4-tert-Butyl-phenoxy)-1-cyclopentylmethyl-isoquinoline-3-carbonyl]-amino}-3-(5-hydroxymethyl-thiophen-2-yl)-propionic acid methyl ester,
2(S)-{[7-(4-tert-Butyl-phenoxy)-1-cyclopentylmethyl-isoquinoline-3-carbonyl]-amino}-3-(5-hydroxymethyl-thiophen-2-yl)-propionic acid,
2(S)-{[7-(4-tert-Butyl-phenoxy)-1-cyclopentylmethyl-isoquinoline-3-carbonyl]-amino}-3-(5-methyl-thiophen-2-yl)-propionic acid,
2(S)-{[7-(4-tert-Butyl-phenoxy)-1-cyclopentylmethyl-isoquinoline-3-carbonyl]-amino}-3-(5-isopropenyl-thiophen-2-yl)-propionic acid,
2(S)-{[7-(4-tert-Butyl-phenoxy)-1-cyclopentylmethyl-isoquinoline-3-carbonyl]-amino}-3-(5-isopropylthiophen-2-yl)-propionic acid,
3-(5-Bromo-thiophen-2-yl)-2(R)-{[7-(4-tert-butyl-phenoxy)-1-cyclopentylmethyl-isoquinoline-3-carbonyl]-amino}-propionic acid,
2(R)-{[7-(4-tert-Butyl-phenoxy)-1-cyclopentylmethyl-isoquinoline-3-carbonyl]-amino}-3-(5-chloro-thiophen-2-yl)-propionic acid,
2(S)-{[7-(4-tert-Butyl-phenoxy)-1-cyclopentylmethyl-isoquinoline-3-carbonyl]-amino}-3-(5-chloro-furan-2-yl)-propionic acid,
2(S)-{[7-(4-tert-Butyl-phenoxy)-1-cyclopentylmethyl-isoquinoline-3-carbonyl]-amino}-3-(2,5-dichloro-thiophen-3-yl)-propionic acid,
(5-Bromo-thiophen-2-yl)-{[7-(4-tert-butyl-phenoxy)-1-cyclopentylmethyl-isoquinoline-3-carbonyl]-amino}-acetic acid,
3-(5-Bromo-furan-2-yl)-2(S)-{[7-(4-tert-butyl-phenoxy)-1-cyclopentylmethyl-isoquinoline-3-carbonyl]-amino}-propionic acid,
3-(5-Bromo-thiophen-2-yl)-2(S)-{[7-(4-trans-tert-butyl-cyclohexyloxy)-1-cyclopentylmethyl-isoquinoline-3-carbonyl]-amino}-propionic acid,
3-(5-Bromo-thiophen-2-yl)-2(S)-{[6-(4-tert-butyl-phenoxy)-1-cyclopentylmethyl-isoquinoline-3-carbonyl]-amino}-propionic acid,
2(S)-{[7-(4-trans-tert-Butyl-cyclohexyloxy)-1-cyclopentylmethyl-isoquinoline-3-carbonyl]-amino}-3-(5-isopropenyl-thiophen-2-yl)-propionic acid,
2(S)-{[7-(4-trans-tert-Butyl-cyclohexyloxy)-1-cyclopentylmethyl-isoquinoline-3-carbonyl]-amino}-3-(5-isopropyl-thiophen-2-yl)-propionic acid,
2(S)-{[7-(4-tert-Butyl-phenoxy)-1-cyclopentylmethyl-isoquinoline-3-carbonyl]-amino}-3-(5-isopropyl-furan-2-yl)-propionic acid,
2(S)-{[1-Cyclopentylmethyl-7-(4-isopropyl-cyclohexyloxy)-isoquinoline-3-carbonyl]-amino}-3-(5-isopropyl-thiophen-2-yl)-propionic acid,
2(R)-{[7-(4-tert-Butyl-phenoxy)-1-cyclopentylmethyl-isoquinoline-3-carbonyl]-amino}-3-(5-isopropyl-thiophen-2-yl)-propionic acid,
2(S)-{[7-(4-tert-Butyl-phenoxy)-isoquinoline-3-carbonyl]-amino}-3-(5-isopropyl-thiophen-2-yl)-propionic acid,
2(S)-{[1-Cyclopentylmethyl-7-(4-trans-ethyl-cyclohexyloxy)-isoquinoline-3-carbonyl]-amino}-3-(5-isopropyl-thiophen-2-yl)-propionic acid,
2(S)-{[1-Cyclopentylmethyl-7-(4-isopropyl-phenoxy)-isoquinoline-3-carbonyl]-amino}-3-(5-isopropyl-thiophen-2-yl)-propionic acid,
2(S)-{[7-(4-tert-Butyl-phenoxy)-1-(tetrahydro-pyran-4-yl)-isoquinoline-3-carbonyl]-amino}-3-(5-isopropyl-thiophen-2-yl)-propionic acid,
2(S)-{[6-(4-tert-Butyl-phenoxy)-1-cyclopentylmethyl-isoquinoline-3-carbonyl]-amino}-3-(5-isopropyl-thiophen-2-yl)-propionic acid,
2(S)-{[7-(4-tert-Butyl-phenyl)-1-cyclopentylmethyl-isoquinoline-3-carbonyl]-amino}-3-(5-isopropyl-thiophen-2-yl)-propionic acid,
2(S)-{[7-(4-tert-Butyl-benzoyl)-1-cyclopentylmethyl-isoquinoline-3-carbonyl]-amino}-3-(5-isopropyl-thiophen-2-yl)-propionic acid,
3-(5-Acetyl-thiophen-2-yl)-2(S)-{[7-(4-tert-butyl-phenoxy)-1-cyclopentylmethyl-isoquinoline-3-carbonyl]-amino}-propionic acid,
7-(4-tert-Butyl-phenoxy)-1-cyclopentylmethyl-isoquinoline-3-carboxylic acid [1-(5-isopropyl-thiophen-2-ylmethyl)-2(R)-methanesulfonylamino-2-oxo-ethyl]-amide,
7-(4-tert-Butyl-phenoxy)-1-cyclopentylmethyl-isoquinoline-3-carboxylic acid [1-(5-isopropyl-thiophen-2-ylmethyl)-2(S)-methanesulfonylamino-2-oxo-ethyl]-amide,
7-(4-tert-Butyl-phenoxy)-1-cyclopentylmethyl-isoquinoline-3-carboxylic acid [1-benzyloxycarbamoyl-2-(5-isopropyl-thiophen-2-yl)-ethyl]-amide, and
7-(4-tert-Butyl-phenoxy)-1-cyclopentylmethyl-isoquinoline-3-carboxylic acid [1-hydroxycarbamoyl-2-(5-isopropyl-thiophen-2-yl)-ethyl]-amide.

In another embodiment, the method of treating the above-enumerated diseases comprises the administration of formula (X) wherein Y is selected from the group consisting of

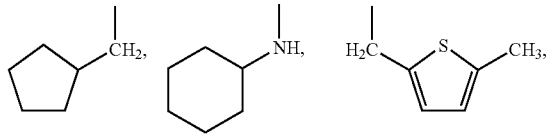 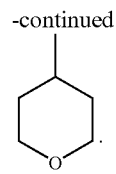

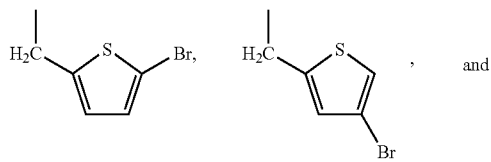

In another embodiment, the method of treating the above-enumerated diseases comprises the administration of formula (X) wherein Y is -methylene-cyclopentyl.

Also included within the scope of the invention are the individual enantiomers of the compounds represented by Formula (I or X) above as well as any wholly or partially racemic mixtures thereof. The present invention also covers the individual enantiomers of the compounds represented by formulas above as mixtures with diastereoisomers thereof in which one or more stereocenters are inverted.

Compounds of the present invention are listed in Table 1 below.

TABLE 1

| EX. | Compound | Name |
|---|---|---|
| 1 | (structure) | 2(S)-{[7-(4-tert-Butyl-phenoxy)-1-cyclopentylmethyl-isoquinoline-3-carbonyl]-amino}-3-(5-phenyl-thiophen-2-yl)-propionic acid |
| 2 | (structure) Chiral | 2(S)-{[7-(4-tert-Butyl-phenoxy)-1-cyclopentylmethyl-isoquinoline-3-carbonyl]-amino}-3-[5-(4-trifluoromethyl-phenyl)-thiophen-2-yl]-propionic acid |

TABLE 1-continued

| EX. | Compound | | Name |
|---|---|---|---|
| 3 | 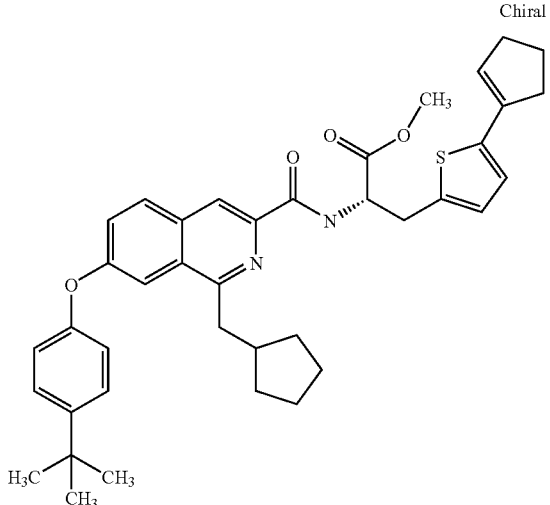 | Chiral | 2(S)-{[7-(4-tert-Butyl-phenoxy)-1-cyclopentylmethyl-isoquinoline-3-carbonyl]-amino}-3-(5-cyclopent-1-enyl-thiophen-2-yl)-propionic acid methyl ester |
| 4 | 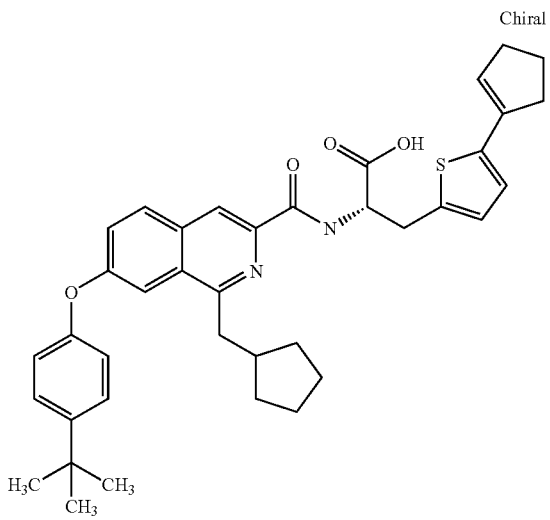 | Chiral | 2(S)-{[7-(4-tert-Butyl-phenoxy)-1-cyclopentylmethyl-isoquinoline-3-carbonyl]-amino}-3-(5-cyclopent-1-ennyl-thiophen-2-yl)-propionic acid |
| 5 | 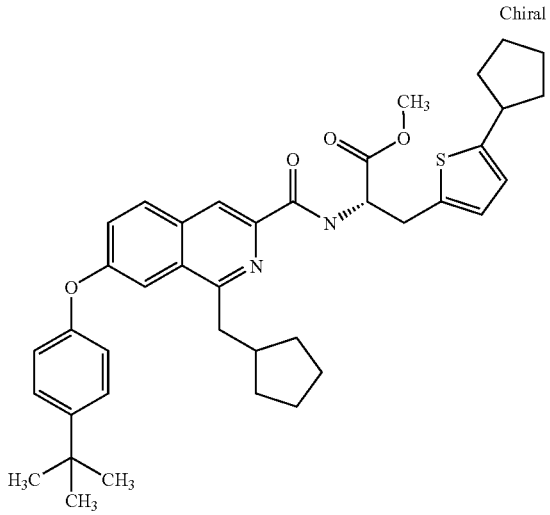 | Chiral | 2(S)-{[7-(4-tert-Butyl-phenoxy)-1-cyclopentylmethyl-isoquinoline-3-carbonyl]-amino}-3-(5-cyclopentyl-thiophen-2-yl)-propionic acid methyl ester |

TABLE 1-continued

| EX. | Compound | Name |
|---|---|---|
| 6 | 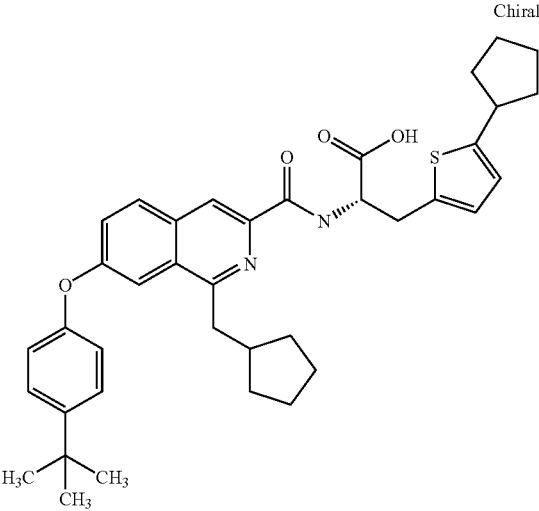 | 2(S)-{[7-(4-tert-Butyl-phenoxy)-1-cyclopentylmethyl-isoquinoline-3-carbonyl]-amino}-3-(5-cyclopent-thiophen-2-yl)-propionic acid |
| 7 | 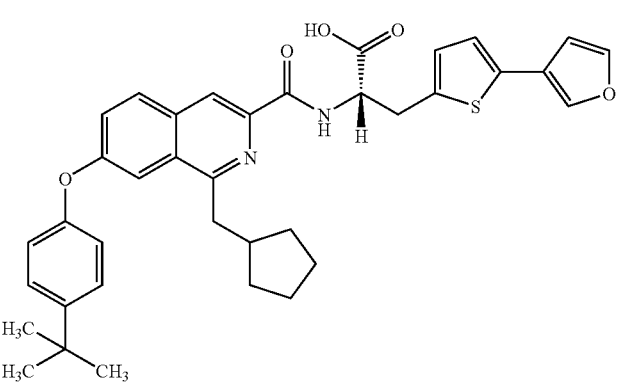 | 2(S)-{[7-(4-tert-Butyl-phenoxy)-1-cyclopentylmethyl-isoquinoline-3-carbonyl]-amino}-3-(5-furan-3-yl-thiophen-2-yl)-propionic acid |
| 8 | 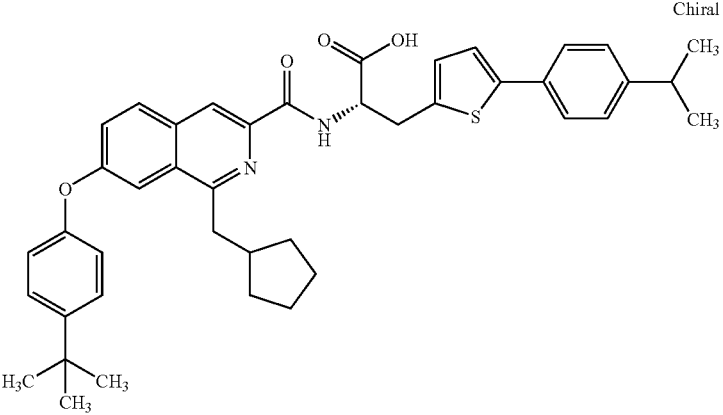 | 2(S)-{[7-(4-tert-Butyl-phenoxy)-1-cyclopentylmethyl-isoquinoline-3-carbonyl]-amino}-3-[5-(4-isopropyl-phenyl)-thiophen-2-yl]-propionic acid |

TABLE 1-continued

| EX. | Compound | Name |
|---|---|---|
| 9 | 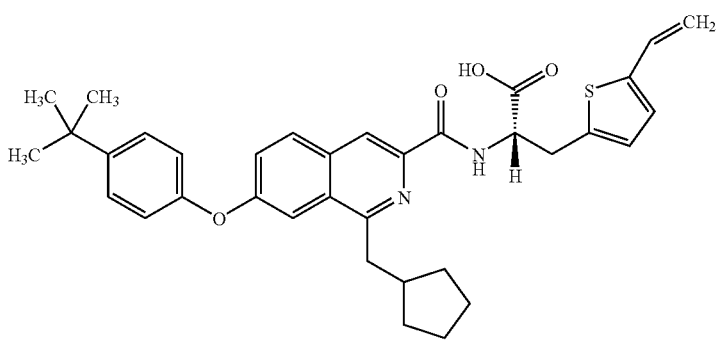 | 2(S)-{[7-(4-tert-Butyl-phenoxy)-1-cyclopentylmethyl-isoquinoline-3-carbonyl]-amino}-3-(5-vinyl-thiophen-2-yl)-propionic acid |
| 10 | 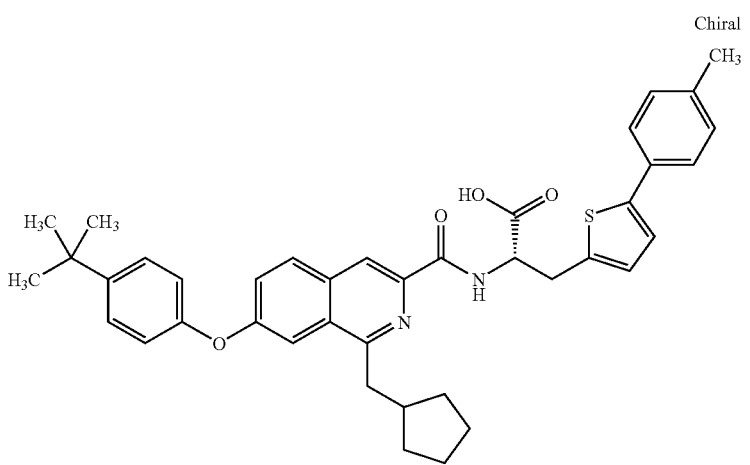 Chiral | 2(S)-{[7-(4-tert-Butyl-phenoxy)-1-cyclopentylmethyl-isoquinoline-3-carbonyl]-amino}-3-(5-p-tolyl-thiophen-2-yl)-propionic acid |
| 11 | 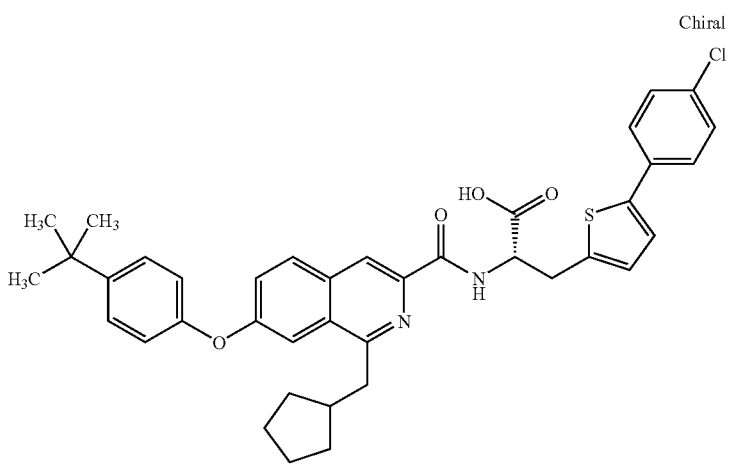 Chiral | 2(S)-{[7-(4-tert-Butyl-phenoxy)-1-cyclopentylmethyl-isoquinoline-3-carbonyl]-amino}-3-[5-(4-chloro-phenyl)-thiophen-2-yl]-propionic acid |

TABLE 1-continued
| EX. | Compound | Name |
|---|---|---|
| 12 | 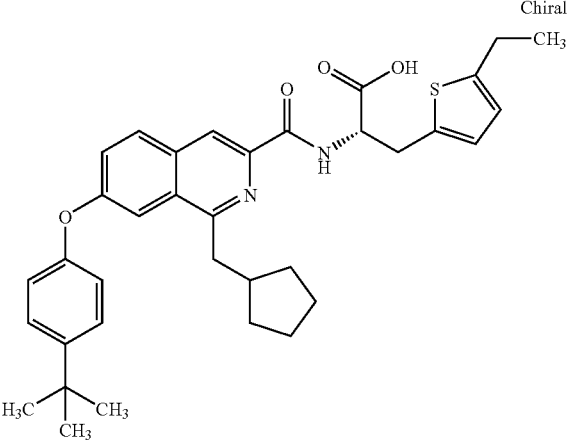 | 2(S)-{[7-(4-tert-Butyl-phenoxy)-1-cyclopentylmethyl-isoquinoline-3-carbonyl]-amino}-3-(5-ethyl-thiophen-2-yl)-propionic acid |
| 13 | 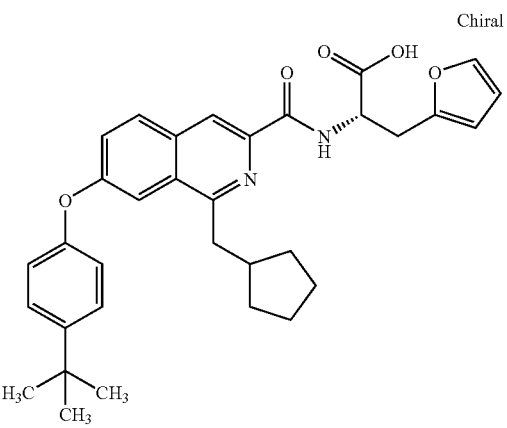 | 2(S)-{[7-(4-tert-Butyl-phenoxy)-1-cyclopentylmethyl-isoquinoline-3-carbonyl]-amino}-3-furan-2-yl-propionic acid |
| 14 | 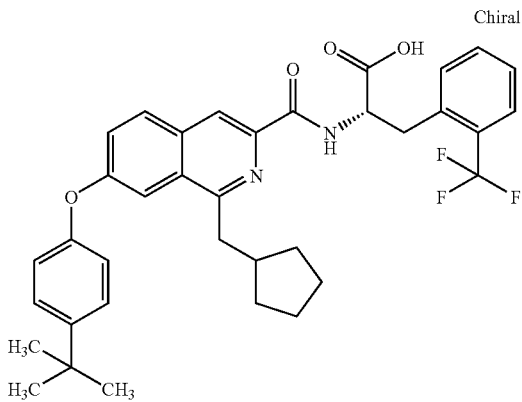 | 2(S)-{[7-(4-tert-Butyl-phenoxy)-1-cyclopentylmethyl-isoquinoline-3-carbonyl]-amino}-3-(2-trifluoromethyl-phenyl)-propionic acid |

TABLE 1-continued

| EX. | Compound | Name |
|---|---|---|
| 15 | | {(5-Bromo-thiophen-2-ylmethyl)-[7-(4-tert-butyl-phenoxy)-1-cyclopentylmethyl-isoquinoline-3-carbonyl]-amino}-acetic acid tert-butyl ester |
| 16 | Chiral | 2(S)-{[7-(4-tert-Butyl-phenoxy)-1-cyclopentylmethyl-isoquinoline-3-carbonyl]-amino}-3-(3,5-difluorophenyl)-propionic acid |
| 17 | | [[7-(4-tert-Butyl-phenoxy)-1-cyclopentylmethyl-isoquinoline-3-carbonyl]-(5-methyl-thiophen-2-ylmethyl)-amino]-acetic acid |
| 18 | | {(5-Bromo-thiophen-2-ylmethyl)-[7-(4-tert-butyl-phenoxy)-1-cyclopentylmethyl-isoquinoline-3-carbonyl]-amino}-acetic acid methyl ester |

TABLE 1-continued

| EX. | Compound | Name |
|---|---|---|
| 19 | 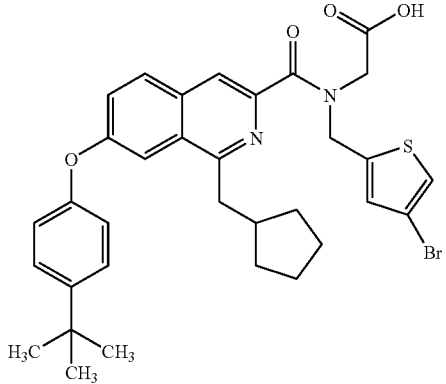 | {(4-Bromo-thiophen-2-ylmethyl)-[7-(4-tert-butyl-phenoxy)-1-cyclopentylmethyl-isoquinoline-3-carbonyl]-amino}-acetic acid |
| 20 | 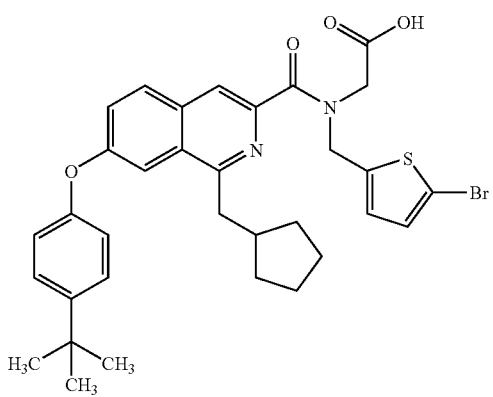 | {(5-Bromo-thiophen-2-ylmethyl)-[7-(4-tert-butyl-phenoxy)-1-cyclopentylmethyl-isoquinoline-3-carbonyl]-amino}-acetic acid |
| 21 | 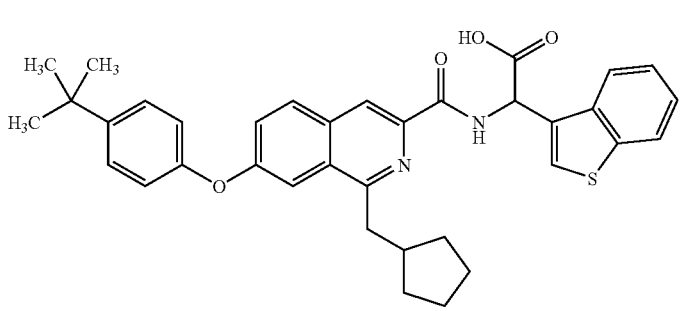 | Benzo[b]thiophen-3-yl-{[7-(4-tert-butyl-phenoxy)-1-cyclopentylmethyl-isoquinoline-3-carbonyl]-amino}-acetic acid |
| 22 | 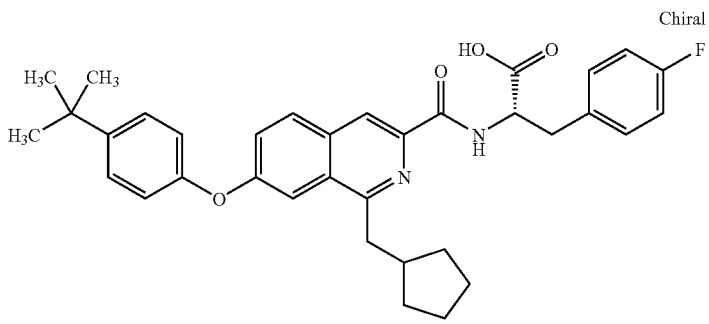 | 2(S)-{[7-(4-tert-Butyl-phenoxy)-1-cyclopentylmethyl-isoquinoline-3-carbonyl]-amino}-3-(4-fluoro-phenyl)-propionic acid |

TABLE 1-continued

| EX. | Compound | Name |
|---|---|---|
| 23 | | 2(S)-{[7-(4-tert-Butyl-phenoxy)-1-cyclopentylmethyl-isoquinoline-3-carbonyl]-amino}-3-(5-propenyl-thiophen-2-yl)-propionic acid |
| 24 | | 2(S)-{[7-(4-tert-Butyl-phenoxy)-1-cyclopentylmethyl-isoquinoline-3-carbonyl]-amino}-3-(5-propyl-thiophen-2-yl)-propionic acid |
| 25 | | 2(S)-{[7-(4-tert-Butyl-phenoxy)-1-cyclopentylmethyl-isoquinoline-3-carbonyl]-amino}-3-[5-(3,3-dimethyl-but-1-enyl)-thiophen-2-yl]-propionic acid |

TABLE 1-continued

| EX. | Compound | Name |
|---|---|---|
| 26 | | 2(S)-{[7-(4-tert-Butyl-phenoxy)-1-cyclopentylmethyl-isoquinoline-3-carbonyl]-amino}-3-(5-hydroxymethyl-thiophen-2-yl)-propionic acid methyl ester |
| 27 | | 2(S)-{[7-(4-tert-Butyl-phenoxy)-1-cyclopentylmethyl-isoquinoline-3-carbonyl]-amino}-3-(5-hydroxymethyl-thiophen-2-yl)-propionic acid |
| 28 | | 2(S)-{[7-(4-tert-Butyl-phenoxy)-1-cyclopentylmethyl-isoquinoline-3-carbonyl]-amino}-3-(5-methyl-thiophen-2-yl)-propionic acid |
| 29 | | 2(S)-{[7-(4-tert-Butyl-phenoxy)-1-cyclopentylmethyl-isoquinoline-3-carbonyl]-amino}-3-(5-isopropenyl-thiophen-2-yl)-propionic acid |

TABLE 1-continued
| EX. | Compound | Name |
|---|---|---|
| 30 | 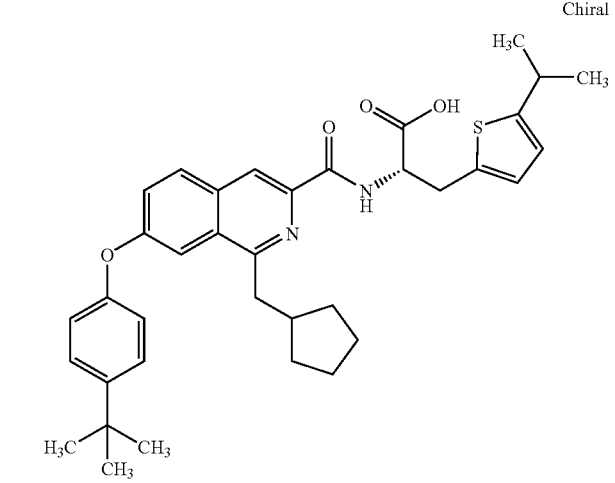 | 2(S)-{[7-(4-tert-Butyl-phenoxy)-1-ccyclopentylmethyl-isoquinoline-3-carbonyl]-amino}-3-(5-isopropylthiophen-2-yl)-propionic acid |
| 31 | 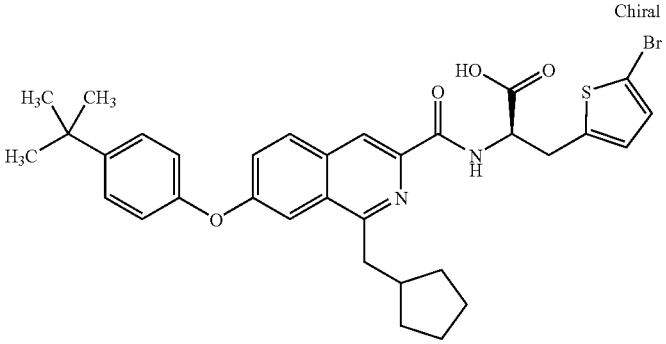 | 3-(5-Bromo-thiophen-2-yl)-2(R)-{[7-(4-tert-butyl-phenoxy)-1-cyclopentylmethyl-isoquinoline-3-carbonyl]-amino}-propionic acid |
| 32 | 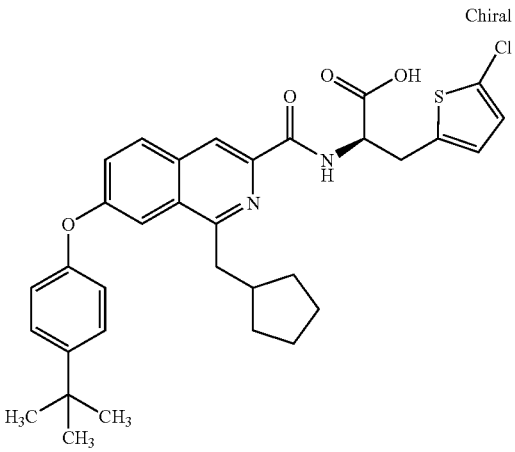 | 2(R)-{[7-(4-tert-Butyl-phenoxy)-1-cyclopentylmethyl-isoquinoline-3-carbonyl]-amino}-3-(5-chloro-thiophen-2-yl)-propionic acid |

TABLE 1-continued
| EX. | Compound | Name |
|---|---|---|
| 33 | 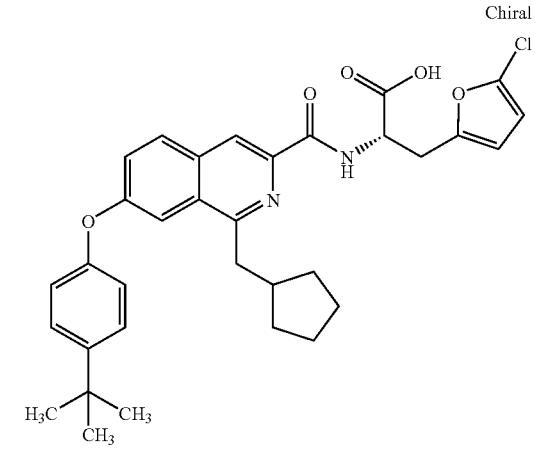 | 2(S)-{[7-(4-tert-Butyl-phenoxy)-1-cyclopentylmethyl-isoquinoline-3-carbonyl]-amino}-3-(5-chloro-furan-2-yl)-propionic acid |
| 34 | 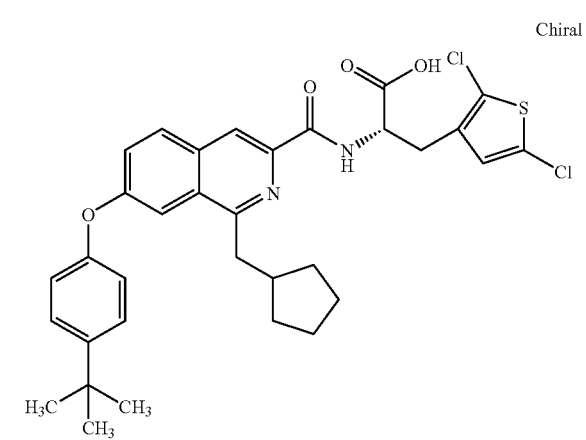 | 2(S)-{[7-(4-tert-Butyl-phenoxy)-1-cyclopentylmethyl-isoquinoline-3-carbonyl]-amino}-3-(2,5-dichloro-thiophen-3-yl)-propionic acid |
| 35 | 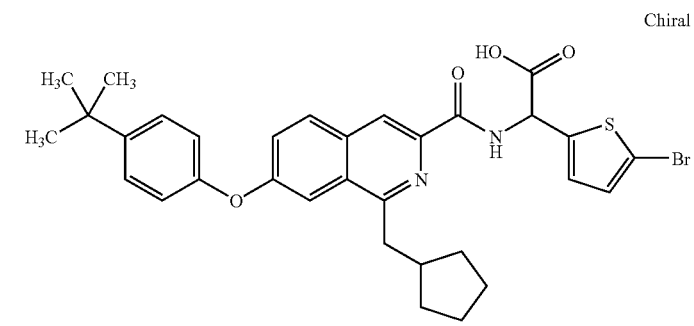 | (5-Bromo-thiophen-2-yl)-{[7-(4-tert-butyl-phenoxy)-1-cyclopentylmethyl-isoquinoline-3-carbonyl]-amino}-acetic acid |

TABLE 1-continued

| EX. | Compound | Name |
|---|---|---|
| 36 | | 3-(5-Bromo-furan-2-yl)-2(S)-{[7-(4-tert-butyl-phenoxy)-1-cyclopentylmethyl-isoquinoline-3-carbonyl]-amino}-propionic acid |
| 37 | | 3-(5-Bromo-thiophen-2-yl)-2(S)-{[7-(4-trans-tert-butyl-cyclohexyloxy)-1-cyclopentylmethyl-isoquinoline-3-carbonyl]-amino}-propionic acid |
| 38 | | 3-(5-Bromo-thiophen-2-yl)-2(S)-p{[6-(4-tert-butyl-phenoxy)-1-cyclopentylmethyl-isoquinoline-3-carbonyl]-amino}-propionic acid |
| 39 | | 2(S)-{[7-(4-trans-tert-Butyl-cyclohexyloxy)-1-cyclopentylmethyl-isoquinoline-3-carbonyl]-amino}-3-(5-isopropenyl-thiophen-2-yl)-propionic acid |

TABLE 1-continued

| EX. | Compound | Name |
|---|---|---|
| 40 | Chiral | 2(S)-{[7-(4-trans-tert-Butyl-cyclohexyloxy)-1-cyclopentylmethyl-isoquinoline-3-carbonyl]-amino}-3-(5-isopropyl-thiophen-2-yl)-propionic acid |
| 41 | Chiral | 2(S)-{[7-(4-tert-Butyl-phenoxy)-1-cyclopentylmethyl-isoquinoline-3-carbonyl]-amino}-3-(5-isopropyl-furan-2-yl)-propionic acid |
| 42 | Chiral | 2(S)-{[1-Cyclopentylmethyl-7-(4-isopropyl-cyclohexyloxy)-isoquinoline-3-carbonyl]-amino}-3-(5-isopropyl-thiophen-2-yl)-propionic acid |

TABLE 1-continued

| EX. | Compound | Name |
|-----|----------|------|
| 43 | Chiral | 2(R)-{[7-(4-tert-Butyl-phenoxy)-1-cyclopentylmethyl-isoquinoline-3-carbonyl]-amino}-3-(5-isopropyl-thiophen-2-yl)-propionic acid |
| 44 | Chiral | 2(S)-{[7-(4-tert-Butyl-phenoxy)-isoquinoline-3-carbonyl]-amino}-3-(5-isopropyl-thiophen-2-yl)-propionic acid |
| 45 | Chiral | 2(S)-{[1-Cyclopentylmethyl-7-(4-trans-ethyl-cyclohexyloxy)-isoquinoline-3-carbonyl]-amino}-3-(5-isopropyl-thiophen-2-yl)-propionic acid |

TABLE 1-continued

| EX. | Compound | Name |
|---|---|---|
| 46 | 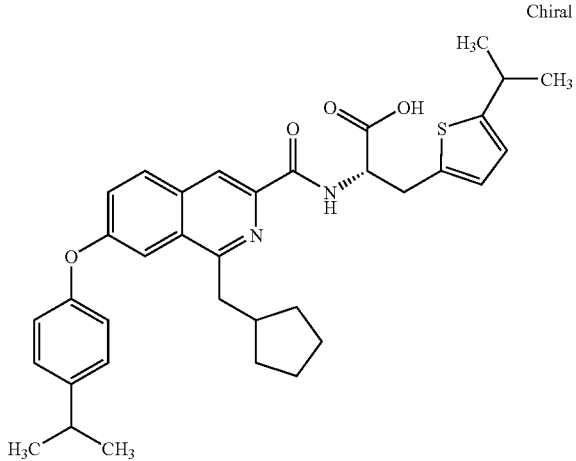 | 2(S)-{[1-Cyclopentylmethyl-7-(4-isopropyl-phenoxy)-isoquinoline-3-carbonyl]-amino}-3-(5-isopropyl-thiophen-2-yl)-propionic acid |
| 47 | 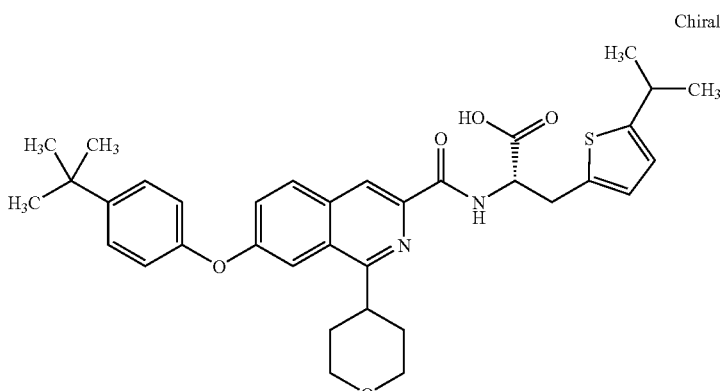 | 2(S)-{[7-(4-tert-Butyl-phenoxy)-1-(tetrahydro-pyran-4-yl)-isoquinoline-3-carbonyl]-amino}-3-(5-isopropyl-thiophen-2-yl)-propionic acid |
| 48 | 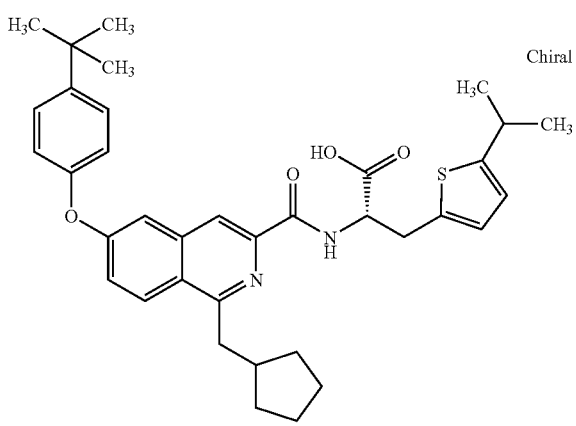 | 2(S)-{[6-(4-tert-Butyl-phenoxy)-1-cyclopentylmethyl-isoquinoline-3-carbonyl]-amino}-3-(5-isopropyl-thiophen-2-yl)-propionic acid |

TABLE 1-continued

| EX. | Compound | Name |
| --- | --- | --- |
| 49 | Chiral | 2(S)-{[7-(4-tert-Butyl-phenyl)-1-cyclopentylmethyl-isoquinoline-3-carbonyl]-amino}-3-(5-isopropyl-thiophen-2-yl)-propionic acid |
| 50 | Chiral | 2(S)-{[7-(4-tert-Butyl-benzoyl)-1-cyclopentylmethyl-isoquinoline-3-carbonyl]-amino}-3-(5-isopropyl-thiophen-2-yl)-propionic acid |
| 51 | Chiral | 3-(5-Acetyl-thiophen-2-yl)-2(S)-{[7-(4-tert-butyl-phenoxy)-1-cyclopentylmethyl-isoquinoline-3-carbonyl]-amino}-propionic acid |
| 52 | Chiral | 7-(4-tert-Butyl-phenoxy)-1-cyclopentylmethyl-isoquinoline-3-carboxylic acid [1-(5-isopropyl-thiophen-2-ylmethyl)-2(R)-methanesulfonylamino-2-oxo-ethyl]-amide |

TABLE 1-continued

| EX. | Compound | Name |
|---|---|---|
| 53 | Chiral | 7-(4-tert-Butyl-phenoxy)-1-cyclopentylmethyl-isoquinoline-3-carboxylic acid [1-(5-isopropyl-thiophen-2-ylmethyl)-2(S)-methanesulfonylamino-2-oxo-ethyl]-amide |
| 54 | Chiral | 7-(4-tert-Butyl-phenoxy)-1-cyclopentylmethyl-isoquinoline-3-carboxylic acid [1-benzyloxycarbamoyl-2-(5-isopropyl-thiophen-2-yl)-ethyl]-amide |
| 55 | Chiral | 7-(4-tert-Butyl-phenoxy)-1-cyclopentylmethyl-isoquinoline-3-carboxylic acid [1-hydroxycarbamoyl-2-(5-isopropyl-thiophen-2-yl)-ethyl]-amide |

Incomplete valences for heteroatoms such as oxygen and nitrogen in the chemical structures listed in Table 1 are assumed to be completed by hydrogen.

In another aspect, the present invention comprises a pharmaceutical composition comprising the compound of Formula (I or X) and one or more pharmaceutically acceptable carriers, excipients, or diluents.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or $S(O)_2$ atoms. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or $S(O)_2$ atoms. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or $S(O)_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may containing one or more O, S, S(O), or $S(O)_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon—carbon triple bond, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or $S(O)_2$ atoms.

As used herein, the term "alkynylene" refers to a straight or branched chain divalent hydrocarbon radical having from two to ten carbon atoms and one or more carbon-carbon triple bonds, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may containing one or more O, S, S(O), or $S(O)_2$ atoms. Examples of "alkynylene" as used herein include, but are not limited to, ethyne-1,2-diyl, propyne-1,3-diyl, and the like.

As used herein, "cycloalkyl" refers to a alicyclic hydrocarbon group optionally possessing one or more degrees of unsaturation, having from three to twelve carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally possessing one or more degrees of unsaturation, containing one or more heteroatomic substitutions selected from S, SO, $SO_2$, O, or N, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, SO$_2$, O, or N, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-diyl, and the like.

As used herein, the term "aryl" refers to a benzene ring or to an optionally substituted benzene ring system fused to one or more optionally substituted benzene rings, optionally substituted with substituents selected from the group consisting of halo, lower alkyl, lower alkoxy, lower alkylsulfanyl, lower alkylsulfenyl, lower alkylsulfonyl, di(lower alkyl) aminoalkyl, aminoalkyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acylamino, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of halo, lower alkyl, lower alkoxy, lower alkylsulfanyl, lower alkylsulfenyl, lower alkylsulfonyl, di(lower alkyl) aminoalkyl, aminoalkyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acylamino, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five-to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

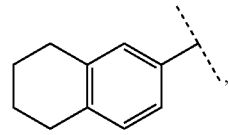

and the like.

As used herein, the term "fused cycloalkylarylene" refers to a fused cycloalkylaryl, wherein the aryl group is divalent. Examples include

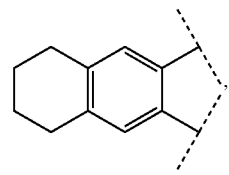

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

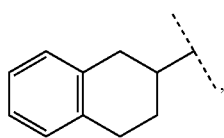

and the like.

As used herein, the term "fused arylcycloalkylene" refers to a fused arylcycloalkyl, wherein the cycloalkyl group is divalent. Examples include

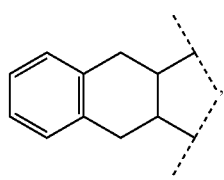

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

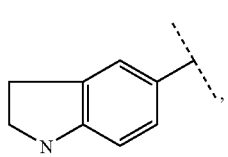

and the like

As used herein, the term "fused heterocyclylarylene" refers to a fused heterocyclylaryl, wherein the aryl group is divalent. Examples include

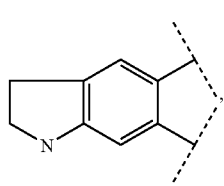

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

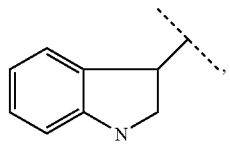

and the like.

As used herein, the term "fused arylheterocyclylene" refers to a fused arylheterocyclyl, wherein the heterocyclyl group is divalent. Examples include

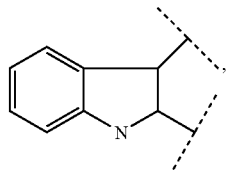

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

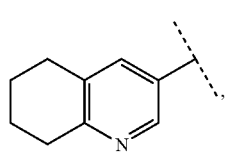

and the like.

As used herein, the term "fused cycloalkylheteroarylene" refers to a fused cycloalkylheteroaryl, wherein the heteroaryl group is divalent. Examples include

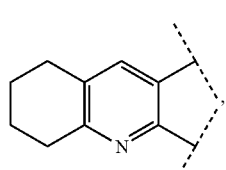

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include 5-aza-1-indanyl,

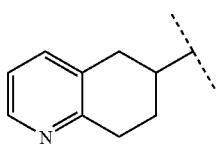

and the like.

As used herein, the term "fused heteroarylcycloalkylene" refers to a fused heteroarylcycloalkyl, wherein the cycloalkyl group is divalent. Examples include

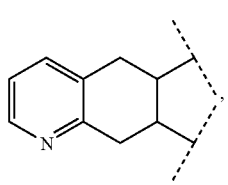

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl,

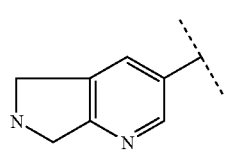

and the like.

As used herein, the term "fused heterocyclylheteroarylene" refers to a fused heterocyclylheteroaryl, wherein the heteroaryl group is divalent. Examples include

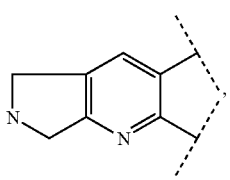

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include -5-aza-2,3-dihydrobenzofuran-2-yl,

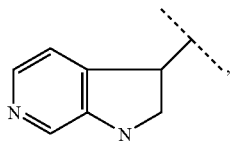

and the like.

As used herein, the term "fused heteroarylheterocyclylene" refers to a fused heteroarylheterocyclyl, wherein the heterocyclyl group is divalent. Examples include

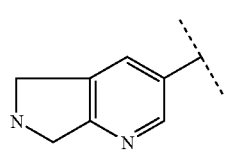

and the like.

As used herein, the term "acid isostere" refers to a substituent group that may ionize at physiological pH to bear a net negative charge. Examples of such "acid isosteres" include but are not limited to heteroaryl groups such as but not limited to isoxazol-3-ol-5-yl, 1H-tetrazole-5-yl, or 2H-tetrazole-5-yl. Such acid isosteres include but are not limited to heterocyclyl groups such as but not limited to imidazolidine-2,4-dione-5-yl, imidazolidine-2,4-dione-1-yl, 1,3-thiazolidine-2,4-dione-5-yl, or 5-hydroxy-4H-pyran-4-on-2-yl, 1,2,5-thiadiazolidin-3-one-1,1-dioxide-4-yl, or 1,2-5-thiadiazolidin-3-one-1,1-dioxide-5-yl.

As used herein, the term "ester isostere" refers to a substituent group that can be metabolically stable and can retain the selectivity and affinity of a corresponding ester toward a target protein. Examples of such "ester isosteres" include, but are not limited to, heteroaryl groups such as, but not limited to, 1,3-oxazole-5-yl, 1,3-oxazole-2-yl, 1,2,3-oxadiazole-5-yl, 1,2,4-oxadiazole-5-yl, 1,3,4-oxadiazole-5-yl, 1,2,3-thiadiazole-5-yl, 1,2,4-thiadiazole-5-yl, 1,3,4-thiadiazole-5-yl, 5-alkyl-1,3-oxazole-2-yl, 2-alkyl-1,3-oxazole-5-yl, 4-alkyl-1,2,3-oxadiazole-5-yl, 3-alkyl-1,2,4-oxadiazole-5-yl, 2-alkyl-1,3,4-oxadiazole-5-yl, 4-alkyl-1,2,3-thiadiazole-5-yl, 3-alkyl-1,2,4-thiadiazole-5-yl, 2-alkyl-1,3,4-thiadiazole-5-yl, 1,2,4-triazole-1-yl, 3-alkyl-1,2,4-triazole-1-yl, tetrazole-1-yl, and 1-alkyl-tetrazole-5-yl; aryl groups such as, but not limited to, 3,5-difluoro-4-alkoxyphenyl; and heterocyclyl groups such as, but not limited to, 1-alkyl-imidazolidine-2,4-dione-5-yl, imidazolidine-2,4-dione-1-yl, 3-alkyl-1,3-thiazolidine-2,4-dione-5-yl, and 5-alkoxy-4H-pyran-4-on-2-yl. The alkyl groups in the heterocyclyl, aryl, and heteroaryl groups of the ester isosteres may be replaced with a phenyl or alkylphenyl group.

As used herein, the term "direct bond", where part of a structural variable specification, refers to the direct joining of the substituents flanking (preceding and succeeding) the variable taken as a "direct bond".

As used herein, the term "alkoxy" refers to the group $R_aO-$, where $R_a$ is alkyl.

As used herein, the term "alkenyloxy" refers to the group $R_aO-$, where $R_a$ is alkenyl.

As used herein, the term "alkynyloxy" refers to the group $R_aO-$, where $R_a$ is alkynyl.

As used herein, the term "alkylsulfanyl" refers to the group $R_aS-$, where $R_a$ is alkyl.

As used herein, the term "alkenylsulfanyl" refers to the group $R_aS-$, where $R_a$ is alkenyl.

As used herein, the term "alkynylsulfanyl" refers to the group $R_aS-$, where $R_a$ is alkynyl.

As used herein, the term "alkylsulfenyl" refers to the group $R_aS(O)-$, where $R_a$ is alkyl.

As used herein, the term "alkenylsulfenyl" refers to the group $R_aS(O)-$, where $R_a$ is alkenyl.

As used herein, the term "alkynylsulfenyl" refers to the group $R_aS(O)-$, where $R_a$ is alkynyl.

As used herein, the term "alkylsulfonyl" refers to the group $R_aSO_2-$, where $R_a$ is alkyl.

As used herein, the term "alkenylsulfonyl" refers to the group $R_aSO_2-$, where $R_a$ is alkenyl.

As used herein, the term "alkynylsulfonyl" refers to the group $R_aSO_2-$, where $R_a$ is alkynyl.

As used herein, the term "acyl" refers to the group $R_aC(O)-$, where $R_a$ is alkyl, alkenyl, alkynyl, cycloalkyl, cycloalkenyl, or heterocyclyl.

As used herein, the term "aroyl" refers to the group $R_aC(O)-$, where $R_a$ is aryl.

As used herein, the term "heteroaroyl" refers to the group $R_aC(O)-$, where $R_a$ is heteroaryl.

As used herein, the term "alkoxycarbonyl" refers to the group $R_aOC(O)-$, where $R_a$ is alkyl.

As used herein, the term "acyloxy" refers to the group $R_aC(O)O-$, where $R_a$ is alkyl, alkenyl, alkynyl, cycloalkyl, cycloalkenyl, or heterocyclyl.

As used herein, the term "aroyloxy" refers to the group $R_aC(O)O-$, where $R_a$ is aryl.

As used herein, the term "heteroaroyloxy" refers to the group $R_aC(O)O-$, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, $-CH_2-O-CH_2-$, $-CH_2-SO_2-CH_2-$, $-CH_2-NH-CH_3$ and so forth.

As used herein, the term "solvate" is a complex of variable stoichiometry formed by a solute (in this invention, a compound of Formula (X or XI)) and a solvent. Such solvents for the purpose of the invention may not substantially interfere with the biological activity of the solute. Solvents may be, by way of example, water, ethanol, or acetic acid.

As used herein, the term "biohydrolyzable ester" is an ester of a drug substance (in this invention, a compound of Formula (X or XI)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to Formula (I or X) in plasma. Many examples of such are known in the art and include by way of example lower alkyl esters (e.g., $C_1$–$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I or X)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to Formula (I or X) in plasma. Many examples of such are known in the art and include by way of example lower alkyl amides, alpha-amino acid amides, alkoxyacyl amides, and alkylaminoalkylcarbonyl amides.

As used herein, the term "prodrug" includes biohydrolyzable amides and biohydrolyzable esters and encompasses a) compounds in which the biohydrolyzable functionality in such a prodrug is encompassed in the compound of formula (I or X), and b) compounds which may be oxidized or reduced biologically at a given functional group to yield drug substances of formula (I or X). Examples of these functional groups include, but are not limited to, 1,4-dihydropyridine, N-alkylcarbonyl-1,4-dihydropyridine, 1,4-cyclohexadiene, tert-butyl, and the like.

Whenever the terms "alkyl" or "aryl" or either of their prefix roots appear in a name of a substituent (e.g. arylalkoxyaryloxy) they shall be interpreted as including those limitations given above for "alkyl" and "aryl". Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent $-SO_2NH_2$.

As used herein, the term "carbamoyl" shall refer to the substituent $-C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent $-S(O)_2-$.

The compounds can be prepared according to the following reaction Schemes (in which variables are as defined before or are defined) using readily available starting materials, reagents and conventional synthesis procedures. In these reactions, it is also possible to make use of variants which are themselves known to those of ordinary skill in this art, but are not mentioned in greater detail.

The present invention also provides a method for the synthesis of compounds useful as intermediates in the preparation of compounds of Formula (I or X) along with methods for the preparation of compounds of Formula (I or X).

Scheme XIV describes the synthesis of a compound of formula (66). $R_{85}$ and $R_{86}$ may be groups such as but not limited to hydrogen, alkyl, or -alkylene-aryl. $R_{81}$ may be a group such as the side chain of a natural or unnatural amino acid. $R_{82}$ may be a group such as aryl, heteroaryl, alkyl, or cycloalkyl. $R_{84}$ may be a group such as but not limited to alkyl, aryl, heteroaryl, cycloalkyl, -alkylene-cycloalkyl, or -alkylene-aryl.

Compound (62) represents a nitrogen containing fused heterocyclylaryl ring system which may be synthesized by methods known in the art, such as acid catalyzed condensation of the corresponding amino acid with a carbonyl compound $R_{85}C(O)R_{86}$, followed by protection at nitrogen with a protecting group group such as but not limited to BOC. (62) may be treated with a peptide coupling agent such as DIC or HBTU, in the presence or absence of a base such as DIEA, in a solvent such as DMF of DCM, and an amino ester such as (63), to provide (64). An amine similar in structure to (63) may also be used to provide (64) without a methoxycarbonyl functionality. The phenol functionality of (64) may be functionalized by treatment of (64) with a primary or secondary alcohol in a solvent such as THF, with dialkyl azodicarboxylate and triphenylphosphine at a temperature of from −20° C. to 25° C., to give (65) where $R_{82}$ is alkyl, substituted alkyl, or cycloalkyl. (64) may also be treated with a aryl or heteroaryl boronic acid and copper (II) acetate to afford (65) where $R_{82}$ is aryl or heteroaryl. The $PG_1$ group of (65) may be removed as appropriate; the nitrogen thus freed may be functionalized with $R_{83}$, where $R_{83}$ represents groups such as but not limited to a alkylsulfenyl group, a alkoxycarbonyl group, or an acyl or alkanoyl group. The methyl ester of the intermediate may be removed by treatment with, for example, lithium hydroxide in aqueous THF-methanol at a temperature of from 0° C. to 25° C., to afford (66).

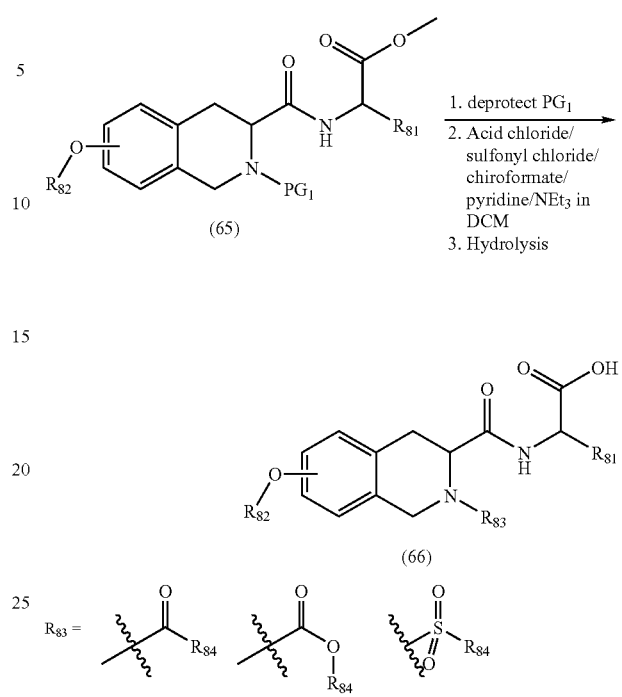

Scheme XV depicts the synthesis of a compound of formula (70). $R_{85}$, $R_{82}$, and $R_{81}$ have the meanings described for Scheme XIV. The phenolic functionality of (67) may be functionalized as in Scheme XIV, and the $PG_1$ protecting group may be removed with a reagent such as TFA, where $PG_1$ is tBOC. (68) may be treated with a reagent such as dichlorodicyanoquinone (DDQ) in a solvent such as toluene, at a temperature of from 25° C. to 110° C., to afford the acid (69) after hydrolysis of the ester with a reagent such as lithium hydroxide in a solvent such as aqueous THF. In manner similar to that described in Scheme XIV, the acid (69) may be coupled with an amino ester or other amine and the ester, if present, may be hydrolyzed with aqueous alkali to afford (70).

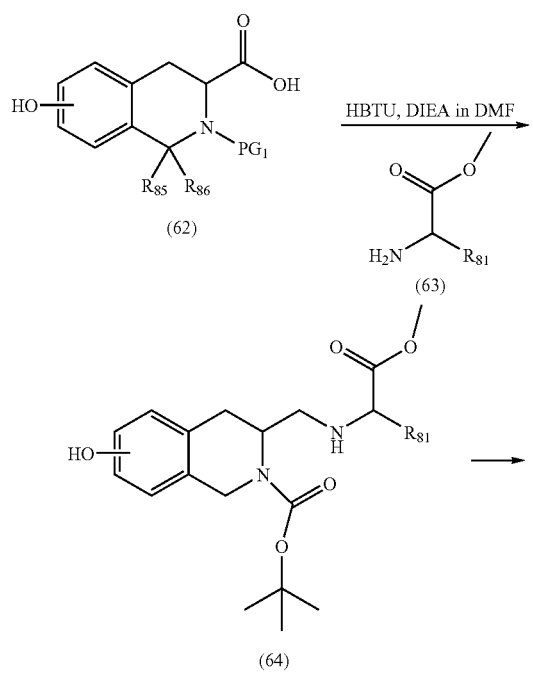

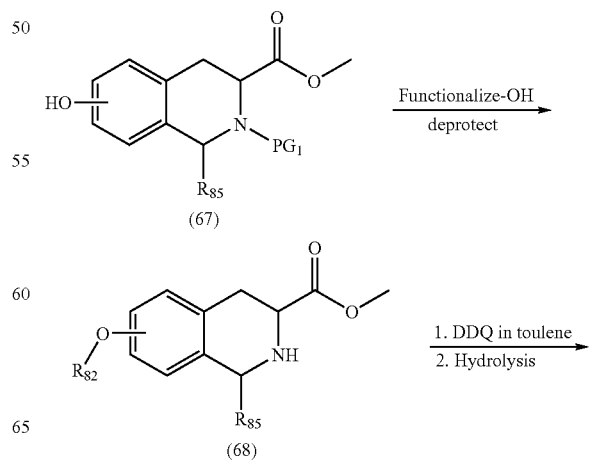

-continued

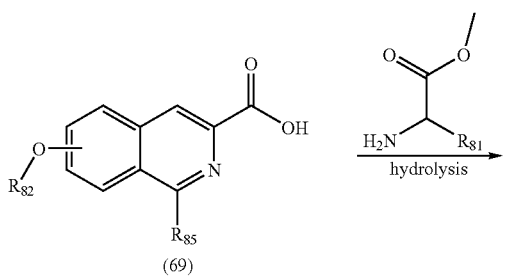

(69)

(70)

Scheme XVI describes the synthesis of intermediates and further compounds of Formula I. The acid (69) may be coupled with a functionalized bromoaryl alanine ester, or other similar bromoaromatic substituted amine, under conditions described previously to afford (71). (71) may be transformed to (72) employing conditions described in Scheme II. Similarly, (69) may be coupled with a hydroxyaryl alanine ester, or other similar hydroxyaryl or hydroxyheteroaryl substituted amine, to give (73), which may be functionalized as described in Scheme III to provide (74).

Scheme XVI

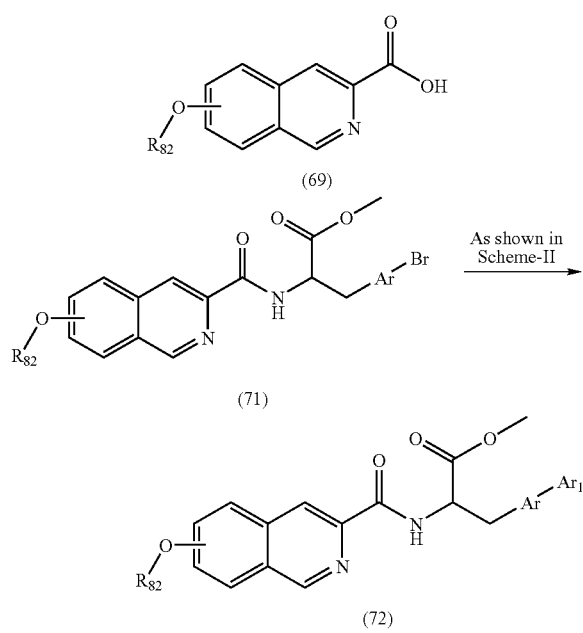

(69)

(71)

(72)

-continued

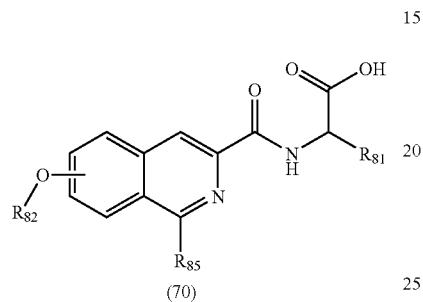

(73)

(74)

Scheme XVII describes synthesis of compounds of formula (79). $R_{85}$, $R_{82}$, and $R_8$ have the meanings as described for Scheme XIV. $PG_2$ represents a hydroxyl protecting group. An N-acylated amino acid ester (75) may be treated with a reagent such as oxalyl chloride in a solvent such as DCM, at a temperature of from 0° C. to 25° C., to afford a imidoyl chloride intermediate, which is treated with a reagent such as but not limited to $FeCl_3$ in DCM, followed by treatment with sulfuric acid in methanol to afford the cyclized product; concomitant removal of $PG_2$ (where $PG_2$ is tert-butyl or benzyl) may occur, to afford (76). Where $PG_2$ is not removed during these above steps, it may be removed, where $PG_2$ is tert-butyl, by treatment with TFA or HCl in dioxane. (76) may be dehydrogenated by treatment with Pd/C in xylene at a temperature of from 25° C. to 130° C., or by treatment with copper (II) acetate in DCM, to afford (77). The phenolic function of (77) may be functionalized as for Scheme XIV; as well, the product (78) after ester hydrolysis may be coupled with an amine or amino acid ester to give, after hydrolysis, the acid (79).

Scheme XVII

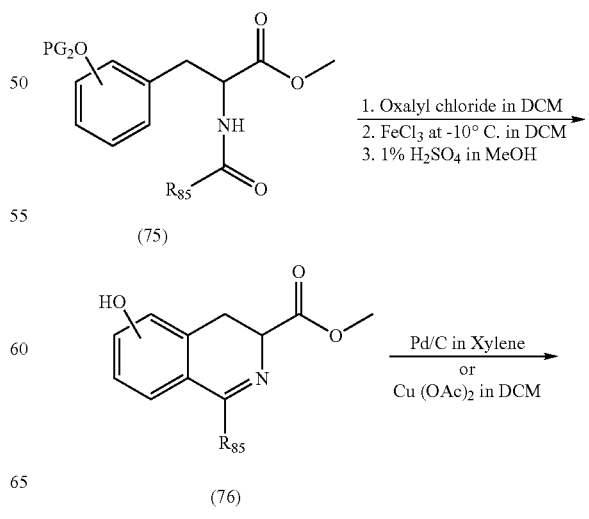

(75)

(76)

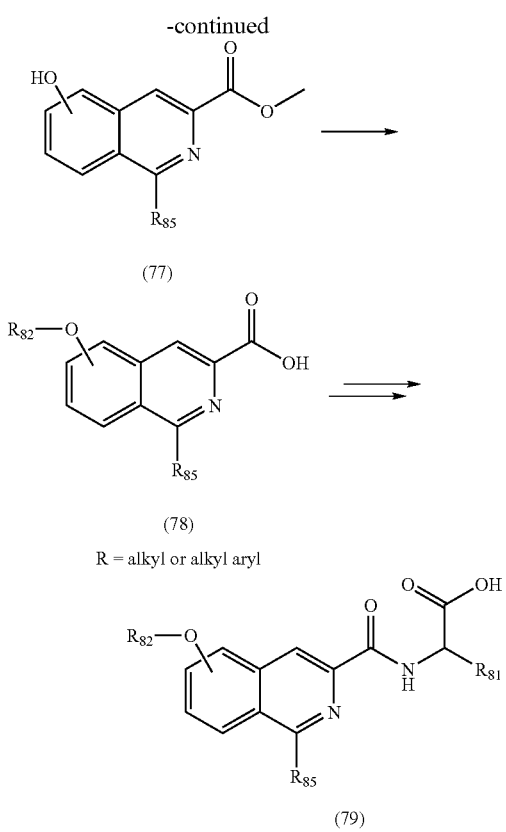

(77)

(78)

R = alkyl or alkyl aryl (79)

The term "amino-protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups.

The species of amino-protecting group employed is not critical so long as the derivatized amino group is stable to the condition of subsequent reaction(s) on other positions of the compound of Formula (I or X) and can be removed at the desired point without disrupting the remainder of the molecule. Commonly used amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. The related term "protected amino" or "protected amino group" defines an amino group substituted with an amino-protecting group discussed above.

The term "hydroxyl protecting group" as used herein refers to substituents of the alcohol group commonly employed to block or protect the alcohol functionality while reacting other functional groups on the compound. Examples of such alcohol-protecting groups include the 2-tetrahydropyranyl group, 2-ethoxyethyl group, the trityl group, the trichloroacetyl group, urethane-type blocking groups such as benzyloxycarbonyl, and the trialkylsilyl group, examples of such being trimethylsilyl, tert-butyldimethylsilyl, phenyldimethylsilyl, triiospropylsilyl and thexyldimethylsilyl. The choice of alcohol-protecting group employed is not critical so long as the derivatized alcohol group is stable to the condition of subsequent reaction(s) on other positions of the compound of the formulae and can be removed at the desired point without disrupting the remainder of the molecule. The related term "protected hydroxyl" or "protected alcohol" defines a hydroxyl group substituted with a hydroxy-protecting group as discussed above.

The term "carboxyl protecting group" as used herein refers to substituents of the carboxyl group commonly employed to block or protect the —OH functionality while reacting other functional groups on the compound. Examples of such alcohol-protecting groups include the 2-tetrahydropyranyl group, 2-ethoxyethyl group, the trityl group, the allyl group, the trimethylsilylethoxymethyl group, the 2,2,2-trichloroethyl group, the benzyl group, and the trialkylsilyl group, examples of such being trimethylsilyl, tert-butyldimethylsilyl, phenyldimethylsilyl, triiospropylsilyl and thexyldimethylsilyl. The choice of carboxyl protecting group employed is not critical so long as the derivatized alcohol group is stable to the condition of subsequent reaction(s) on other positions of the compound of the formulae and can be removed at the desired point without disrupting the remainder of the molecule. The related term "protected carboxyl" defines a carboxyl group substituted with a carboxyl-protecting group as discussed above.

Further examples of progroups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981.

The invention further provides pharmaceutical compositions comprising the factor XI or dual Factor IX/XI modulating compounds of the invention. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The term "factor IX" is used herein to refer to blood coagulation factor IX, including both activated and non-activated forms thereof.

The term "therapeutically effective amount" is used herein to denote that amount of a drug or pharmaceutical agent that will elicit the therapeutic response of an animal or human that is being sought.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Methanesulfonate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartrate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1–19.

Other salts which are not pharmaceutically acceptable may be useful in the preparation of compounds of the invention and these form a further aspect of the invention.

In addition, some of the compounds of Formula (I or X) may form solvates with water or common organic solvents. Such solvates are also encompassed within the scope of the invention.

Thus, in another aspect of the present invention, there is provided a pharmaceutical composition comprising a therapeutically effective amount of a compound of Formula (I or X), or a pharmaceutically acceptable salt, solvate, or prodrug thereof, and one or more pharmaceutically acceptable carriers, excipients, or diluents. In an embodiment of the pharmaceutical composition, the compound of Formula (I or X) is an antagonist of factor XI or an antagonist of factor IX/XI activity. In another embodiment of the pharmaceutical composition, the compound of Formula (I or X) is a partial antagonist of factor XI activity or of both factor XI/IX activity, wherein a partial antagonist comprises a compound that inhibits less than complete activity at a physiologically tolerable dose. In another embodiment of the pharmaceutical composition, the compound of Formula (I or X) is a partial antagonist of factor XI activity or of factor IX/XI activity, wherein the compound of Formula (I or X) inhibits up to 95% of factor IX or factor IX/XI activity. In another embodiment of the pharmaceutical composition, the compound of Formula (I or X) is a partial antagonist of factor XI activity or of factor IX/XI activity, wherein the compound of Formula (I or X) inhibits up to 80% of factor XI or factor IX/XI activity. In another embodiment of the pharmaceutical composition, the compound of Formula (I or X) is a partial antagonist of factor XI activity or of factor IX/XI activity, wherein the compound of Formula (I or X) inhibits up to 50% of factor XI or IX/XI activity. In another embodiment of the pharmaceutical composition, the compound of Formula (I or X) antagonizes blood clotting mediated by factor XI or IX/XI.

In another aspect of the present invention, there is provided a pharmaceutical composition comprising a therapeutically effective amount of a compound of Formula (I or X), or a pharmaceutically acceptable salt, solvate, or prodrug thereof, and one or more pharmaceutically acceptable carriers, excipients, or diluents, wherein said therapeutically effective amount of Formula (I or X) preferentially inhibits the intrinsic clotting cascade as compared to the extrinsic clotting cascade. In an embodiment of the pharmaceutical composition, said therapeutically effective amount of Formula (I or X) inhibits the intrinsic clotting cascade by greater than 80% and inhibits the extrinsic clotting cascade by less than 50%. In another embodiment of the pharmaceutical composition, said therapeutically effective amount of Formula (I or X) comprises an amount sufficient to achieve and maintain a sustained blood level that at least partially antagonizes factor XI or factor IX/XI biological activity. In another embodiment, said sustained blood level comprises a concentration ranging from about 0.01 µM to 2 mM. In another embodiment, said sustained blood level comprises a concentration ranging from about 0.05 µM to 100 µM. In another embodiment, said sustained blood level comprises a concentration ranging from about 0.1 µM to about 30 µM.

In another aspect of the present invention, there is provided a pharmaceutical composition comprising a therapeutically effective amount of a compound of Formula (I or X), or a pharmaceutically acceptable salt, solvate, or prodrug thereof, and one or more pharmaceutically acceptable carriers, excipients, or diluents, wherein said therapeutically effective amount comprises a sufficient amount of the compound of Formula (I or X) to at least partially inhibit the biological activity of factor XI or factor IX/XI in a subject, a sufficient amount of the compound of Formula (I or X) for at least partial amelioration of at least one factor XI- or factor IX/XI-mediated disease, or a sufficient amount of the compound of Formula (I or X) to at least partially inhibit the intrinsic clotting cascade in a subject. In an embodiment of the pharmaceutical composition, said factor XI- or factor IX/XI-mediated disease comprises stroke. In another embodiment of the pharmaceutical composition, said factor XI- or factor IX/XI-mediated disease comprises deep vein thrombosis. In another embodiment of the pharmaceutical composition, said factor XI- or factor IX/XI-mediated disease comprises deep vein thrombosis, wherein said thrombosis is associated with surgical procedures, long periods of confinement, acquired or inherited pro-coagulant states including anti-phospholipid antibody syndrome, protein C deficiency and protein S deficiency, or acute and chronic inflammation including recurrent miscarriage or Systemic Lupus Erythmatosis (SLE). In another embodiment, said factor XI- or factor IX/XI-mediated disease comprises excessive clotting associated with the treatment of kidney diseases by hemodialysis and/or venous hemofiltration. In another embodiment, said factor XI- or factor IX/XI-mediated disease comprises cardiovascular disease. In another embodiment, said factor XI- or factor IX/XI-mediated disease comprises cardiovascular disease, wherein said cardiovascular disease comprises myocardial infarction, arrhythmia, or aneurysm.

In another aspect, the present invention provides a pharmaceutical composition comprising a therapeutically effective amount of the compound of Formula (I or X), and one or more pharmaceutically acceptable carriers, excipients, or diluents, wherein said pharmaceutical composition is used to replace or supplement compounds that reduce clotting.

In another aspect, the present invention provides a pharmaceutical composition comprising a therapeutically effective amount of the compound of Formula (I or X), and one or more pharmaceutically acceptable carriers, excipients, or diluents, further comprising one or more therapeutic agents.

In another aspect, the present invention provides a method for the inhibition of the normal biological function of factor XI or factor IX/XI comprising administering to a subject in need thereof a compound of Formula (I or X). In embodiment of the method, said compound of Formula (I or X) is an antagonist of factor XI or factor IX/XI activity. In another embodiment of the method, said compound of Formula (I or X) antagonizes blood clotting mediated by factor XI or factor IX/XI. In another embodiment of the method, said compound of Formula (I or X) is administered in an amount sufficient to partially antagonize the biological activity of factor XI or factor IX/XI in said subject. In another embodiment of the method, said compound of Formula (I or X) is an antagonist of factor XI or factor IX/XI activity. In another embodiment of the method, said compound of Formula (I or X) antagonizes blood clotting mediated by factor XI or factor IX/XI. In another embodiment of the method, said compound of Formula (I or X) is administered in an amount sufficient to partially antagonize the biological activity of factor XI or factor IX/XI in said subject. In another embodiment of the method, said pharmaceutical composition is administered in the form of an oral dosage or parenteral dosage unit. In another embodiment of the method, said compound of Formula (I or X) is administered as a dose in a range from about 0.01 to 1,000 mg/kg of body weight per day. In another embodiment of the method, said compound of Formula (I or X) is administered as a dose in a range from about 0.1 to 100 mg/kg of body weight per day. In another embodiment of the method, said compound of Formula (I or X) is administered as a dose in a range from about 0.5 to 10 mg/kg of body weight per day. In another embodiment, said compound of Formula (I or X) is used to replace or supplement compounds that reduce clotting.

In another aspect, the present invention provides a method for the inhibition of the normal biological function of factor XI or factor IX/XI comprising administering to a subject in need thereof a compound of Formula (I or X), wherein said compound of Formula (I or X) is administered to said subject as a pharmaceutical composition comprising a therapeutically effective amount of said compound of Formula (I or X) and one or more pharmaceutically acceptable carriers, excipients, or diluents. In an embodiment of the method, said therapeutically effective amount of the compound of Formula (I or X) comprises a sufficient amount of the compound of Formula (I or X) to at least partially inhibit the intrinsic clotting cascade in said subject. In another embodiment of the method, said therapeutically effective amount of Formula (I or X) preferentially inhibits the intrinsic clotting cascade as compared to the extrinsic clotting cascade. In another embodiment of the method, said therapeutically effective amount of Formula (I or X) inhibits the intrinsic clotting cascade by greater than 80% and inhibits the extrinsic clotting cascade by less than 50%. In another embodiment of the method, said therapeutically effective amount of the compound of Formula (I or X) comprises an amount sufficient to achieve and maintain a sustained blood level that at least partially antagonizes factor XI or factor IX/XI biological activity. In another embodiment, said sustained blood level comprises a concentration ranging from about 0.01 μM to 2 mM. In another embodiment, said sustained blood level comprises a concentration ranging from about 0.05 μM to 100 μM In another embodiment, said sustained blood level comprises a concentration ranging from about 0.1 μM to about 30 μM. In another embodiment of the method, said pharmaceutical composition further comprises one or more therapeutic agents.

In another aspect, the present invention provides a method for the inhibition of the normal biological function of factor XI or factor IX/XI comprising administering to a subject in need thereof a compound of Formula (I or X), wherein said compound of Formula (I or X) is a partial antagonist of factor XI or factor IX/XI, wherein a partial antagonist comprises a compound that inhibits less than complete activity at a physiologically tolerable dose. In an embodiment of the method, said compound of Formula (I or X) inhibits up to 95% of factor XI or factor IX/XI activity. In another embodiment of the method, said compound of Formula (I or X) inhibits up to 80% of factor XI or factor IX/XI activity. In another embodiment of the method, said compound of Formula (I or X) inhibits up to 50% of factor XI or factor IX/XI activity.

In another aspect, the present invention provides a method for the inhibition of the normal biological function of factor XI or factor IX/XI comprising administering to a subject in need thereof a compound of Formula (I or X), wherein said compound of Formula (I or X) is administered to said subject as a pharmaceutical composition comprising a therapeutically effective amount of said compound of Formula (I or X) and one or more pharmaceutically acceptable carriers, excipients, or diluents, wherein said therapeutically effective amount of the compound of Formula (I or X) comprises a sufficient amount of the compound of Formula (I or X) for treatment or prevention of factor XI- or factor IX/XI-mediated diseases. In an embodiment of the method, said factor XI- or factor IX/XI-mediated disease comprises stroke. In another embodiment of the method, said factor XI- or factor IX/XI-mediated disease comprises deep vein thrombosis. The thrombosis may be associated with surgical procedures, long periods of confinement, acquired or inherited pro-coagulant states including anti-phospholipid antibody syndrome, protein C deficiency and protein S deficiency, or acute and chronic inflammation including recurrent miscarriage or Systemic Lupus Erythmatosis (SLE). In another embodiment of the method, said factor XI- or factor IX/XI-mediated disease comprises clotting associated with the treatment of kidney disease by hemodialysis and/or venous hemofiltration. In another embodiment of the method, said factor XI- or factor IX/XI-mediated disease comprises cardiovascular disease. The cardiovascular disease may be associated myocardial infarction, arrhythmia, or aneurysm.

In a further aspect of the present invention, the factor XI or dual factor IX/XI modulators of the invention are utilized in adjuvant therapeutic or combination therapeutic treatments with other known therapeutic agents.

The term "treatment" as used herein, refers to the full spectrum of treatments for a given disorder from which the patient is suffering, including alleviation of one, most of all symptoms resulting from that disorder, to an outright cure for the particular disorder or prevention of the onset of the disorder.

The following is a non-exhaustive listing of adjuvants and additional therapeutic agents which may be utilized in combination with the factor IXa antagonists of the present invention:

1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids In another embodiment, the present invention provides a method of treating or preventing a factor IXa mediated diseases, the method comprising administering to a subject in need thereof, a therapeutically effective amount of a compound of Formula (I or X) alone or in combination with therapeutic agents selected from the group consisting of antibiotics, hormones, biologic response modifiers, analgesics, NSAIDs, DMARDs, glucocorticoids, thrombolytic agents, antidepressants, and anticonvulsants.

The compound of Formula (I or X) of the present invention, may be administered at a dosage level of from about 0.01 to 1000 mg/kg of the body weight of the subject being treated. In another embodiment, The compound of Formula (I or X) of the present invention, may be administered at a dosage range between 0.01 and 100 mg/kg In another embodiment, the compound of Formula (I or X) of the present invention, may be administered at a dosage range between 0.5 to 10 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I or X) with an appropriate and convenient amount of carrier material which may vary from about 5 to 95 percent of the total composition. Dosage unit forms will generally contain between from about 5 mg to about 500 mg of active ingredient. This dosage may be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

The general procedures used in the methods of the present invention are described below.

Common names and definitions for resin reagents used in the disclosure are;
Merrifield p-Chloromethyl polystyrene
Hydroxy-Merrifieldp-Hydroxymethyl polystyrene
Wang(4-Hydroxymethyl)phenoxymethyl polystyrene
Wang carbonate4-(p-nitrophenyl carbonate)phenoxymethyl polystyrene
Rink Resin 4-(2',4'-Dimethoxyphenyl-Fmco-aminomethyl)-phenoxy polystyrene resin
Wang Bromo Resin (4-Bromomethyl)phenoxymethyl polystyrene
THP Resin 3,4-Dihydro-2H-pyran-2-yl methoxymethyl polystyrene
Aldehyde resin can refer to the following:
4-Benzyloxybenzaldehyde polystyrene
3-Benzyloxybenzaldehyde polystyrene
4-(4-Formyl-3-methoxyphenoxy)butyryl-aminomethyl polystyrene
2-(4-Formyl-3-methoxyphenoxy)ethyl polystyrene
2-(3,5-dimethoxy-4-formylphenoxy)ethoxy-methyl polystyrene
2-(3,5-dimethoxy-4-formylphenoxy)ethoxy polystyrene
(3-Formylindolyl)acetamidomethyl polystyrene
(4-Formyl-3-methoxyphenoxy) grafted (polyethyleneglycol)-polystyrene; or
(4-Formyl-3-methoxyphenoxy)methylpolystyrene.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate
d=day
DIAD=diisopropyl azodicarboxylate
DCC=dicyclohexylcarbodiimide
DCE=1,2-dichloroethane
DCM=dichloromethane
DIC=diisopropylcarbodiimide
DIEA=diisopropylethylamine
DMA=N,N-dimethylacetamide
DMAP=dimethylaminopyridine
DME=1,2 dimethoxyethane
DMF=N,N-dimethylformamide
DMPU=1,3-dimethypropylene urea
DMSO=dimethylsulfoxide
EDC=1-ethyl-3-(3-dimethylaminopropyl)-carbodiimide hydrochloride
EDTA=ethylenediamine tetraacetic acid
ELISA=enzyme-linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N,N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NMM=N-methylmorpholine, 4-methylmorpholine
NMR=nuclear magnetic resonance spectroscopy
p.o.=per oral PBS=phosphate buffered saline solution
PMA=phorbol myristate acetate
ppm=parts per million
psi=pounds per square inch
$R_f$=relative TLC mobility
rt=room temperature
s.c.=subcutaneous
SPA=scintillation proximity assay
TEA=triethylamine
TFA=trifluoroacetic acid
THF=tetrahydrofuran
THP=tetrahydropyranyl
TLC=thin layer chromatography
TMSBr=bromotrimethylsilane, trimethylsilylbromide
$T_r$=retention time General procedure A To a solution of a carboxylic acid (1.0 mmol) in DMF was added an amino acid methyl ester (1.2 mmol), HBTU (1.1 mmol), and DIEA (4.0 mmol) and the mixture was stirred overnight. After completion of the reaction, sufficient amount of water was added and the mixture was extracted with ethyl acetate. The organic layer was washed with water, brine, dried ($Na_2SO_4$), and concentrated under reduced pressure to afford the amide. The crude product was purified by flash chromatography (silica, Hexanes:EtOAc) to afford the pure product.

General Procedure B

To a mixture of phenol (1 mmol) and aryl or heteroaryl fluoride (2 mmol) in DMF was added solid potassium carbonate (5 mmol), and the mixture was heated at 80° C. for 12 h. After completion of the reaction, sufficient amount of water was added, and the mixture was extracted with ethyl acetate. The organic layer was washed with water, brine, dried ($Na_2SO_4$), and concentrated under reduced pressure to obtain crude product. The crude material obtained was purified by flash chromatography (silica, Hexanes:EtOAc) to afford the desired ether.

General Procedure C

To a solution of ester in THF—$CH_3OH$ (4:1), 2 N lithium hydroxide solution (5eq) was added, and the resulting reaction mixture was stirred at 0° C. for 30 minutes and then warmed to rt. After completion of the reaction the mixture was acidified with 2N HCl, extracted with ethyl acetate, the organic layer was washed with brine, dried over ($Na_2SO_4$), and the solvent was removed under reduced pressure to afford the product.

General Procedure D

To a solution of an aryl bromide or heteroaryl bromide (1 mmol) in DME or toluene were added a boronic acid (2 eq), $Pd(PPh_3)_4$ (ca. 10 mol %), 2N $Na_2CO_3$ solution (3 mmol). The mixture was heated at 75° C. for 12 h. After completion of the reaction, solvent was evaporated under reduced pressure and the residue was purified by column chromatography to provide the desired ester. The resulting ester was hydrolyzed as described in procedure C yielding the acid.

General Procedure E

To a solution of an aniline or amine (1.0 mmol) in DCE (10 mL) was added an aldehyde (2.0–2.2 mmol), acetic acid (3.0 mmol) and sodium triacetoxyborohydride (2.5 mmol) or sodium cyanoborohydride and the mixture was stirred overnight. After completion of the reaction, 50 mL of DCM was added and the organic layer was washed with saturated sodium bicarbonate solution and brine, and then dried over $Na_2SO_4$. The solvent was removed in vacuum to afford the product, which was purified by flash chromatography.

General Procedure F

To a solution of an aniline or amine (1.0 mmol) in DCM (10 mL) was added a sulfonyl chloride (1.0 mmol), pyridine (10.0 mmol), and the mixture was stirred overnight. After completion of the reaction, 50 mL of DCM was added and the organic layer was washed with 1N HCl, saturated sodium bicarbonate solution, and brine, and then dried over $Na_2SO_4$. The solvent was removed in vacuum to afford the sulfonamide, which was purified by flash chromatography.

General Procedure G

A flask was charged with phenol or aniline (1.0 equiv), $Cu(OAc)_2$ (1.0 equiv), arylboronic acid (1.0–3.0), and powdered 4 Å molecular sieves. The reaction mixture was diluted with $CH_2Cl_2$ to yield a solution approximately 0.1 M in phenol or aniline, and the $Et_3N$ (5.0 equiv) is added. After stirring the colored heterogeneous reaction mixture for 24 h at 25° C. under ambient atmosphere, the resulting slurry was filtered and the diaryl ether or diaryl amine was isolated from the organic filtrate by flash chromatography.

General Procedure H

To a solution of a phenol (1.0 mmol) in DMF (5 mL) was added an alkyl halide (1.2 mmol) (a catalytic amount of NaI is added for alkyl chlorides), and potassium carbonate (2.5 mmol) and the mixture heated at 70° C. overnight. After completion of the reaction, 5 mL of ethyl acetate and 5 mL of water was added. The organic layer was washed with water, and then dried over $Na_2SO_4$. The solvent was removed in vacuum to afford the ether, which was purified by flash chromatography.

General Procedure I

To a solution of ester in THF was added lithium hydroxide (3–4 eq), water, and methanol. The ratio of THF/water/methanol is 4:1:1. The reaction mixture was stirred at rt for 1–1.5 h. A 10% solution of citric acid was added to adjust the pH between 6–7. Ethyl acetate was added and the organic layer is separated. The aqueous layer was extracted with ethyl acetate twice. The combined organic layer was washed with brine, dried ($Na_2SO_4$), and concentrated under reduced pressure to give the product.

General Procedure J

To a stirring solution of an aniline (2 mmol) dissolved in DCM containing pyridine (4 mmol) was added acid chloride (2.5 mmol) at 0° C. The reaction mixture was stirred at rt for 3 h, extracted with DCM, washed with 1M HCl and brine, and evaporation followed by column chromatography purification gave the amide.

General Procedure K

To a stirring solution of amine or aniline (1 mmol) dissolved in DCM containing triethyl amine (4 mmol), was added a chloroformate (1.5 mmol) at rt. The reaction mixture was stirred for 1–1.5 h. The reaction mixture was concentrated and purified by chromatography to give the carbamate.

General Procedure L

To a stirring solution of amine or aniline (1 mmol) dissolved in DCM containing DIEA (4 mmol) was added an isocyanate (1.5 mmol) at rt. The reaction mixture was stirred for 1–1.5 h. The reaction mixture was concentrated and purified by chromatography to give the urea.

General Procedure M

A solution of an aryl bromide or heteroaryl bromide (1 mmol) and Pd(PPh$_3$)$_4$ (10 mol %) in anhydrous dioxane was degassed by bubbling N$_2$ gas into the solution for 10 min. To this was added alkenyl tin (1.2 mmol) and the solution was degassed for an additional 10 min and then heated at 80° C. overnight under N$_2$ atmosphere. The reaction was cooled to rt and KF solution was added and the reaction mixture was stirred for 30 min. The precipitated solid was filtered and the solid residue on the filter funnel was washed with copious amounts ethyl acetate to strip the product. The filtrate was concentrated and purified by flash column chromatography (silica, Hex:EtOAc) to provide the corresponding coupled product. This was hydrolyzed as described in the general procedure C to yield the acid.

General Procedure N

To a solution of an alkene in anhydrous methanol or ethyl acetate was added Pd/C (10 wt %) and the reaction was stirred for 2–18 h under an atmosphere of H$_2$ gas (1 atm). For some alkene substrates, the reaction was performed under 3–4 atm pressure of H$_2$ gas. The reaction mixture was filtered on a celite pad and washed with methanol. The filtrate was concentrated under reduced pressure to afford the desired reduced product.

The above general methods are for illustration only. Alternate conditions that may optionally be used include: Use of alternative solvents, alternative stoichiometries of reagents, alternative reaction temperatures and alternative methods of purification.

EXAMPLES

LC-MS data was obtained using gradient elution on a parallel MUX™ system, running four Waters 1525 binary HPLC pumps, equipped with a Mux-UV 2488 multichannel UV-Vis detector (recording at 215 and 254 nM) and a Leap Technologies HTS PAL Auto sampler using a Sepax GP-C18 4.6×50 mm column. A three minute gradient was run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. All MS data was obtained in the positive mode unless otherwise noted. 1H NMR data was obtained on a Varian 400 MHz spectrometer.

Example E-1

7-(4-tert-Butyl-phenoxy)-1-cyclopentylmethyl-isoquinoline-3-carboxylic acid

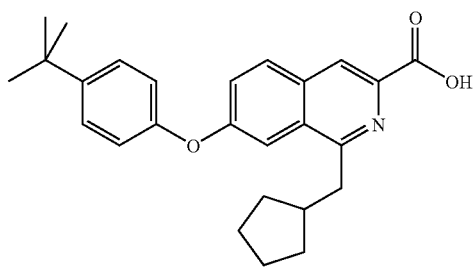

To a stirring of solution of H-Tyr(O-tert-Bu)-OMe HCl (15 g, 52.1 mmol), NEt$_3$ (13.1 g, 129.7 mmol) in 400 mL of DCM at 0° C. was added cyclopentyl acetyl chloride (8.4 g, 57.3 mmol). The reaction mixture was warmed to rt and stirring was continued for 45 min. Then the organic layer was washed with water, 1.0 N HCl and brine then dried over Na$_2$SO$_4$. Evaporation of the solvent gave 19 g of amide, which was used for further step without purification.

LCMS: 438 (M+1)$^+$

To a stirring solution of above amide (19 g, 52.1 mmol) in 400 mL of anhydrous DCM at 0° C. was added oxalyl chloride (7.9 g, 63.1 mmol). The reaction mixture was brought to rt and stirring continued for another one hour. Then the reaction mixture was cooled to −10° C. and to it anhydrous FeCl$_3$ (10.1 g, 62.3 mmol) was added portion wise. The stirring was continued for 12 h at rt and the reaction mixture was treated with 200 mL of 2.0 M HCl for 2 h. The organic layer was separated washed with water and brine, dried over Na$_2$SO$_4$ and concentrated under reduced pressure. Methanol (400 mL) and conc. H$_2$SO$_4$ (10 mL) was added to the foamy residue and reaction was heated to reflux for 12 h, methanol was evaporated and the crude product was extracted with ethyl acetate (2×100 mL). The aqueous layer was basified with NH$_4$OH (pH>9) and extracted with DCM (2×100 mL). The organic layer was washed with water and brine and dried over Na$_2$SO$_4$ evaporation of the solvent gave 7.0 g of 1-cyclopentylmethyl-7-hydroxy-3,4-dihydroisoquinoline-3-carboxylic acid methyl ester.

LCMS: 288 (M+1)$^+$

The above compound (7 g, 24.3 mmol) was dissolved in 200 mL of DCM, then, 8.8 g (48.6 mmol) of copper (II) acetate and 12.3 g (121 mmol) of NEt$_3$ was added. The resulting mixture was stirred at rt for 2.0 h, filtered, and the filtrate was concentrated followed by column chromatography using ethyl acetate and hexane to give 6.6 g of 1-cyclopentylmethyl-7-hydroxy-isoquinoline-3-carboxylic acid methyl ester.

LCMS: 286 (M+1)$^+$ 3.0 g (10.5 mmol) of above phenol, 2.7 g (15.7 mmol) of 4-tert-butyl phenylboronic acid, 1.9 g (10.5 mmol) of copper (II) acetate and 1 g of crushed 4 Å molecular sieves were taken up in 115 mL of DCM. To this stirring solution 5.3 g (115 mmol) of NEt$_3$ was added and stirring was continued for 12 h. Filtration and evaporation of the solvent followed by column chromatography using hexane and ethyl acetate as eluant gave 1.5 g of 7-(4-tert-butyl-phenoxy)-1-cyclopentylmethyl-isoquinoline-3-carboxylic acid methyl ester.

LCMS: 418 (M+1)$^+$

To a stirring solution of 1.5 g (3.6 mmol) of ester in 9.0 mL of THF and 2.16 mL of MeOH was added 2.16 mL of 2 N LiOH at rt. Stirring was continued for 30 min and the mixture was acidified with 1.0 N HCl (pH=~3) and extracted with 2×25 mL of ethyl acetate. The organic layer was dried over anhydrous sodium sulfate and concentrated to give 1.37 g of title compound as a light yellow solid.

$^1$H-NMR (400 MHZ, CDCl$_3$): δ 8.47 (s, 1H), 7.98 (d, 1H), 7.59 (s, 1H), 7.53 (dd, 1H), 7.46 (d, 2H), 7.05 (d, 2H), 3.15 (d, 2H), 2.35 (m, 1H), 1.67 (m, 4H), 1.53 (m, 2H), 1.36 (s, 9H), 1.30 (m, 2H). LCMS: 404 (M+1)$^+$

Example E-2

3-(5-bromo-thiophene-2-yl)-2(S)-{[7-(4-tert-Butyl-phenoxy)-1-cyclopentylmethyl-isoquinoline-3-carbonyl]-amino}-propionic acid methyl ester

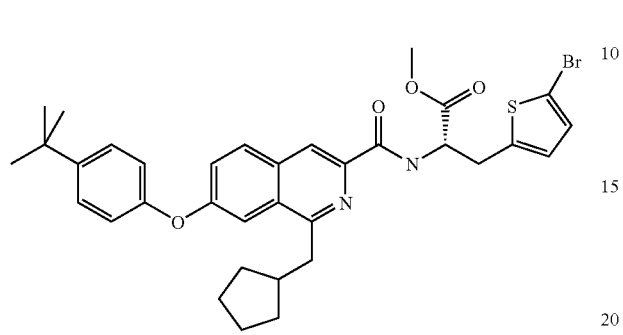

The title compound was prepared by treatment of Compound E-1 with (2S)-amino-3-(5-bromo-thiophen-2-yl)-propionic acid methyl ester HCl prepared from commercially available (2S)-amino-3-(5-bromo-thiophen-2-yl)-propionic acid according to general procedure A.

Example E-3

7-(trans-4-tert-Butyl-cyclohexyloxy)-1-cyclopentyl-methyl-isoquinoline-3-carboxylic acid

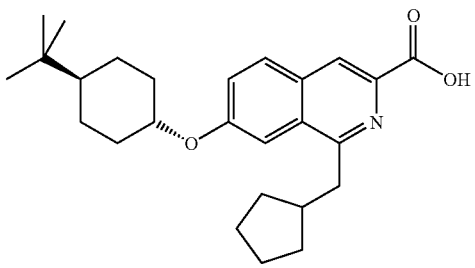

0.7 g (2.5 mmol) of 1-cyclopentylmethyl-7-hydroxy-isoquinoline-3-carboxylic acid methyl ester (prepared in example E-1), 3.0 g (5.0 mmol) of triphenyl phosphine polystyrene resin (1.10 mmol/g) and 0.42 g (2.7 mmol) of cis-4-tert-butylcyclohexanol were taken in 25 mL of DCM. To this was added DIAD (0.6 g, 3.0 mmol) at 0° C. The reaction mixture was shaken for 2 h. Filtration and evaporation of the solvent followed by column chromatography using hexane/ethyl acetate gave 0.75 g of product, which was hydrolyzed as described in general procedure C to afford 669 mg of the title compound as a light yellow solid.

LCMS: 410 (M+1)+

Example E-4

6-(4-tert-Butyl-phenoxy)-1-cyclopentylmethyl-isoquinoline-3-carboxylic acid

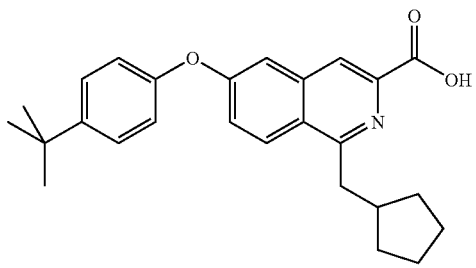

12.5 g (54.3 mmol) of 2-amino-3-(3-hydroxy-phenyl)-propionic acid methyl ester was reacted with cyclopentyl acetic acid (6.97 g, 54.3 mmol) as described in general procedure A. The compound was purified using gradient elution with ethyl acetate in hexanes to yield 9.1 g of 2-(2-cyclopentyl-acetylamino)-3-(3-hydroxy-phenyl)-propionic acid methyl ester.

LCMS 307 (M+1)+.

A portion of the material from the previous step (4.0 g, 13.1 mmol) was dissolved in 120 mL anhydrous DCM, and to this was added 4-tert-butylphenyl boronic acid (2.0 eq., 26.2 mmol, 4.66 g), copper (II) acetate (1.1 eq., 14.4 mmol, 2.62 g), and 2.0 g of powdered 4 Å molecular sieves. To the stirring mixture was added triethylamine (3.0 eq., 39.3 mmol, 5.5 mL) and the reaction carried out according to general procedure G. Chromatographic purification on silica eluting with ethyl acetate in hexanes afforded 2.50 g of 3-[3-(4-tert-butyl-phenoxy)-phenyl]-2-(2-cyclopentyl-acetylamino)-propionic acid methyl ester.

LCMS: 439 (M+1)+.

1.77 g (4.07 mmol) of 3-[3-(4-tert-butyl-phenoxy)-phenyl]-2-(2-cyclopentyl-acetylamino)-propionic acid methyl ester was dissolved in 40 mL anhydrous toluene and phosphoryl chloride was added and the mixture heated at 90° C. for several hours and then cooled. The solvent and excess reagent was removed and the residue was purified via column chromatography on silica eluting with 20–30% ethyl acetate in hexanes to afford 380 mg of the cyclized product, 6-(4-tert-butyl-phenoxy)-1-cyclopentylmethyl-3,4-dihydro-isoquinoline-3-carboxylic acid methyl ester.

LCMS 421 (M+1)+.

The product of the previous reaction (380 mg, 0.91 mmol) was dissolved in 9 mL dry DCM and triethylamine (5.0 eq., 4.53 mmol, 0.63 mL) and copper (II) acetate (2.2 eq., 1.99 mmol, 362 mg) was added and the mixture stirred at rt for several hours. The solution was concentrated and purified via column chromatography on silica eluting with ethyl acetate /hexanes to afford 378 mg of 6-(4-tert-butyl-phenoxy)-1-cyclopentylmethyl-isoquinoline-3-carboxylic acid methyl ester.

LCMS 419 (M+1)+.

The above material was taken in its entirety (378 mg, 0.905 mmol) and hydrolyzed according to general procedure C to afford the title compound as a white solid (365 mg).

LCMS 405 (M+1)+.

Example E-5

2(R)-Amino-3-(5-isopropyl-thiophen-2-yl)-propionic acid methyl ester HCl

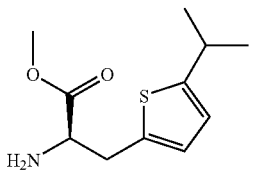

To a suspension of (2R)-amino-3-(5-bromo-thiophen-2-yl)-propionic acid methyl ester HCl (14.0 g, 46.59 mmol) (prepared from commercially available (2R)-amino-3-(5-bromo-thiophen-2-yl)-propionic acid) in DCM (250 mL) was added NaHCO$_3$ (9.78 g, 116.49 mmol), water (100 mL). The solution was stirred for 10 min and Boc-anhydride (12.20 g, 55.91 mmol) was added. The reaction was stirred overnight. The organic layer was separated and washed with brine, dried (Na$_2$SO$_4$) and concentrated under reduced pressure to give 17.0 g of 3-(5-bromo-thiophen-2-yl)-2(R)-tert-butoxycarbonylamino-propionic acid methyl ester.

15.0 g (41.17 mmol) of 3-(5-bromo-thiophen-2-yl)-2(R)-tert-butoxycarbonylamino-propionic acid methyl ester was treated with tributyl-isopropenyl-stannane (17.88 g, 54.07 mmol) and Pd(PPh$_3$)$_4$ (4.8 g, 4.15 mmol) as described in the general procedure M to afford 8.50 g of 2(R)-tert-butoxycarbonylamino-3-(5-isopropenyl-thiophen-2-yl)-propionic acid methyl ester.

8.50 g of 2(R)-tert-butoxycarbonylamino-3-(5-isopropenyl-thiophen-2-yl)-propionic acid methyl ester was treated with Pd/C and H$_2$ gas (1 atm) by the general procedure N to afford 8.20 g of 2(R)-tert-butoxycarbonylamino-3-(5-isopropyl-thiophen-2-yl)-propionic acid methyl ester. This ester was treated with HCl/dioxane (4.0 M) to afford 7.10 g of title compound.

Example E-6

2(S)-Amino-3-(5-isopropyl-thiophen-2-yl)-propionic acid methyl ester HCl

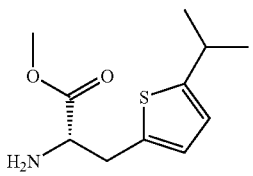

The title compound was prepared by analogous procedure used to prepare Compound E-5.

Example E-7

7-(4-tert-Butyl-phenoxy)-1-(tetrahydro-pyran-4-yl)-isoquinoline-3-carboxylic acid

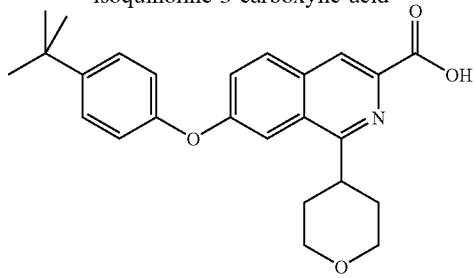

The title compound was synthesized by analogous procedure used to prepare Compound E-1 with the exception that tetrahydro-pyran-4-carbonyl chloride was used instead of cyclopentylacetyl chloride.

Example E-8

1-Cyclopentylmethyl-7-(4-isopropyl-cyclohexyloxy)-isoquinoline-3-carboxylic acid

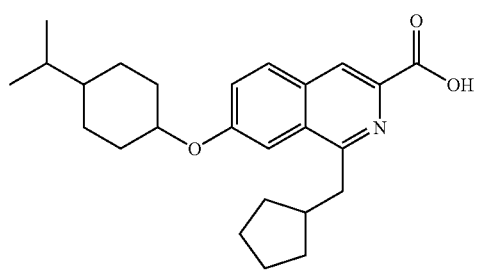

To a solution of Compound E-1 (1.0 mmol) in THF was added 4-isopropyl cyclohexanol (1.5 mmol), triphenyl phosphine polystyrene resin 1.10 mmol/g, 2.50 mmol), and DIAD (2 mmol) at 0° C. The reaction was warmed to rt and stirred for 4 h. The reaction mixture was filtered and concentrated. The crude product was purified by flash column chromatography (silica, Hexanes/EtOAc to afford 1-cyclopentylmethyl-7-(4-isopropyl-cyclohexyloxy)-isoquinoline-3-carboxylic acid methyl ester. This ester was hydrolyzed by the general procedure C to afford the title compound.

Example E-9

1-Cyclopentylmethyl-7-(4-trans-ethyl-cyclohexyloxy)-isoquinoline-3-carboxylic acid

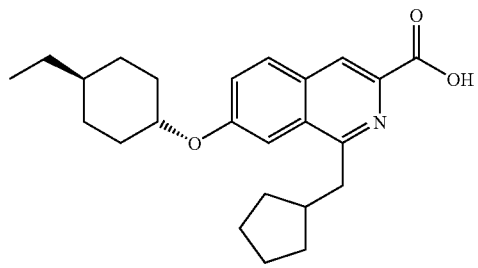

The title compound was prepared by analogous procedure used to prepare Compound E-8 with the exception that 4-Cis-4-ethyl-cyclohexanol was used.

Example E-10

7-(4-tert-Butylphenoxy)-isoquinoline-3-carboxylic acid

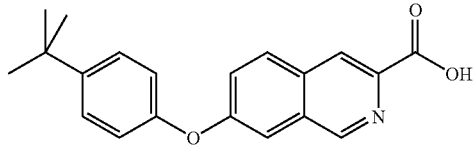

To a solution of (3S)-7-hydroxy-3,4-dihydro-1H-isoquinoline-2,3-dicarboxylic acid 2-tert-butyl ester (1.47 g, 5.0 mmol) in dry DMF (25 mL) at ambient temperature, was added iodomethane (1.2 eq., 6.0 mmol, 0.37 mL) and diisopropylethylamine (1.5 eq. 7.5 mmol, 1.31 mL) in succession, and the reaction mixture was stirred at rt for 3-4 hours, at which point LC/MS analysis showed the presence of product. The reaction mixture was poured into 50 mL of water and extracted with DCM (3×50 mL) and the combined DCM extracts were washed with water (3×50 mL) and brine (50 mL), dried over $Na_2SO_4$, filtered and concentrated under reduced pressure. The crude product was purified by flash column chromatography on silica (ethyl acetate/hexanes) to afford (3S)-7-hydroxy-3,4-dihydro-1H-isoquinoline-2,3-dicarboxylic acid 2-tert-butyl ester 3-methyl ester (1.13 g).

LCMS: 308 (M+1)$^+$.

The above phenol (1.20 g, 3.91 mmol) was reacted with 4-(tert-butyl)phenylboronic acid (1.6 eq., 6.26 mmol, 1.11 g), copper (II) acetate (1.0 eq. 3.91 mmol, 710 mg) as described in general procedure G. Flash column chromatography on silica (ethyl acetate/hexanes) provided 750 mg of the desired product, (3S)-7-(4-tert-butylphenoxy)-3,4-dihydro-1H-isoquinoline-2,3-dicarboxylic acid 2-tert-butyl ester 3-methyl ester.

LCMS: 440 (M+1)$^+$

A portion of the material described above (400 mg, 0.91 mmol) was placed in a dry 4 dram vial containing a magnetic stir bar, and was treated with a 4N solution of anhydrous HCl in 1,4-dioxane (1.0 mL, 4.0 mmol, 4.4 eq). The reaction was stirred at ambient temperature for 1 hour, until complete by TLC. The solvent and residual HCl was removed under vacuum and the crude product, (3S)-7-(4-tert-butylphenoxy)-1,2,3,4-tetrahydroisoquinoline-3-carboxylic acid methyl ester hydrochloride, was used without further purification.

LCMS: 340 (M+1)$^+$

The above crude product was dissolved in 18 mL of dry toluene and DDQ (3.0 eq., 2.73 mmol, 620 mg) was added in a single portion. The mixture was heated at reflux for 2 hours then cooled to rt and concentrated under reduced pressure. The crude residue was placed directly atop a silica gel column and eluted with a mixture of ethyl acetate and hexanes to furnish 229 mg of, 7-(4-tert-butylphenoxy)-isoquinoline-3-carboxylic acid methyl ester. A portion of the ester (208 mg, 0.62 mmol) was hydrolyzed as described in general procedure C to afford 199 mg of the title compound as a white solid.

$^1$H-NMR (400 MHZ, CDCl$_3$): δ 8.47 (s, 1H), 7.98 (d, 1H), 7.59 (s, 1H), 7.53 (dd, 1H), 7.46 (d, 2H), 7.05 (d, 2H), 3.15 (d, 2H), 2.35 (m, 1H), 1.67 (m, 4H), 1.53 (m, 2H), 1.36 (s, 9H), 1.30 (m, 2H). LCMS: 322 (M+1)$^+$.

Example E-11

[(5-Bromo-thiophen-2-ylmethyl)-amino]-acetic acid tert-butyl ester

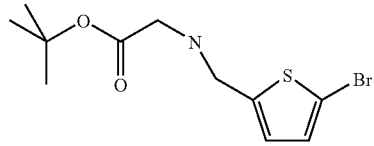

The title compound was prepared by treatment of 5-bromo-thiophene-2-carboxyaldehyde with amino-acetic acid tert-butyl ester by the general procedure E.

Example E-12

[(5-Bromo-thiophen-2-ylmethyl)-amino]-acetic acid methyl ester

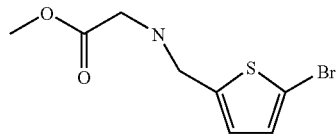

The title compound was prepared by treatment of 5-bromo-thiophene-2-carboxyaldehyde with amino-acetic acid methyl ester by the general procedure E.

Example E-13

[(4-Bromo-thiophen-2-ylmethyl)-amino]-acetic acid methyl ester

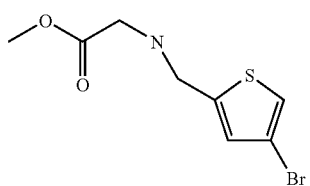

The title Compound was prepared by treatment of 4-bromo-thiophene-2-carboxyaldehyde with amino-acetic acid methyl ester by the general procedure E.

Example E-14

[(5-Methyl-thiophen-2-ylmethyl)-amino]-acetic acid methyl ester

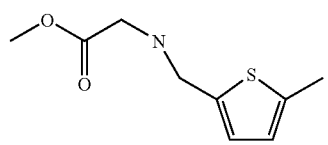

The title compound was prepared by treatment of 5-methyl-thiophene-2-carboxyaldehyde with amino-acetic acid methyl ester by the general procedure E.

Example 1

2(S)-{[7-(4-tert-Butyl-phenoxy)-1-cyclopentylmethyl-isoquinoline-3-carbonyl]-amino}-3-(5-phenylthiophen-2-yl)-propionic acid The title compound was prepared by treatment of Compound E-2 with phenyl boronic acid by the general procedure D to afford 2(S)-{[7-(4-tert-Butyl-phenoxy)-1-cyclopentylmethyl-isoquinoline-3-carbonyl]-amino}-3-(5-phenylthiophen-2-yl)-propionic acid methyl ester. The ester was hydrolyzed by the general procedure C to afford the title compound.
LCMS: 624 (M+1)$^+$

Example 2

2(S)-{[7-(4-tert-Butyl-phenoxy)-1-cyclopentylmethyl-isoquinoline-3-carbonyl]-amino}-3-[5-(4-trifluoromethyl-phenyl)thiophen-2-yl]-propionic acid The title compound was prepared by treatment of Compound E-2 with 4-trifluorophenylboronic acid by the general procedure D to yield 2(S)-{[7-(4-tert-Butyl-phenoxy)-1-cyclopentylmethyl-isoquinoline-3-carbonyl]-amino}-3-[5-(4-trifluoromethyl-phenyl)thiophen-2-yl]-propionic acid methyl. The ester was hydrolyzed by the general procedure C to obtain the title compound.
LCMS: 702 (M+1)$^+$

Example 3

2(S)-{[7-(4-tert-Butyl-phenoxy)-1-cyclopentylmethyl-isoquinoline-3-carbonyl]-amino}-3-(5-cyclopent-1-enyl-thiophen-2-yl)-propionic acid methyl ester The title compound was prepared by treatment of Compound E-2 with cyclopenten-1-ylboronic acid by the general procedure D.
LCMS: 638 (M+1)$^+$

Example 4

2(S)-{[7-(4-tert-Butyl-phenoxy)-1-cyclopentylmethyl-isoquinoline-3-carbonyl]-amino}-3-(5-cyclopent-1-enyl-thiophen-2-yl)-propionic acid Example 3 was hydrolyzed by the general procedure C to obtain the title compound.
LCMS: 624 (M+1)$^+$

Example 5

2(S)-{[7-(4-tert-Butyl-phenoxy)-1-cyclopentylmethyl-isoquinoline-3-carbonyl]-amino}-3-(5-cyclopentyl-thiophen-2-yl)-propionic acid methyl ester The title compound was prepared by the treatment of Example 3 with Pd/C and H$_2$ gas (1 atm) by the general procedure N.
LCMS: 640 (M+1)$^+$

Example 6

2(S)-{[7-(4-tert-Butyl-phenoxy)-1-cyclopentylmethyl-isoquinoline-3-carbonyl]-amino}-3-(5-cyclopentyl-thiophen-2-yl)-propionic acid The title compound was prepared by hydrolysis of Example 5 by the general procedure C.
LCMS: 626 (M+1)$^+$

Example 7

2(S)-{[7-(4-tert-Butyl-phenoxy)-1-cyclopentylmethyl-isoquinoline-3-carbonyl]-amino}-3-(5-furan-3-yl-thiophen-2-yl)-propionic acid The title compound was prepared by treatment of Compound E-2 with furan-3-boronic acid to afford 2(S)-{[7-(4-tert-Butyl-phenoxy)-1-cyclopentylmethyl-isoquinoline-3-carbonyl]-amino}-3-(5-furan-3-yl-thiophen-2-yl)-propionic acid methyl ester. The ester was hydrolyzed by the general procedure C to obtain the title compound.
LCMS: 624 (M+1)$^+$

Example 8

2(S)-{[7-(4-tert-Butyl-phenoxy)-1-cyclopentylmethyl-isoquinoline-3-carbonyl]-amino}-3-[5-(4-isopropyphenyl)-thiophen-2-yl]proprionic acid The title compound was prepared by treatment of Compound E-2 with 4-isopropylphenylboronic acid to yield 2(S)-{[7-(4-tert-Butyl-phenoxy)-1-cyclopentylmethyl-isoquinoline-3-carbonyl]-amino}-3-[5-(4-isopropyphenyl)-thiophen-2yl]proprionic acid methyl ester. The ester was hydrolyzed by the general procedure C to afford the title compound.
LCMS: 676 (M+1)$^+$

Example 9

2(S)-{[7-(4-tert-Butyl-phenoxy)-1-cyclopentylmethyl-isoquinoline-3-carbonyl]-amino}-3-(5-vinyl-thiophen-2-yl)-propionic acid The title compound was prepared by treatment of Compound E-2 with tributyl vinyl stannane and Pd(PPh$_3$)$_4$ by the general procedure M to afford 2(S)-{[7-(4-tert-Butyl-phenoxy)-1-cyclopentylmethyl-isoquinoline-3-carbonyl]-amino}-3-(5-vinylthiophen-2-yl)-propionic acid methyl ester. The ester was hydrolyzed by the general procedure C to afford the title compound.
LCMS: 584 (M+1)$^+$

Example 10

2(S)-{[7-(4-tert-Butyl-phenoxy)-1-cyclopentylmethyl-isoquinoline-3-carbonyl]-amino}-3-(5-p-tolyl-thiophen-2-yl)-propionic acid The title compound was prepared by treatment of Compound E-2 with 4-methylphenylboronic acid by the general procedure D to afford 2(S)-{[7-(4-tert-Butyl-phenoxy)-1-cyclopentylmethyl-isoquinoline-3-carbonyl]-amino}-3-(5-p-tolyl-thiophen-2-yl)-propionic acid methyl ester. The ester was hydrolyzed by the general procedure C to afford the title compound.

LCMS: 648 (M+1)$^+$

Example 11

2(S)-{[7-(4-tert-Butyl-phenoxy)-1-cyclopentylmethyl-isoquinoline-3-carbonyl]-amino}-3-[5-(4-chloro-phenyl)-thiophen-2-yl]-propionic acid The title compound was prepared by treatment of Compound E-2 with 4-chlorophenylboronic acid by the general procedure D to afford 2(S)-{[7-(4-tert-Butyl-phenoxy)-1-cyclopentylmethyl-isoquinoline-3-carbonyl]-amino}-3-[5-(4-chloro-phenyl)-thiophen-2-yl]-propionic acid methyl ester. The ester was hydrolyzed by the general procedure C to afford the title compound.

LCMS: 668 (M+1)$^+$

Example 12

2(S)-{[7-(4-tert-Butyl-phenoxy)-1-cyclopentylmethyl-isoquinoline-3-carbonyl]-amino}-3-(5-ethyl-thiophen-2-yl)-propionic acid The title compound was prepared by the treatment of Example 9 with Pd/C and H$_2$ (1 atm) by the general procedure N.

LCMS: 586 (M+1)$^+$

Example 13

2(S)-{[7-(4-tert-Butyl-phenoxy)-1-cyclopentylmethyl-isoquinoline-3-carbonyl]-amino}-3-furan-2-yl-propionic acid Compound E-1 (0.050 g (0.012 mmol) was reacted with (2S)-amino-3-furan-2-yl-propionic acid methyl ester HCl (0.038 g, 0.018 mmol, prepared from commercially available (2S)-amino-3-furan-2-yl-propionic acid) as described in general procedure A to afford 0.066 g of 2(S)-{[7-(4-tert-Butyl-phenoxy)-1-cyclopentylmethyl-isoquinoline-3-carbonyl]-amino}-3-furan-2-yl-propionic acid methyl ester.

The resulting ester was hydrolyzed by the general procedure C to afford 0.060 g of the title compound.

LCMS: 542 (M+1)$^+$

Example 14

2(S)-{[7-(4-tert-Butyl-phenoxy)-1-cyclopentylmethyl-isoquinoline-3-carbonyl]-amino}-3-(2-trifluoromethyl-phenyl)-propionic acid The title compound was prepared by analogous procedure used to prepare Example 13 with the exception that 2(S)-Amino-3-(2-trifluoromethyl-phenyl)-propionic acid methyl ester HCl (prepared from commercially available 2(S)-Amino-3-(2-trifluoromethyl-phenyl)-propionic acid) was used.

The resulting ester was hydrolyzed by the general procedure C to afford the title compound.

LCMS: 620 (M+1)$^+$

Example 15

{(5-Bromo-thiophen-2-ylmethyl)-[7-(4-tert-butyl-phenoxy)-1-cyclopentylmethyl-isoquinoline-3-carbonyl]-amino}-acetic acid tert-butyl ester Compound E-11 (0.060 g, 0.195 mmol) was treated with Compound E-1 (0.079 g, 0.195 mmol) by the general procedure A to afford 36 mg of the title compound.

LCMS: 693 (M+1)$^+$

Example 16

2(S)-{[7-(4-tert-Butyl-phenoxy)-1-cyclopentylmethyl-isoquinoline-3-carbonyl]-amino}-3-(3,5-difluorophenyl-propionic acid The title compound was prepared by analogous procedure used to prepare Example 13 with the exception that 2(S)-Amino-3-(3,5-difluorophenyl)-propionic acid methyl ester HCl (prepared from commercially available 2(S)-Amino-3-(3,5-difluorophenyl)-propionic acid) was used.

The resulting ester was hydrolyzed by the general procedure C to afford the title compound.

LCMS: 588 (M+1)$^+$

Example 17

[[7-(4-tert-butyl-phenoxy)-1-cyclopentylmethyl-isoquinoline-3-carbonyl]-(5-methyl-thiophen-2-ylmethyl)-amino]-acetic acid Compound E-14 was treated with Compound E-1 by the general procedure A to yield [[7-(4-tert-butyl-phenoxy)-1-cyclopentylmethyl-isoquinoline-3-carbonyl]-(5-methyl-thiophen-2-ylmethyl)-amino]-acetic acid methyl ester, which upon hydrolysis by the general procedure C gave the title compound.

LCMS: 572 (M+1)$^+$

Example 18

{(5-Bromo-thiophen-2-ylmethyl)-[7-(4-tert-butyl-phenoxy)-1-cyclopentylmethyl-isoquinoline-3-carbonyl]-amino}-acetic acid methyl ester Compound E-12 was treated with Compound E-1 by the general procedure E to afford the title compound.

LCMS: 651 (M+1)$^+$

Example 19

{(4-Bromo-thiophen-2-ylmethyl)-[7-(4-tert-butyl-phenoxy)-1-cyclopentylmethyl-isoquinoline-3-carbonyl]-amino}-acetic acid Compound E-13 was treated with Compound E-1 by the general procedure A to yield {(4-Bromo-thiophen-2-ylmethyl)-[7-(4-tert-butyl-phenoxy)-1-cyclopentylmethyl-isoquinoline-3-carbonyl]-amino}-acetic acid methyl ester which upon hydrolysis by the general procedure C gave the title compound.

LCMS: 637 (M+1)$^+$

Example 20

{(5-Bromo-thiophen-2-ylmethyl)-[7-(4-tert-butyl-phenoxy)-1-cyclopentylmethyl-isoquinoline-3-carbonyl]-amino}-acetic acid Example 18 was hydrolyzed by the general procedure C to afford the title compound.
LCMS: 637 (M+1)$^+$

Example 21

Benzo[b]thiophen-3-yl-{[7-(4-tert-butyl-phenoxy)-1-cyclopentylmethyl-isoquinoline-3-carbonyl]-amino}-acetic acid The title compound was prepared by analogous procedure used to prepare Example 13 with the exception that amino-benzo[b]thiophen-3-yl-acetic acid methyl ester HCl (obtained from commercially available amino-benzo[b]thiophen-3-yl-acetic acid) was used.
The resulting ester was hydrolyzed by the general procedure C to afford the title compound.
LCMS: 594 (M+1)$^+$

Example 22

2(S)-{[7-(4-tert-butyl-phenoxy)-1-cyclopentylmethyl-isoquinoline-3-carbonyl]-amino}-3-(4-fluoro-phenyl)-propionic acid The title compound was prepared by analogous procedure use to prepare Example 13 with the exception that 2(S)-amino-3-(4-fluoro-phenyl)-propionic acid methyl ester HCl (obtained from commercially available 2(S)-amino-3-(4-fluoro-phenyl)-propionic acid) was used.
The resulting ester was hydrolyzed by the general procedure C to afford the title compound.
LCMS: 570 (M+1)$^+$

Example 23

2(S)-{[7-(4-tert-Butyl-phenoxy)-1-cyclopentylmethyl-isoquinoline-3-carbonyl]-amino}-3-(5-propenylthiophen-2-yl)-propionic acid Compound E-2 was treated with tributyl-propenyl-stannane by the general procedure M to yield 2(S)-{[7-(4-tert-Butyl-phenoxy)-1-cyclopentylmethyl-isoquinoline-3-carbonyl]-amino}-3-(5-propenylthiophen-2-yl)-propionic acid methyl ester. The ester was hydrolyzed by the general procedure C to afford the title compound.
LCMS: 598 (M+1)$^+$

Example 24

2(S)-{[7-(4-tert-Butyl-phenoxy)-1-cyclopentylmethyl-isoquinoline-3-carbonyl]-amino}-3-(5-propylthiophen-2-yl)-propionic acid The title compound was prepared by treatment of 2(S)-{[7-(4-tert-Butyl-phenoxy)-1-cyclopentylmethyl-isoquinoline-3-carbonyl]-amino}-3-(5-propenylthiophen-2-yl)-propionic acid methyl ester (prepared in Example 23) with Pd/C and H$_2$ (1 atm) by the general procedure N to afford 2(S)-{[7-(4-tert-Butyl-phenoxy)-1-cyclopentylmethyl-isoquinoline-3-carbonyl]-amino}-3-(5-propylthiophen-2-yl)-propionic acid methyl ester. The ester was hydrolyzed by the general procedure C to afford the title compound.
LCMS: 600 (M+1)$^+$

Example 25

2(S)-{[7-(4-tert-Butyl-phenoxy)-1-cyclopentylmethyl-isoquinoline-3-carbonyl]-amino}-3-(5-(3,3-dimethyl-but-1-enyl)-thiophen-2-yl)-propionic acid Compound E-2 was treated with tributyl-(3,3-dimethyl-but-1-enyl)-stannane by the general procedure M to yield 2(S)-{[7-(4-tert-Butyl-phenoxy)-1-cyclopentylmethyl-isoquinoline-3-carbonyl]-amino}-3-(5-(3,3-dimethyl-but-1-enyl)-thiophen-2-yl)-propionic acid methyl ester. The ester was hydrolyzed by the general procedure C to afford the title compound.
LCMS: 640 (M+1)$^+$

Examples 26

2(S)-{[7-(4-tert-Butyl-phenoxy)-1-cyclopentylmethyl-isoquinoline-3-carbonyl]-amino}-3-[5-(hydroxymethylthiophen-2-yl]-propionic acid methyl ester (example 26):

To a solution of 2(S)-{[7-(4-tert-Butyl-phenoxy)-1-cyclopentylmethyl-isoquinoline-3-carbonyl]-amino}-3-(5-vinylthiophen-2-yl)-propionic acid methyl ester (prepared in Example 9) (0.650 g, 1.09 mmol) in acetone:water was added methylmorpholine-N-oxide (0.340 mL) and osmium tetroxide (2 crystals). The solution was stirred at 0° C. for 1.5 h. Ethyl acetate was added and extracted with a solution of Na$_2$S$_2$O$_4$(satd), brine, dried (Na$_2$SO$_4$), and concentrated under reduced pressure to give 0.600 g of 2(S)-{[7-(4-tert-Butyl-phenoxy)-1-cyclopentylmethyl-isoquinoline-3-carbonyl]-amino}-3-[5-(1,2-dihydroxy-ethyl)-thiophen-2-yl]-propionic acid methyl ester.

To a solution of this methyl ester (0.600 g, 0.954 mmol) in THF:water (1:1, 7 mL) was added NaIO$_4$ (0.816 g, 3.817 mmol) at 0° C. The reaction was stirred at 0° C. for 1.5 h. EtOAc was added and the organic layer was separated and washed with brine, dried (Na$_2$SO$_4$), and concentrated under reduced pressure to give product as an oil. The crude product was purified by flash column chromatography (silica, Hex:EtOAc) to give 0.220 g of 2(S)-{[7-(4-tert-Butyl-phenoxy)-1-cyclopentylmethyl-isoquinoline-3-carbonyl]-amino}-3-[5-(formyl-thiophen-2-yl]-propionic acid methyl ester.

To a solution of this methyl ester (0.060 g, 0.100 mmol) in anhydrous methanol (1.5 mL) was added NaBH$_4$ (15 mg) at 0° C. The reaction was stirred at 0° C. for 20 min. LCMS showed approximately 25% reduction of the ester group in the desired product to alcohol. The reaction mixture was concentrated and purified by flash column chromatography (silica, Hex:EtOAc) to yield 22 mg of 2(S)-{[7-(4-tert-Butyl-phenoxy)-1-cyclopentylmethyl-isoquinoline-3-carbonyl]-amino}-3-[5-(hydroxymethylthiophen-2-yl]-propionic acid methyl ester (Example 26).

Example 26
LCMS: 602 (M+1)$^+$

Example 27

2(S)-{[7-(4-tert-Butyl-phenoxy)-1-cyclopentylmethyl-isoquinoline-3-carbonyl]-amino}-3-[5-(hydroxymethylthiophen-2-yl]-propionic acid This was prepared by the hydrolysis of Example 26 by the general procedure C to afford the title compound.
LCMS: 588 (M+1)$^+$

Example 28

2(S)-{[7-(4-tert-Butyl-phenoxy)-1-cyclopentylmethyl-isoquinoline-3-carbonyl]-amino}-3-[5-(methyl-thiophen-2-yl]-propionic acid To a solution of Example 26 (0.060 g, 0.100 mmol), was added 4 Å MS and TMSCl (0.076 mL). To this was added NaBH$_3$CN (0.038 g, 0.601 mmol) at 0° C. The solution was warmed to rt and stirred for 18 h. The crude reaction mixture was purified by flash column chromatography (silica, Hex:EtOAc) to afford 8.5 mg of 2(S)-{[7-(4-tert-Butyl-phenoxy)-1-cyclopentylmethyl-isoquinoline-3-carbonyl]-amino}-3-[5-(methyl-thiophen-2-yl]-propionic acid methyl ester. This ester was hydrolyzed by the general procedure C to afford 5.0 mg of the title compound.
LCMS: 572 (M+1)$^+$

Example 29

2(S)-{[7-(4-tert-Butyl-phenoxy)-1-cyclopentylmethyl-isoquinoline-3-carbonyl]-amino}-3-(5-isopropenylthiophen-2-yl)-propionic acid The title compound was prepared by treatment of Compound E-2 with tributyl-isopropenyl-stannane and Pd(PPh$_3$)$_4$ as described in the general procedure M to afford 2(S)-{[7-(4-tert-Butyl-phenoxy)-1-cyclopentylmethyl-isoquinoline-3-carbonyl]-amino}-3-(5-isopropenylthiophen-2-yl)-propionic acid methyl ester. This ester was hydrolyzed by the general procedure C to afford the title compound.
LCMS: 598 (M+1)$^+$

Example 30

2(S)-{[7-(4-tert-Butyl-phenoxy)-1-cyclopentylmethyl-isoquinoline-3-carbonyl]-amino}-3-(5-isopropylthiophen-2-yl)-propionic acid The title compound was prepared by the treatment of 2(S)-{[7-(4-tert-Butyl-phenoxy)-1-cyclopentylmethyl-isoquinoline-3-carbonyl]-amino}-3-(5-isopropenylthiophen-2-yl)-propionic acid methyl ester (prepared in Example 29) with Pd/C and H$_2$ gas (1 atm) by the general procedure N to afford 2(S)-{[7-(4-tert-Butyl-phenoxy)-1-cyclopentylmethyl-1-isoquinoline-3-carbonyl]-amino}-3-(5-isopropylthiophen-2-yl)-propionic acid methyl ester. This ester was hydrolyzed by the general procedure C to afford the title compound.
LCMS: 600 (M+1)$^+$

Example 31

3-(5-bromo-thiophene-2-yl)-2(R)-{[7-(4-tert-Butyl-phenoxy)-1-cyclopentylmethyl-isoquinoline-3-carbonyl]-amino}-propionic acid Compound E-1 (0.150 g, 0.37 mmol) was reacted with (2R)-amino-3-(5-bromo-thiophen-2-yl)-propionic acid methyl ester HCl (0.145 g, 0.482 mmol), prepared from commercially available (2R)-amino-3-(5-bromo-thiophen-2-yl)-propionic acid as described in general procedure A to afford 0.180 g of 3-(5-bromo-thiophene-2-yl)-2(R)-{[7-(4-tert-Butyl-phenoxy)-1-cyclopentylmethyl-isoquinoline-3-carbonyl]-amino}-propionic acid methyl ester. This resulting ester was hydrolyzed by the general procedure C to afford 0.158 g of the title compound.
LCMS: 637 (M+1)$^+$

Example 32

2(R)-{[7-(4-tert-Butyl-phenoxy)-1-cyclopentylmethyl-isoquinoline-3-carbonyl]-amino}-3-(5-chloro-thiophen-2-yl)-propionic acid Compound E-1 was treated with 2(R)-amino-3-(5-chloro-thiophen-2-yl)-propionic acid methyl ester (obtained from commercially available 2(R)-amino-3-(5-chloro-thiophen-2-yl)-propionic acid) by the general procedure A to obtain 2(R)-{[7-(4-tert-Butyl-phenoxy)-1-cyclopentylmethyl-isoquinoline-3-carbonyl]-amino}-3-(5-chloro-thiophen-2-yl)-propionic acid methyl ester. The ester was hydrolyzed by the general procedure C to obtain the title compound.
LCMS: 592 (M+1)$^+$

Example 33

2(S)-{[7-(4-tert-Butyl-phenoxy)-1-cyclopentylmethyl-isoquinoline-3-carbonyl]-amino}-3-(5-chloro-furan-2-yl)-propionic acid Compound E-1 was treated with 2(S)-amino-3-(5-chloro-furan-2-yl)-propionic acid methyl ester HCl (obtained from commercially available 2(S)-amino-3-(5-chloro-furan-2-yl)-propionic acid) by the general procedure A to obtain 2(S)-{[7-(4-tert-Butyl-phenoxy)-1-cyclopentylmethyl-isoquinoline-3-carbonyl]-amino}-3-(5-chloro-furan-2-yl)-propionic acid methyl ester. The ester was hydrolyzed by the general procedure C to obtain the title compound.
LCMS: 576 (M+1)$^+$

Example 34

2(S)-{[7-(4-tert-Butyl-phenoxy)-1-cyclopentylmethyl-isoquinoline-3-carbonyl]-amino}-3-(2,5-dichloro-thiophen-3-yl)-propionic acid Compound E-1 was treated with 2(S)-amino-3-(2,5-dichloro-thiophen-3-yl)-propionic acid methyl ester HCl (obtained from commercially available 2(S)-amino-3-(2,5-dichloro-thiophen-3-yl)-propionic acid) by the general procedure A to obtain 2(S)-{[7-(4-tert-Butyl-phenoxy)-1-cyclopentylmethyl-isoquinoline-3-carbonyl]-amino}-3-(2,5-dichloro-thiophen-3-yl)-propionic acid methyl ester. The ester was hydrolyzed by the general procedure C to obtain the title compound.
LCMS: 626 (M+1)$^+$

Example 35

(5-Bromo-thiophen-2-yl)-{[7-(4-tert-Butyl-phenoxy)-1-cyclopentylmethyl-isoquinoline-3-carbonyl]-amino}-acetic acid Compound E-1 was treated with amino-(5-bromo-thiophen-2-yl)-acetic acid methyl ester (obtained from commercially available amino-(5-bromo-thiophen-2-yl)-acetic acid) by the general procedure A to obtain (5-Bromo-thiophen-2-yl)-{[7-(4-tert-Butyl-phenoxy)-1-cyclopentylmethyl-isoquinoline-3-carbonyl]-amino}-acetic acid methyl ester. The ester was hydrolyzed by the general procedure C to obtain the title compound.

LCMS: 622 (M+1)+

Example 36

3-(5-Bromo-furan-2-yl)-2(S)-{[7-(4-tert-Butyl-phenoxy)-1-cyclopentylmethyl-isoquinoline-3-carbonyl]-amino}-propionic acid Compound E-1 was treated with 2(S)-amino-(5-bromo-furan-2-yl)-propionic acid methyl ester HCl (obtained from commercially available 2(S)-amino-(5-bromo-furan-2-yl)-propionic acid) by the general procedure A to obtain 3-(5-Bromo-furan-2-yl)-2(S)-{[7-(4-tert-Butyl-phenoxy)-1-cyclopentylmethyl-isoquinoline-3-carbonyl]-amino}-propionic acid methyl ester. The ester was hydrolyzed by the general procedure C to obtain the title compound.

LCMS: 620 (M+1)+

Example 37

3-(5-Bromo-thiophen-2-yl)-2(S)-{[7-(4-trans-tert-butyl-cyclohexyloxy)-1-cyclopentylmethyl-isoquinoline-3-carbonyl]-amino}-propionic acid Compound E-3 was treated with (2S)-amino-3-(5-bromo-thiophen-2-yl)-propionic acid methyl ester HCl (prepared from commercially available (2S)-amino-3-(5-bromo-thiophen-2-yl)-propionic acid) by the general procedure A to afford 3-(5-Bromo-thiophen-2-yl)-2(S)-{[7-(4-trans-tert-butyl-cyclohexyloxy)-1cyclopentylmethyl-isoquinoline-3-carbonyl]-amino}-propionic acid methyl ester. The ester was hydrolyzed by the general procedure C to afford the title compound.

LCMS: 642 (M+1)+

Example 38

3-(5-Bromo-thiophen-2-yl)-2(S)-{[6-(4-tert-butyl-phenoxy)-1-cyclopentylmethyl-isoquinoline-3-carbonyl]-amino}-propionic acid Compound E-4 was treated with (2S)-amino-3-(5-bromo-thiophen-2-yl)-propionic acid methyl ester HCl (prepared from commercially available (2S)-amino-3-(5-bromo-thiophen-2-yl)-propionic acid) by the general procedure A to afford 3-(5-Bromo-thiophen-2-yl)-2(S)-{[6-(4-tert-butyl-phenoxy)-1-cyclopentylmethyl-isoquinoline-3-carbonyl]-amino}-propionic acid methyl ester. This ester was hydrolyzed by the general procedure C to afford the title compound.

LCMS: 636 (M+1)+

Example 39

2(S)-{[7-(4-trans-tert-butyl-cyclohexyloxy)-1-cyclopentylmethyl-isoquinoline-3-carbonyl]-amino}-3-(5-isopropenyl-thiophen-2-yl)-propionic acid 3-(5-Bromo-thiophen-2-yl)-2(S)-{[7-(4-trans-tert-butyl-cyclohexyloxy)-1-cyclopentylmethyl-isoquinoline-3-carbonyl]-amino}-propionic acid methyl ester (prepared in Example 37) was treated with tributyl-isopropenyl-stannane and Pd(PPh₃)₄ by the general procedure M to afford 2(S)-{[7-(4-trans-tert-butyl-cyclohexyloxy)-1-cyclopentylmethyl-isoquinoline-3-carbonyl]-amino}-3-(5-isopropenyl-thiophen-2-yl)-propionic acid methyl ester. This ester was hydrolyzed by the general procedure C to afford the title compound.

LCMS: 604 (M+1)+

Example 40

2(S)-{[7-(4-trans-tert-Butyl-cyclohexyloxy)-1-cyclopentylmethyl-isoquinoline-3-carbonyl]-amino}-3-(5-isopropyl-thiophen-2-yl)-propionic acid 2(S)-{[7-(4-trans-tert-butyl-cyclohexyloxy)-1-cyclopentylmethyl-isoquinoline-3-carbonyl]-amino}-3-(5-isopropenyl-thiophen-2-yl)-propionic acid methyl ester (prepared in Example 39) was treated with Pd/C and H₂(1 atm) by the general procedure N to afford 2(S)-{[7-(4-trans-tert-butyl-cyclohexyloxy)-1-cyclopentylmethyl-isoquinoline-3-carbonyl]-amino}-3-(5-isopropyl-thiophen-2-yl)-propionic acid methyl ester. This ester was hydrolyzed by the general procedure C to afford the title compound.

LCMS: 606 (M+1)+

Example 41

2(S)-{[7-(4-tert-butyl-phenoxy)-1-cyclopentylmethyl-isoquinoline-3-carbonyl]-amino}-3-(5-isopropyl-furan-2-yl)-propionic acid A solution of Compound E-1 (1 mmol) in DMF was treated with 2(S)-Amino-3-(5-bromo-furan-2-yl)-propionic acid methyl ester HCl (1.2 mmol, prepared from commercially available 2(S)-Amino-3-(5-bromo-furan-2-yl)-propionic acid) by the general procedure A to yield 3-(5-Bromo-furan-2-yl)-2(S)-{[7-(4-tert-butyl-phenoxy)-1-cyclopentylmethyl-isoquinoline-3-carbonyl]-amino}-propionic acid methyl ester.

The above bromide (1 mmol) was treated with tributyl-isopropenyl-stannane (1.5 mmol) and Pd(PPh₃)₄ (10 mol %) by the general procedure M to yield 2(S)-{[7-(4-tert-butyl-phenoxy)-1-cyclopentylmethyl-isoquinoline-3-carbonyl]-amino}-3-(5-isopropenyl-furan-2-yl)-propionic acid methyl ester.

The above alkene was reduced by the general procedure N to afford 2(S)-{[7-(4-tert-butyl-phenoxy)-1-cyclopentylmethyl-isoquinoline-3-carbonyl]-amino}-3-(5-isopropyl-furan-2-yl)-propionic acid methyl ester. This ester was hydrolyzed by the general procedure C to afford the title compound.

LCMS: 584 (M+1)+

Example 42

2(S)-{[1-cyclopentylmethyl-7-(4-isopropyl-cyclohexyloxy)-isoquinoline-3-carbonyl]-amino}-3-(5-isopropyl-thiophen-2-yl)-propionic acid The title compound was prepared by treatment of Compound E-8 (1 mmol) with E-6 (1.20 mmol) by the general procedure A to yield 2(S)-{[1-cyclopentylmethyl-7-(4-isopropyl-cyclohexyloxy)-isoquinoline-3-carbonyl]-amino}-3-(5-isopropyl-thiophen-2-yl)-propionic acid methyl ester. The ester was hydrolyzed by the general procedure C to afford the title compound.

LCMS: 592 (M+1)$^+$

Example 43

2(R)-{[7-(4-tert-Butyl-phenoxy)-1-cyclopentylmethyl-isoquinoline-3-carbonyl]-amino}-3-(5-isopropylthiophen-2-yl)-propionic acid 0.370 g (0.570 mmol) of 3-(5-bromo-thiophene-2-yl)-2(R)-{[7-(4-tert-Butyl-phenoxy)-1-cyclopentylmethyl-isoquinoline-3-carbonyl]-amino}-propionic acid methyl ester (prepared in Example 31) was reacted with Tributyl-isopropenyl-stannane (0.330 g, 0.997 mmol) and Pd(PPh$_3$)$_4$ (65 mg, 0.057 mmol) by the general procedure M to yield 0.295 g of coupled alkene product. The resulting alkene (95 mg) was reduced as described in the general procedure N to afford 84 mg of 2(R)-{[7-(4-tert-Butyl-phenoxy)-1-cyclopentylmethyl-isoquinoline-3-carbonyl]-amino}-3-(5-isopropylthiophen-2-yl)-propionic acid methyl ester. This ester (75 mg) was hydrolyzed by the general procedure C to afford 65 mg of the title compound as a white solid. 1H-NMR (400 MHz, CDCl3): δ 8.85 (d, 1H), 8.32 (s, 1H), 7.78 (d, 1H), 7.39 (m, 3H), 7.00 (d, 2H), 6.67 (s, 1H), 6.48 (s, 1H), 4.93 (d, 1H), 3.45 (d,2H), 2.97 (m, 3H), 2.27 (m, 1H), 1.58 (m, 6H), 1.34 (m, 9H), 1.21 (m, 8H). LCMS: 600 (M+2)$^+$.

LCMS: 600 (M+1)$^+$

Example 44

2(S)-{[7-(4-tert-Butyl-phenoxy)-isoquinoline-3-carbonyl]-amino}-3-(5-isopropyl-thiophen-2-yl)-propionic acid The title compound was prepared by the treatment of Compound E-10 (1 mmol) with Compound E-6 (1.2 mmol) by the general procedure A to afford 2(S)-{[7-(4-tert-Butyl-phenoxy)-isoquinoline-3-carbonyl]-amino}-3-(5-isopropyl-thiophen-2-yl)-propionic acid methyl ester. This ester was hydrolyzed by the general procedure C to afford title compound.

LCMS: 517 (M+1)$^+$

Example 45

2(S)-{[1-Cyclopentylmethyl-7-(4-trans-ethyl-cyclohexyloxy)-isoquinoline-3-carbonyl]-amino}-3-(5-isopropyl-thiophen-2-yl)-propionic acid The title compound was prepared by treatment of Compound E-9 (1 mmol) with Compound E-6 (1.20 mmol) by the general procedure A to yield 2(S)-{[1-cyclopentylmethyl-7-(4-ethyl-cyclohexyloxy)-isoquinoline-3-carbonyl]-amino}-3-(5-isopropyl-thiophen-2-yl)-propionic acid methyl ester. The ester was hydrolyzed by the general procedure C to afford the title compound.

LCMS: 578 (M+1)$^+$

Example 46

2(S)-{[1-cyclopentylmethyl-7-(4-isopropyl-phenoxy)-isoquinoline-3-carbonyl-amino}-3-(5-isopropyl-thiophen-2-yl)-propionic acid 1-cyclopentylmethyl-7-hydroxy-isoquinoline-3-carboxylic acid methyl ester (prepared in example E-1) was treated with 4-isopropylphenylboronic acid by the general procedure G to yield 7-(4-isopropyl-phenoxy)-1-cyclopentylmethyl-isoquinoline-3-carboxylic acid methyl ester. This ester was hydrolyzed by the general procedure C to afford 7-(4-isopropyl-phenoxy)-1-cyclopentylmethyl-isoquinoline-3-carboxylic acid. This acid was coupled with Compound E-6 by the general procedure A to yield 2(S)-{[1-cyclopentylmethyl-7-(4-isopropyl-phenoxy)-isoquinoline-3-carbonyl-amino}-3-(5-isopropyl-thiophen-2-yl)-propionic acid methyl ester. This ester was hydrolyzed by the general procedure C to afford the title compound.

LCMS: 586 (M+1)$^+$

Example 47

2(S)-{[7-(4-tert-Butyl-phenoxy)-1-(tetrahydro-pyran-4-yl)-isoquinoline-3-carbonyl]-amino}-3-(5-isopropyl-thiophen-2-yl)-propionic acid This was prepared by the treatment of Compound E-7 with Compound E-6 to afford 2(S)-{[7-(4-tert-Butyl-phenoxy)-1-(tetrahydro-pyran-4-yl)-isoquinoline-3-carbonyl]-amino}-3-(5-isopropyl-thiophen-2-yl)-propionic acid methyl ester. The ester was hydrolyzed by the general procedure C to give the title compound.

LCMS: 602 (M+1)$^+$

Example 48

2(S)-{[6-(4-tert-butyl-phenoxy)-1-cyclopentylmethyl-isoquinoline-3-carbonyl]-amino}-3-(5-isopropyl-thiophen-2-yl)-propionic acid 3-(5-Bromo-thiophen-2-yl)-2(S)-{[6-(4-tert-butyl-phenoxy)-1-cyclopentylmethyl-isoquinoline-3-carbonyl]-amino}-propionic acid methyl ester (prepared in Example 38) was treated with tributyl-isopropenyl-stannane and Pd(PPh$_3$)$_4$ as described in the general procedure M to afford 2(S)-{[6-(4-tert-butyl-phenoxy)-1-cyclopentylmethyl-isoquinoline-3-carbonyl]-amino}-3-(5-isopropenyl-thiophen-2-yl)-propionic acid methyl ester. This was treated with Pd/C and H$_2$ (1 atm) by the general procedure N to afford 2(S)-{[6-(4-tert-butyl-phenoxy)-1-cyclopentylmethyl-isoquinoline-3-carbonyl]-amino}-3-(5-isopropyl-thiophen-2-yl)-propionic acid methyl ester. This ester was hydrolyzed by the general procedure C to afford the title compound.

LCMS: 600 (M+1)$^+$

Example 49

2(S)-{[7-(4-tert-Butyl-phenyl)-1-cyclopentylmethyl-isoquinoline-3-carbonyl]-amino}-3-(5-isopropyl-thiophen-2-yl)-propionic acid 1-cyclopentylmethyl-7-hydroxy-isoquinoline-3-carboxylic acid methyl ester (prepared in Example E-1) was hydrolyzed by the general procedure C to afford 1-cyclopentylmethyl-7-hydroxy-isoquinoline-3-carboxylic acid. This acid (1 mmol) was coupled with Compound E-6 to afford 2(S)-[(1-cyclopentylmethyl-7-hydroxy-isoquinoline-3-carbonyl)amino]-3-(5-isopropyl-thiophen-2-yl)-propionic acid methyl ester.

To a stirring solution of above phenol (1 mmol), $Et_3N$ (2 mmol) and DMAP (cat.) in DCM was added, followed by excess trifluoromethanesulfonic anhydride (2 mmol) at 0° C. The reaction was stirred at rt for 30 min. The organic layer was separated, washed with citric acid, water, brine, dried ($Na_2SO_4$) and concentrated under reduced pressure to give the desired triflate which was used without further purification for the next step.

The above triflate (1 mmol) was treated with 4-tert-butylphenylboronic acid (2 mmol), $Pd(PPh_3)_4$ (0.05 mmol) and 2N $Na_2CO_3$ (3 mmol) solution by the general procedure D to afford 2(S)-{[7-(4-tert-Butyl-phenyl)-1-cyclopentylmethyl-isoquinoline-3-carbonyl]-amino}-3-(5-isopropyl-thiophen-2-yl)-propionic acid methyl ester. This ester was hydrolyzed by the general procedure C to afford the title compound.

LCMS: 584 (M+1)$^+$

Example 50

2(S)-{[7-(4-tert-Butyl-benzoyl)-1-cyclopentylmethyl-isoquinoline-3-carbonyl]-amino}-3-(5-isopropyl-thiophen-2-yl)-propionic acid The triflate of Example 49 (1 mmol), 4-tert-butylphenylboronic acid (1.40 mmol), $PdCl_2$(dppf) (10 mol %), potassium carbonate (3 mmol), and crushed NaI (3 mmol) were added to a flame dried flask. The flask was flushed with CO gas and then charged with anisole. The mixture was heated at 80° C. for 48 h under an atmosphere of CO. The reaction mixture was cooled to rt, filtered, and washed with EtOAc. The organic layer was washed with water, brine, dried, and concentrated under reduced pressure. The crude product was purified by flash chromatography (silica, Hexanes:EtOAc) to give pure 2(S)-{[7-(4-tert-Butyl-benzoyl)-1-cyclopentyl-methyl-isoquinoline-3-carbonyl]-amino}-3-(5-isopropyl-thiophen-2-yl)-propionic acid methyl ester. The ester was hydrolyzed by the general procedure C to afford the title compound.

LCMS: 612 (M+1)$^+$

Example 51

3-(5-Acetyl-thiophen-2-yl)-2(S)-{[7-(4-tert-butyl-phenoxy)-1-cyclopentylmethyl-isoquinoline-3-carbonyl]-amino}-propionic acid Compound E-2 (1.0 g, 1.53 mmol) was treated with tributyl-(1-ethoxy-vinyl)-stannane (0.83 g, 2.3 mmol), and $Pd(PPh_3)_4$ (0.177 g, 0.15 mmol) by the general procedure M to yield 0.600 g of 3-(5-Acetyl-thiophen-2-yl)-2(S)-{[7-(4-tert-butyl-phenoxy)-1-cyclopentylmethyl-isoquinoline-3-carbonyl]-amino}-propionic acid methyl ester. The ester (20 mg) was hydrolyzed by the general procedure C to afford the title compound.

LCMS: 600 (M+1)$^+$

Example 52

7-(4-tert-Butyl-phenoxy)-1-cyclopentylmethyl-isoquinoline-3-carboxylic acid [1-(5-isopropyl-thiophen-2-ylmethyl)-(2R)-methanesulfonylamino-2-oxo-ethyl]-amide To a solution of Example 43 (0.150 g, 0.250 mmol) in DCM was added oxalyl chloride (0.063 g, 0.50 mmol) and the solution was stirred for 45 min. The solution was concentrated and the solid was dried under vacuum. The solid was dissolved in DCM and methanesulfonamide (0.070 g, 0.750 mmol) was added followed by the $NEt_3$ (0.100 mL, 0.750 mmol) and the reaction was stirred for 2 h. The solution was concentrated and purified by flash chromatography (silica, DCM:MeOH) to afford 7 mg of title compound.

LCMS: 677 (M+1)$^+$

Example 53

7-(4-tert-Butyl-phenoxy)-1-cyclopentylmethyl-isoquinoline-3-carboxylic acid [1-(5-isopropyl-thiophen-2-ylmethyl)-(2S)-methanesulfonylamino-2-oxo-ethyl]-amide To a solution of Example 30 (0.105 g, 0.17 mmol) in THF was added CDI (0.085 g, 0.526 mmol) and the reaction was stirred at rt for 6 h. To this was added a solution of methanesulfonamide (0.035 g, 0.36 mmol) and DBU (0.040 g, 0.26 mmol) in THF and the reaction was heated at 60° C. for 3 h and stirred at rt for 3 h. The solution was concentrated under reduced pressure and the crude product was purified by the same procedure as used in Example 52 to afford 8 mg of the title compound.

LCMS: 677 (M+1)$^+$

Example 54

7-(4-tert-Butyl-phenoxy)-1-cyclopentylmethyl-isoquinoline-3-carboxylic acid [1-benzyloxycarbamoyl-2-(5-isopropyl-thiophen-2-yl)-ethyl]-amide A solution of Example 43 (0.090 g, 0.150 mmol) in DMF was treated with o-Benzylhyroxylamine hydrochloride (27 mg, 0.165 mmol), HBTU (0.063 g, 0.165 mmol), and DIEA (0.150 mL, 0.829 mmol) by the general procedure A. The crude product was purified by flash chromatography (silica, Hexanes:EtOAc) to afford 74 mg of title compound.

LCMS: 705 (M+1)$^+$

Example 55

7-(4-tert-Butyl-phenoxy)-1-cyclopentylmethyl-isoquinoline-3-carboxylic acid [1-hydroxycarbamoyl-2-(5-isopropyl-thiophen-2-yl)-ethyl]-amide Example 54 (68 mg, 0.09 mmol) was treated with $H_2$ (1 atm) and Pd/C by the general procedure N. The crude product was purified by flash chromatography (silica, $CH_2Cl_2$:$CH_3OH$) to afford 6 mg of title compound.

LCMS: 615 (M+1)$^+$

Biological Assay

The following assay methods may be used to identify compounds of Formula (I or X) that are effective in antagonizing the function of factor IX. Compounds of Formula (I or X) are effective in antagonizing the function of factor IX may be as inhibitors of the intrinsic clotting pathway.

General Assay Procedure

Factor IXa Florescence Based Molecular Assay:

To determine the $IC_{50}$ of compounds of Formula (I or X) relative to factor IXa, 12 µL solutions of compounds of Formula (I or X) at various concentrations (2% DMSO final concentration) were incubated for 10 min at room temp. with a 24 µL solution of FIXa (HCIXA-0050 Haemotologic Technologies Inc. Essex Junction, Vt.; 3.9 units/mL) in buffer containing 80% Ethylene glycol, 10 mM $CaCl_2$, 200 mM NaCl, and 100 mM Tris (pH 7.4) where the 24 µL solution of FIXa had an activity of 3.9 units/mL. The reaction was started by the addition of 12 µL of 0.5 mM FIXa substrate (Pefa-10148 from Pentapharm Basel, Switzerland; methyl sulfonyl-D-cyclohexylglycyl-glycyl-arginine-7-amino-4-methylcoumarid monoacetate, available from Centerchem, Inc.). After incubating the reaction for 10 min at room temp, the plate was read in a Spectromax Gemini fluorescence plate reader with and excitation wavelength of 340 nm and an emission wavelength of 440 nm. From the varying concentrations of test compound, $IC_{50}$'s are then calculated.

Factor XIa Chromogenic Based Molecular Assay:

To determine the $IC_{50}$ of compounds of Formula (I or X) relative to factor XIa, 20 µL solutions of compounds of Formula (I or X) at various concentrations (2% DMSO final concentration) were incubated for 10 min at room temp. with a 10 µL solution of FXIa (HCXIA-0160 from Haemotologic Technologies Inc. Essex Junction, Vt.) in buffer containing 50 mM Tris (pH 7.4) and 150 mM NaCl where the 10 µL solution of FXIa had an activity of 2 units/mL, and 150 µL of buffer. The reaction was started by the addition of 20 µL of 10 mM FXIa substrate (Pefa-3371 from Pentapharm Basel, Switzerland; Pyr-Phg-Arg-pNA monoacetate, available from Centerchem, Inc.). After incubating the reaction for 10 min at room temp, the plate was read in a Spectromax UV/vis plate reader at 405 nm.

FIXa In Vitro Clotting Assay

Compounds of Formula (I or X) of the present invention were evaluated for their inhibition of clotting in plasma to which exogenous Factor IXa was added. 20 µL solutions of compounds of Formula (I or X) at various concentrations having 2% DMSO were incubated with 30 µL FIXa (HCXIA-0160 from Haemotologic Technologies Inc. Essex Junction, Vt.) 3.2 units/mL in assay buffer containing 20 mM HEPES (pH 7.4) and 150 mM NaCl, 50 µL of 1:64 dilution of ALEXIN (trinity biosciences) in assay buffer, and 50 µL reconstituted human citrated plasma (Sigma) for 10 min at 37° C. The reaction was started by the addition of 50 µL of 40 mM $CaCl_2$ in assay buffer. The plate was read in kinetic mode at 405 nm and 37° C. immediately after addition of calcium. The plate was read for 5–10 min (depending on clot time) in 10 sec intervals on a Spectromax UV/vis plate reader.

FXIa In Vitro Clotting Assay:

Compounds of Formula (I or X) of the present invention were evaluated for their inhibition of clotting in plasma to which exogenous Factor XI was added. 20 µL solutions of compounds of Formula (I or X) at various concentrations having 2% DMSO were incubated with 30 µL FXIa (HCXIA-0160 from Haemotologic Technologies Inc. Essex Junction, Vt.) 0.4 units/mL in assay buffer containing 20 mM HEPES (pH 7.4) and 150 mM NaCl, 50 µL of 1:64 dilution of ALEXIN (trinity biosciences) in assay buffer, and 50 µL reconstituted human citrated plasma (Sigma) for 10 min at 37° C. The reaction was started by the addition of 50 µL of 40 mM $CaCl_2$ in assay buffer. The plate was read in kinetic mode at 405 nm and 37° C. immediately after addition of calcium. The plate was read for 5–10 min (depending on clot time) in 10 sec intervals on a Spectromax UV/vis plate reader.

The Examples in Table 1 either inhibit Factor IX in the Factor IXa Fluorescence assay, inhibit Factor XI in the Factor XIa Chromogenic assay, inhibit Factor IX in the Factor IXa in vitro clotting assay, or inhibit Factor XI in the in vitro clotting assay with an $IC_{50}$ of less than 30 µM. Various Examples in Table 1 may also have $IC_{50}$'s below 30 µM in more than one of the above-mentioned assays.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for factor IXa-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Moreover, all compounds that are recited in the written description are contemplated as possibilities for any of the recited methods, processes, compositions, and/or compounds as appear in the written description and the appended claims.

We claim:

1. A compound of Formula (X),

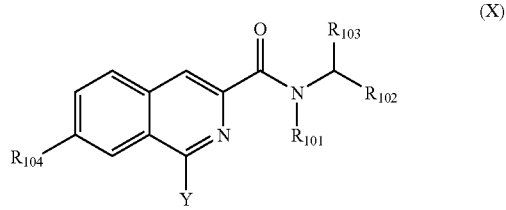

wherein
$R_{101}$ is selected from the group consisting of —H, or —$CH_2$-thienyl wherein the thienyl group in —$CH_2$-thienyl is optionally substituted with —Br or —$CH_3$;

$R_{102}$ is selected from the group consisting of —C(O)OH, —C(O)$OCH_3$, —C(O)O-t-butyl, —C(O)NH—$OCH_2$-phenyl, —C(O)NHOH, and —C(O)NH$SO_2CH_3$;

$R_{103}$ is selected from the group consisting of —H, —$CH_2$-thienyl, —$CH_2$-phenyl, —$CH_2$-furanyl, -thienyl, and benzothienyl wherein each of the above possibilities for $R_{103}$ except —H are optionally substituted with one or more members selected from group consisting of —H, —CH₃, —CF₃, —Cl, —Br, —F, —C(O)CH₃, —CH₂CH₃, —CH═CH₂, —CH₂OH, —CH(CH₃)₂, —CH₂CH₂CH₃, -propenyl, -3,3-dimethyl-butenyl, -isopropenyl, -phenyl, -phenylene-methyl, -phenylene-propyl, -phenylene-trifluoromethyl, -phenylene-chloride, -cyclopentyl, -cyclopentenyl, and -furanyl;

R₁₀₄ is selected from the group consisting of —O-cyclohexylene-ethyl, —O-cyclohexylene-t-butyl, —O-cyclohexylene-i-propyl, —O-phenylene-t-butyl, -phenylene-t-butyl, and —C(O)-phenylene-t-butyl;

and Y is selected from the group consisting of —H, -methylene-cyclopentyl, -amino-cyclohexyl, -methylene-thienylene-methyl, methylene-thienylene-bromide, and tetrahydropyranyl;

or a pharmaceutically acceptable salt, ester, or prodrug thereof.

2. A compound of Formula (X),

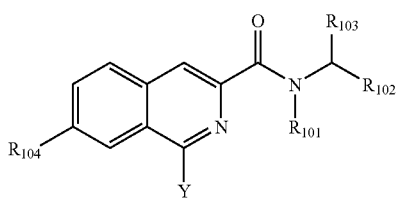

(X)

wherein R₁₀₁, is selected from the group consisting of —H, or —CH₂-thienyl wherein the thienyl group in —CH₂-thienyl is optionally substituted with —Br or —CH₃;

R₁₀₂ is selected from the group consisting of —C(O)OH, —C(O)OCH₃, —C(O)O-t-butyl, —C(O)NH—OCH₂-phenyl, —C(O)NHOH, and —C(O)NHSO₂CH₃;

R₁₀₃ is selected from the group consisting of —H, —CH₂-thienyl, —CH₂-phenyl, —CH₂-furanyl, thienyl, and benzothienyl wherein each of the above possibilities for R₁₀₃ except —H are optionally substituted with one or more members selected from group consisting of —H, —CH₃, —CF₃, —Cl, —Br, —F, —C(O)CH₃, —CH₂CH₃, —CH═CH₂, —CH₂OH, —CH(CH₃)₂, —CH₂CH₂CH₃,

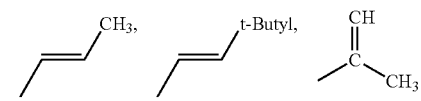

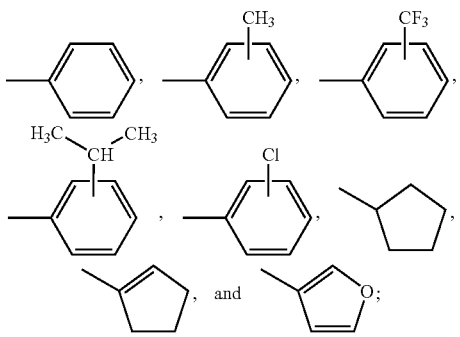

R₁₀₄ is selected from the group consisting of

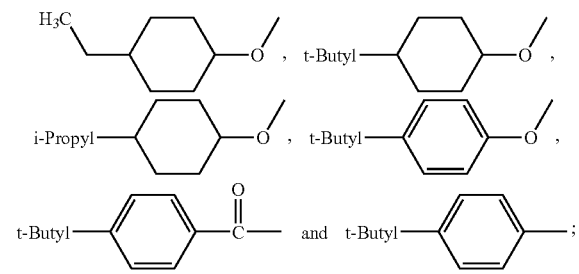

and Y is selected from the group consisting of H,

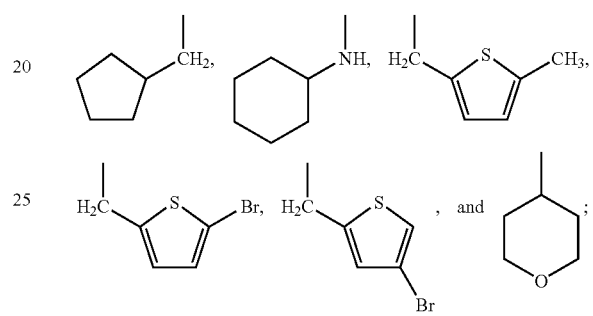

or a pharmaceutically acceptable salt, ester, or prodrug thereof.

3. The compound according to claim 2, wherein R₁₀₄ is

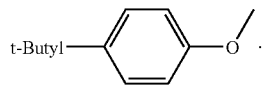

4. The compound according to claim 2, wherein R₁₀₃ is optionally substituted —CH₂-2-yl-thienyl or optionally substituted —CH₂-phenyl.

5. The compound according to claim 2, wherein R₁₀₃ is optionally substituted —CH₂-2-yl-thienyl.

6. The compound according to claim 3, wherein R₁₀₁ is —H.

7. The compound according to claim 3, wherein Y is selected from the group consisting of

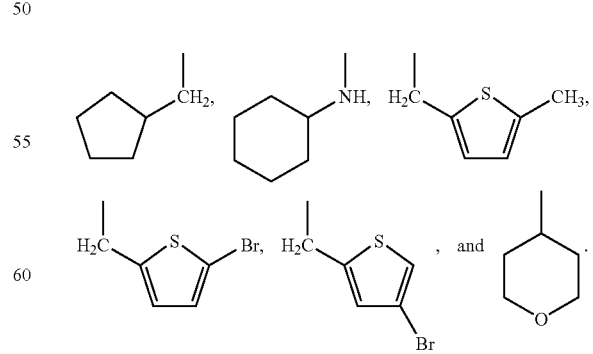

8. The compound according to claim 2, wherein the compound of Formula (X) is selected from the group consisting of 2(S)-{[7-(4-tert-Butyl-phenoxy)-1-cyclopentylmethyl-isoquinoline-3-carbonyl]-amino}-3-(5-phenyl-thiophen-2-yl)-propionic acid,
2(S)-{[7-(4-tert-Butyl-phenoxy)-1-cyclopentylmethyl-isoquinoline-3-carbonyl]-amino}-3-[5-(4-trifluoromethyl-phenyl)-thiophen-2-yl]-propionic acid,
2(S)-{[7-(4-tert-Butyl-phenoxy)-1-cyclopentylmethyl-isoquinoline-3-carbonyl]-amino}-3-(5-cyclopent-1-enyl-thiophen-2-yl)-propionic acid methyl ester,
2(S)-{[7-(4-tert-Butyl-phenoxy)-1-cyclopentylmethyl-isoquinoline-3-carbonyl]-amino}-3-(5-cyclopent-1-enyl-thiophen-2-yl)-propionic acid,
2(S)-{[7-(4-tert-Butyl-phenoxy)-1-cyclopentylmethyl-isoquinoline-3-carbonyl]-amino}-3-(5-cyclopentyl-thiophen-2-yl)-propionic acid methyl ester,
2(S)-{[7-(4-tert-Butyl-phenoxy)-1-cyclopentylmethyl-isoquinoline-3-carbonyl]-amino}-3-(5-cyclopentyl-thiophen-2-yl)-propionic acid,
2(S)-{[7-(4-tert-Butyl-phenoxy)-1-cyclopentylmethyl-isoquinoline-3-carbonyl]-amino}-3-(5-furan-3-yl-thiophen-2-yl)-propionic acid,
2(S)-{[7-(4-tert-Butyl-phenoxy)-1-cyclopentylmethyl-isoquinoline-3-carbonyl]-amino}-3-[5-(4-isopropyl-phenyl)-thiophen-2-yl]-propionic acid,
2(S)-{[7-(4-tert-Butyl-phenoxy)-1-cyclopentylmethyl-isoquinoline-3-carbonyl]-amino}-3-(5-vinyl-thiophen-2-yl)-propionic acid,
2(S)-{[7-(4-tert-Butyl-phenoxy)-1-cyclopentylmethyl-isoquinoline-3-carbonyl]-amino}-3-(5-p-tolyl-thiophen-2-yl)-propionic acid,
2(S)-{[7-(4-tert-Butyl-phenoxy)-1-cyclopentylmethyl-isoquinoline-3-carbonyl]-amino}-3-[5-(4-chloro-phenyl)-thiophen-2-yl]-propionic acid,
2(S)-{[7-(4-tert-Butyl-phenoxy)-1-cyclopentylmethyl-isoquinoline-3-carbonyl]-amino}-3-(5-ethyl-thiophen-2-yl)-propionic acid,
2(S)-{[7-(4-tert-Butyl-phenoxy)-1-cyclopentylmethyl-isoquinoline-3-carbonyl]-amino}-3-furan-2-yl-propionic acid,
2(S)-{[7-(4-tert-Butyl-phenoxy)-1-cyclopentylmethyl-isoquinoline-3-carbonyl]-amino}-3-(2-trifluoromethyl-phenyl)-propionic acid,
{(5-Bromo-thiophen-2-ylmethyl)-[7-(4-tert-butyl-phenoxy)-1-cyclopentylmethyl-isoquinoline-3-carbonyl]-amino}-acetic acid tert-butyl ester,
2(S)-{[7-(4-tert-Butyl-phenoxy)-1-cyclopentylmethyl-isoquinoline-3-carbonyl]-amino}-3-(3,5-difluorophenyl)-propionic acid,
[[7-(4-tert-Butyl-phenoxy)-1-cyclopentylmethyl-isoquinoline-3-carbonyl]-(5-methyl-thiophen-2-ylmethyl)-amino]-acetic acid,
{(5-Bromo-thiophen-2-ylmethyl)-[7-(4-tert-butyl-phenoxy)-1-cyclopentylmethyl-isoquinoline-3-carbonyl]-amino}-acetic acid methyl ester,
{(4-Bromo-thiophen-2-ylmethyl)-[7-(4-tert-butyl-phenoxy)-1-cyclopentylmethyl-isoquinoline-3-carbonyl]-amino}-acetic acid,
{(5-Bromo-thiophen-2-ylmethyl)-[7-(4-tert-butyl-phenoxy)-1-cyclopentylmethyl-isoquinoline-3-carbonyl]-amino}-acetic acid,
Benzo[b]thiophen-3-yl-{[7-(4-tert-butyl-phenoxy)-1-cyclopentylmethyl-isoquinoline-3-carbonyl]-amino}-acetic acid,
2(S)-{[7-(4-tert-Butyl-phenoxy)-1-cyclopentylmethyl-isoquinoline-3-carbonyl]-amino}-3-(4-fluoro-phenyl)-propionic acid,
2(S)-{[7-(4-tert-Butyl-phenoxy)-1-cyclopentylmethyl-isoquinoline-3-carbonyl]-amino}-3-(5-propenyl-thiophen-2-yl)-propionic acid,
2(S)-{[7-(4-tert-Butyl-phenoxy)-1-cyclopentylmethyl-isoquinoline-3-carbonyl]-amino}-3-(5-propyl-thiophen-2-yl)-propionic acid,
2(S)-{[7-(4-tert-Butyl-phenoxy)-1-cyclopentylmethyl-isoquinoline-3-carbonyl]-amino}-3-[5-(3,3-dimethyl-but-1-enyl)-thiophen-2-yl]-propionic acid,
2(S)-{[7-(4-tert-Butyl-phenoxy)-1-cyclopentylmethyl-isoquinoline-3-carbonyl]-amino}-3-(5-hydroxymethyl-thiophen-2-yl)-propionic acid methyl ester,
2(S)-{[7-(4-tert-Butyl-phenoxy)-1-cyclopentylmethyl-isoquinoline-3-carbonyl]-amino}-3-(5-hydroxymethyl-thiophen-2-yl)-propionic acid,
2(S)-{[7-(4-tert-Butyl-phenoxy)-1-cyclopentylmethyl-isoquinoline-3-carbonyl]-amino}-3-(5-methyl-thiophen-2-yl)-propionic acid,
2(S)-{[7-(4-tert-Butyl-phenoxy)-1-cyclopentylmethyl-isoquinoline-3-carbonyl]-amino}-3-(5-isopropenyl-thiophen-2-yl)-propionic acid,
2(S)-{[7-(4-tert-Butyl-phenoxy)-1-cyclopentylmethyl-isoquinoline-3-carbonyl]-amino}-3-(5-isopropylthiophen-2-yl)-propionic acid,
3-(5-Bromo-thiophen-2-yl)-2(R)-{[7-(4-tert-butyl-phenoxy)-1-cyclopentylmethyl-isoquinoline-3-carbonyl]-amino}-propionic acid,
2(R)-{[7-(4-tert-Butyl-phenoxy)-1-cyclopentylmethyl-isoquinoline-3-carbonyl]-amino}-3-(5-chloro-thiophen-2-yl)-propionic acid,
2(S)-{[7-(4-tert-Butyl-phenoxy)-1-cyclopentylmethyl-isoquinoline-3-carbonyl]-amino}-3-(5-chloro-furan-2-yl)-propionic acid,
2(S)-{[7-(4-tert-Butyl-phenoxy)-1-cyclopentylmethyl-isoquinoline-3-carbonyl]-amino}-3-(2,5-dichloro-thiophen-3-yl)-propionic acid,
(5-Bromo-thiophen-2-yl)-{[7-(4-tert-butyl-phenoxy)-1-cyclopentylmethyl-isoquinoline-3-carbonyl]-amino}-acetic acid,
3-(5-Bromo-furan-2-yl)-2(S)-{[7-(4-tert-butyl-phenoxy)-1-cyclopentylmethyl-isoquinoline-3-carbonyl]-amino}-propionic acid,
3-(5-Bromo-thiophen-2-yl)-2(S)-{[7-(4-trans-tert-butyl-cyclohexyloxy)-1-cyclopentylmethyl-isoquinoline-3-carbonyl]-amino}-propionic acid,
3-(5-Bromo-thiophen-2-yl)-2(S)-{[6-(4-tert-butyl-phenoxy)-1-cyclopentylmethyl-isoquinoline-3-carbonyl]-amino}-propionic acid,
2(S)-{[7-(4-trans-tert-Butyl-cyclohexyloxy)-1-cyclopentylmethyl-isoquinoline-3-carbonyl]-amino}-3-(5-isopropenyl-thiophen-2-yl)-propionic acid,
2(S)-{[7-(4-trans-tert-Butyl-cyclohexyloxy)-1-cyclopentylmethyl-isoquinoline-3-carbonyl]-amino}-3-(5-isopropyl-thiophen-2-yl)-propionic acid,
2(S)-{[7-(4-tert-Butyl-phenoxy)-1-cyclopentylmethyl-isoquinoline-3-carbonyl]-amino}-3-(5-isopropyl-furan-2-yl)-propionic acid,
2(S)-{[1-Cyclopentylmethyl-7-(4-isopropyl-cyclohexyloxy)-isoquinoline-3-carbonyl]-amino}-3-(5-isopropyl-thiophen-2-yl)-propionic acid,
2(R)-{[7-(4-tert-Butyl-phenoxy)-1-cyclopentylmethyl-isoquinoline-3-carbonyl]-amino}-3-(5-isopropyl-thiophen-2-yl)-propionic acid,
2(S)-{[7-(4-tert-Butyl-phenoxy)-isoquinoline-3-carbonyl]-amino}-3-(5-isopropyl-thiophen-2-yl)-propionic acid, 2(S)-{[1-Cyclopentylmethyl-7-(4-trans-ethyl-cyclohexyloxy)-isoquinoline-3-carbonyl]-amino}-3-(5-isopropyl-thiophen-2-yl)-propionic acid, 2(S)-{[1-Cyclopentylmethyl-7-(4-isopropyl-phenoxy)-isoquinoline-3-carbonyl]-amino}-3-(5-isopropyl-thiophen-2-yl)-propionic acid, 2(S)-{[7-(4-tert-Butyl-phenoxy)-1-(tetrahydro-pyran-4-yl)-isoquinoline-3-carbonyl]-amino}-3-(5-isopropyl-thiophen-2-yl)-propionic acid, 2(S)-{[6-(4-tert-Butyl-phenoxy)-1-cyclopentylmethyl-isoquinoline-3-carbonyl]-amino}-3-(5-isopropyl-thiophen-2-yl)-propionic acid, 2(S)-{[7-(4-tert-Butyl-phenyl)-1-cyclopentylmethyl-isoquinoline-3-carbonyl]-amino}-3-(5-isopropyl-thiophen-2-yl)-propionic acid, 2(S)-{[7-(4-tert-Butyl-benzoyl)-1-cyclopentylmethyl-isoquinoline-3-carbonyl]-amino}-3-(5-isopropyl-thiophen-2-yl)-propionic acid, 3-(5-Acetyl-thiophen-2-yl)-2(S)-{[7-(4-tert-butyl-phenoxy)-1-cyclopentylmethyl-isoquinoline-3-carbonyl]-amino}-propionic acid, 7-(4-tert-Butyl-phenoxy)-1-cyclopentylmethyl-isoquinoline-3-carboxylic acid [1-(5-isopropyl-thiophen-2-ylmethyl)-2(R)-methanesulfonylamino-2-oxo-ethyl]-amide, 7-(4-tert-Butyl-phenoxy)-1-cyclopentylmethyl-isoquinoline-3-carboxylic acid [1-(5-isopropyl-thiophen-2-ylmethyl)-2(S)-methanesulfonylamino-2-oxo-ethyl]-amide, 7-(4-tert-Butyl-phenoxy)-1-cyclopentylmethyl-isoquinoline-3-carboxylic acid [1-benzyloxycarbamoyl-2-(5-isopropyl-thiophen-2-yl)-ethyl]-amide, and 7-(4-tert-Butyl-phenoxy)-1-cyclopentylmethyl-isoquinoline-3-carboxylic acid [1-hydroxycarbamoyl-2-(5-isopropyl-thiophen-2-yl)-ethyl]-amide.

9. The compound according to claim 2, wherein Y is -methylene-cyclopentyl.

* * * * *